United States Patent [19]
Lee et al.

[11] Patent Number: 5,134,128
[45] Date of Patent: Jul. 28, 1992

[54] ANTI-INFLAMMATORY FURANONES

[75] Inventors: Gary C. M. Lee, Laguna Hills; Michael E. Garst, Newport Beach; John N. Bonfiglio, Mission Viejo; Elizabeth T. Syage, Cypress, all of Calif.

[73] Assignee: Allergan, Inc., Irvine, Calif.

[21] Appl. No.: 699,819

[22] Filed: May 13, 1991

Related U.S. Application Data

[63] Continuation-in-part of Ser. No. 192,808, May 11, 1988, abandoned, which is a continuation-in-part of Ser. No. 59,282, Jun. 8, 1987, abandoned, and a continuation-in-part of Ser. No. 501,637, Oct. 25, 1989, abandoned, which is a continuation-in-part of Ser. No. 281,154, Dec. 7, 1988, abandoned.

[51] Int. Cl.$^5$ ............... A61K 31/365; C07D 307/33; C07D 307/60
[52] U.S. Cl. ..................... 514/63; 514/314; 514/326; 514/336; 514/443; 514/444; 514/450; 514/471; 514/473; 546/174; 546/214; 546/283; 548/517; 549/58; 549/60; 549/214; 549/266; 549/313; 549/318; 549/323
[58] Field of Search ............ 546/174, 214, 283; 548/517; 549/58, 60, 214, 266, 313, 318, 323; 514/63, 314, 326, 336, 443, 444, 450, 471, 473

[56] References Cited

U.S. PATENT DOCUMENTS

| | | | |
|---|---|---|---|
| 2,359,096 | 9/1944 | Elderfield | 260/239.5 |
| 2,359,208 | 9/1944 | Elderfield | 260/344 |
| 4,447,445 | 5/1984 | Jacobs | 424/279 |
| 4,786,651 | 11/1988 | Wheeler | 514/460 |
| 4,789,749 | 12/1988 | Jacobs et al. | 549/313 |
| 4,855,320 | 8/1989 | Chatterjee et al. | 514/473 |
| 4,874,782 | 10/1989 | Bonjouklian et al. | 514/473 |
| 4,916,241 | 4/1990 | Hayward et al. | 549/313 |
| 4,935,530 | 6/1990 | Lee | 549/214 |
| 5,013,850 | 5/1991 | Lee | 549/222 |
| 5,037,811 | 8/1991 | Lee | 514/99 |
| 5,043,457 | 8/1991 | Lee | 549/222 |
| 5,045,564 | 9/1991 | Lee | 514/471 |

FOREIGN PATENT DOCUMENTS

| | | |
|---|---|---|
| 133376 | 2/1985 | European Pat. Off. . |
| 209274 | 1/1987 | European Pat. Off. . |
| 295056 | 6/1987 | European Pat. Off. . |
| 350878 | 1/1990 | European Pat. Off. . |

OTHER PUBLICATIONS

Bonjouklian, et al., Chemical Abstracts, vol. 106, 156260c, p. 670 (1987).
Reynolds, et al., J. Am. Chem. Soc., 110, pp. 5172–5177 (1988).
Tocanne et al., Chemical Abstracts 69 76581k, p. 7146 (1968).
Deems, et al., Biochimica et Biophysica Acta, 917, pp. 258–268 (1987).
Scheuer et al., Journal of the American Chemical Society 100:1, p. 307 (Jan. 4, 1978).
Graziano, et al., Chemical Abstracts 107, (1987), 236559t.
Roll et al., Org. Chem. 1988, 53, 3276–3278.
Negishi et al., J. Org. Chem. 45, pp. 5223–5225, (1980).
E. D. de Silva et al., "Tetrahedron Letters", 21: 1611–1614 (1980).
Nakagawa et al., "Aldose Reductase Inhibitor from Palaun Sponges", Chem. Abstract 106: 96126b.
Tanaka, et al., The Chemical Society of Japan, Chemistry Letters, pp. 633–636 (1983).
Tanis, et al., Tetrahedron Letters, vol. 25, No. 40, pp. 4451–4454 (1984)–Furans in Synthesis 4. Silyl Furans as Butenolide Equivalents.
Graziano, et al., "Photosensitized Oxidation of Furans, Part 12, Solvent Effects in Thermal Rearrangement of the 2,5-Peroxides of 2,5-Unsubstituted Furans", J. Chem. Soc., Perkin Trans., 1, (8), 1833–1839, Apr. 19, 1989.
David Nettleton, et al., Inflammation Research Association, Fifth International Conference Poster Session, Phospholipase $A_2$ Inhibition by Dihydrofuranones, Sep. 23–27, 1990.

Primary Examiner—Richard L. Raymond
Attorney, Agent, or Firm—Gabor L. Szekeres; Martin A. Voet; Robert J. Baran

[57] ABSTRACT

New 5-hydroxy-2-furanone compounds having anti-inflammatory, immunosuppressive and anti-proliferative activity and are useful in treating psoriasis and modifying calcium homeostasis.

30 Claims, No Drawings

ANTI-INFLAMMATORY FURANONES

CROSS-REFERENCE TO RELATED APPLICATIONS

The present application is a continuation-in-part of application Ser. No. 192,808, filed on May 11, 1988, now abandoned which is itself a continuation-in-part of application Ser. No. 059,282 filed on Jun. 8, 1987 now abandoned, and of application Ser. No. 501,637 filed on Oct. 25, 1989, now abandoned, which is itself a continuation-in-part of application Ser. No. 281,154, filed on Dec. 7, 1988, now abandoned.

This invention relates to new furanone compounds having anti-inflammatory activity, pharmaceutical compositions comprising these compounds and to methods of using them.

BACKGROUND OF THE INVENTION

Manoalide is a furanone compound isolated from marine sponge as reported by E. D. de Silva et al., *Tetrahedron Letters* 21:1611-1614 (1980). Anti-inflammatory, immunosuppressive and analgesic properties of manoalide are disclosed in U.S. Pat. No. 4,447,445. Manoalide has the following structural formula:

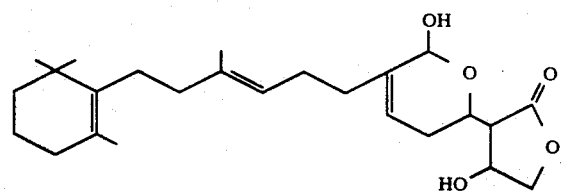

The anti-inflammatory activity of seco-manoalide and dehydro-seco-manoalide is also disclosed in U.S. Pat. No. 4,447,445.

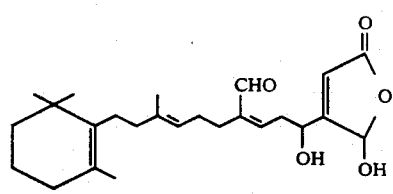

seco-manoalide

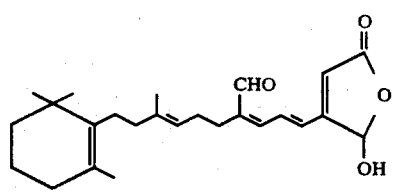

dehydro-seco-manoalide

THE INVENTION

The compounds of the present invention are represented by Formula I:

FORMULA I

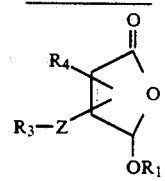

in which
the dotted line represents absence of a bond or a single bond;

$R_1$ is hydrogen, $C_1$-$C_4$ alkyl, benzyl, or acyl such as $C_1$-$C_{20}$ alkanoyl, cyclohexanoyl, benzoyl, phenyl ($C_{1-4}$ alkanoyl) or naphthoyl;

Z is —CO— or —C(OR$_2$)H—;

$R_2$ is hydrogen $C_1$-$C_{20}$ alkanoyl, trihaloacetyl, cyclohexanoyl, benzoyl, phenyl($C_{1-4}$ alkanoyl), phenyl($C_2$-$C_{14}$ alkenoyl), naphthoyl, or carbamoyl optionally N-substituted by one or two $C_{1-4}$ alkyl groups or by one α-($C_1$-$C_4$ alkyl)benzyl group;

$R_3$ is hydrogen, $C_1$-$C_{20}$ straight chain alkyl, phenyl($C_1$-$C_{20}$ straight chain alkyl or alkenyl of 1-6 unconjugated double bonds), cyclohexyl($C_1$-$C_{20}$ straight chain alkyl or alkenyl having 1-6 unconjugated double bonds), phenyl, cyclohexyl or benzothienyl($C_1$-$C_{20}$ alkyl or alkenyl having 1-6 unconjugated double bonds), 4-methyl-3-pentenyl, 4-methyl-6-(2,6,6-trimethyl-cyclohex-1-enyl)hex-3-enyl, 1-(2-ethenyl)-1,5,9-trimethyl-deca-4,8-dienyl, Y—(CH$_2$)$_n$ or B-(straight chain $C_3$-$C_{14}$ alkynyl);

$R_4$ is hydrogen, bromo or chloro but is not bromo or chloro when $R_3$ contains a double bond;

n is 6-12;

Y is OR$_5$, CO$_2$R$_6$, t-butyl, t-butyldimethylsilyl, diphenylmethyl, triphenylmethyl, pyridyl, thienyl, quinolyl, N—$C_1$-$C_4$ alkylpyrrolyl, N—$C_1$-$C_4$ alkylpiperidyl, N—$C_1$-$C_4$ alkylpyridinium halide or naphthyl;

$R_5$ is hydrogen, $C_1$-$C_4$ alkyl or $C_1$-$C_4$ alkanoyl;

$R_6$ is hydrogen or $C_1$-$C_4$ alkyl;

B is hydrogen, phenyl, pyridyl or naphthyl; and a lactone formed when $R_2$ is hydrogen and $R_3$ is (CH$_2$)$_{11-15}$ COOH; said phenyl in the definition of $R_3$ being optionally substituted by $C_1$-$C_{14}$ alkyl, alkenyl, alkynyl or aryl, CO$_2$R$_6$, $C_1$-$C_4$ alkoxy or halo.

Particular compounds of this invention are represented by Formula I in which:

$R_1$ is hydrogen or $C_1$-$C_{20}$ alkanoyl;

$R_2$ is hydrogen, $C_1$-$C_{20}$ alkanoyl, phenyl ($C_1$-$C_4$ alkanoyl) or carbamoyl optionally N-substituted by one or two $C_1$-$C_4$ alkyl groups or by one α-($C_1$-$C_4$ alkyl)-benzyl group;

$R_3$ is $C_5$-$C_{20}$ straight chain alkyl or benzothienyl($C_1$-$C_{20}$ alkyl); and $R_4$ is hydrogen.

Preferred compounds of this invention are:
4-(1-acetoxy-7-benzo[b]thien-2-yl-heptyl)-5-hydroxy-2(5H)-furanone;
4-(1-acetoxy-6-phenylhexyl)-5-hydroxy-2(5H)-furanone;
4-[1-acetoxy-5-methyl-7-(2,6,6-trimethylcyclohex-1-enyl)-hept-4-enyl]-5-hydroxy-2(5H)-furanone;
4-(1-acetoxytridecyl)-5-hydroxy-2(5H)-furanone and
4-[1-(α-methylbenzylcarbamoyl)tridecyl]-5-hydroxy-2(5H)-furanone.

Furthermore compounds of the present invention are represented by the Formula II

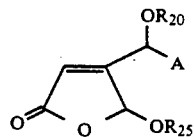

FORMULA II in which:

$R_{20}$ is hydrogen, $C_1$–$C_{14}$ alkanoyl, $CONHR_{23}$ or $CO_2R_{24}$;

$R_{23}$ is phenyl or $C_1$–$C_4$ alkyl;

$R_{24}$ is $C_1$–$C_6$ alkyl;

A is $CH_2O$—$R_{21}$ or $CH(C_7$–$C_{14}$ alkyl); $OCOR_{22}$ when $R_{20}$ is $C_7$–$C_{14}$ alkanoyl, A may be $CH_2OCOR_{22}$ or $CH_2OP(O)(OR_{22})R_{22}$;

$R_{21}$ is $C_1$–$C_{14}$ alkanoyl, N-($C_6$–$C_{14}$ alkyl) carbamoyl, naphthyl-($C_1$–$C_6$ alkyl), pyridyl-($C_1$–$C_6$ alkyl) or methoxyethoxymethyl;

$R_{22}$ is $C_1$–$C_4$ alkyl;

The hydroxy group in the 5-position on the furanone ring may be acylated or alkylated by standard procedures, for example, by reacting the hydroyfuranone with an acyl anhydride or halide or with an alkyl halide to give compounds also having anti-inflammatory activity as do the 5-hydroxyfuranones. Therefore, $R_{25}$ is H, $C_{1-6}$ alkanoyl or $C_{1-6}$ alkyl.

Particular compounds of this invention are represented by Formula II in which:

$R_{20}$ is $C_1$–$C_{14}$ alkanoyl and A is $CH_2O$—$R_{21}$. In these compounds, $R_{21}$ is, in particular, $C_8$–$C_{14}$ alkanoyl, naphthylpropyl, pyridylpropyl or methoxyethoxymethyl.

Specific compounds of this invention represented by Formula II are:

4-[1-dodecanoyloxy-2-(2-methoxyethoxy)methoxyethyl]-5-hydroxy-2(5H)-furanone, 4-(1,2-didodecanoyloxyethyl)-5-hydroxy-2(5H)-furanone, 4-(1-acetoxy-2-[3-(2-naphthyl)propoxy]-ethyl)-5-hydroxy-2(5H)-furanone, and 4-[1-hydroxy-2-[3-(2-naphthyl)propoxy]-ethyl]-5-hydroxy-2(5H)-furanone.

The compounds of this invention may contain chiral centers and accordingly, may be prepared as enantiomeric or diasteriomeric mixtures or in optically pure form. Unless otherwise specified herein, the preparations are racemates at each chiral center. However, the scope of the invention is not to be considered as limited to these forms but also to encompass the individual optical isomers of the compounds.

Compounds of the invention which are represented by Formula I are prepared by the following procedures:

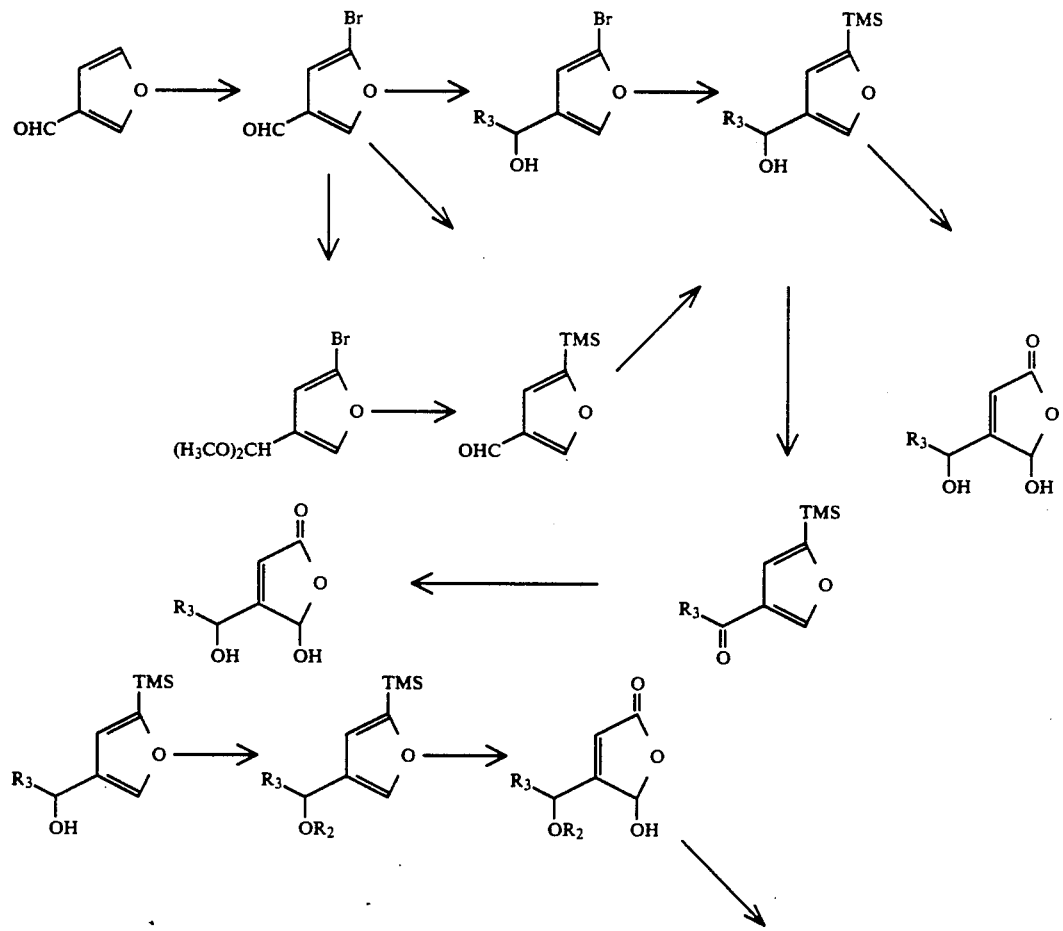

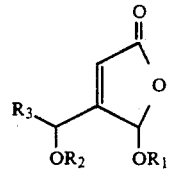

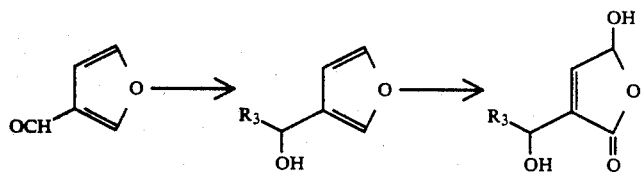

$R_1$, $R_2$ and $R_3$ are as defined hereabove and TMS is trimethylsilyl.

According to the above procedure, 3-furaldehyde is brominated to give 5-bromo-3-furaldehyde which is then reacted with a Grignard reagent ($R_3$MgX) and the resulting mixture treated with t-butyl lithium and trimethylsilyl chloride to give 4-[$R_3$—CH(OH)]-2-trimethylsilylfuran. Alternatively, 5-bromo-3-furaldehyde is converted to the dimethylacetal, then treated with t-butyl lithium and trimethylsilyl chloride to give 5-trimethylsilyl-3-furaldehyde which is reacted with $R_3$MgX or $R_3$Li to give 4-[$R_3$—CH(OH)]-2-trimethylsilylfuran. Treating this intermediate with oxygen and irradiation using an initiator such as Rose Bengal gives 4-[$R_3$—CH(OH)]-5-hydroxy-2(5H)-furanone.

A preferred method for preparing 5-trimethylsilyl-3-furaldehyde is by reacting lithium morpholide and butyl lithium with 5-bromo-3-furaldehyde to protect the aldehyde group, then reacting with butyl lithium and trimethylsilyl chloride to give 5-trimethylsilyl-3-furaldehyde.

Alternatively, 4-[$R_3$—CH(OH)]-2-trimethylsilylfuran is reacted with an acyl anhydride or halide to give 4-[$R_3$—CH(O$R_2$)]-2-trimethylsilylfuran. Treatment with oxygen and irradiation using an initiator such as Rose Bengal gives 4-[$R_3$—CH(O$R_2$)]-5-hydroxy-2(5H)-furanone. The corresponding 5-alkanoyl compounds are prepared by reacting the 5-hydroxyfuranone with an acyl anhydride or halide.

The 3-($R_3$-Z)-furanones of Formula I are prepared by reacting 3-furaldehyde with a Grignard reagent ($R_3$MgX) to give 3-[$R_3$—CH(OH)]-furan. This intermediate is treated with oxygen and irradiated using an initiator such as Rose Bengal to give 3-[$R_3$—CH(OH)]-5-hydroxy-2(5H)-furanone and the corresponding 4-[$R_3$—CH(OH)] isomer. These isomers are separated, for example, by chromatography.

The compounds in which $R_1$ and/or $R_2$ is alkyl are prepared by alkylating the corresponding hydroxy compounds by standard procedures, for example, by using an alkyl halide. When $R_1$ and $R_2$ are both hydroxy groups, one may be protected, for example, with an ester group while the other is alkylated or acylated.

The compounds in which $R_1$ is benzyl are prepared by standard procedures, for example, by treating the corresponding hydroxy compound with benzyl alcohol with a trace of acid in benzene.

The compounds of Formula I in which $R_4$ is bromo or chloro are prepared by brominating or chlorinating a 5-methoxy-2(5H)-furanone and then dehydrobrominating or dehydrochlorinating the resulting 3,4-dihalo furanone intermediate by standard procedures.

The compounds of Formula I wherein Z is —CO— are prepared by oxidizing the hydroxy group of the 3-$R_3$—CH(OH) furan intermediates using an oxidizing agent such as pyridinium chlorochromate.

Compounds of the invention which are represented by Formula II are prepared from 5-trimethylsilyl(TMS)-3-furaldehyde by procedures which are illustrated hereinbelow and described in more detail in the examples.

Procedure II

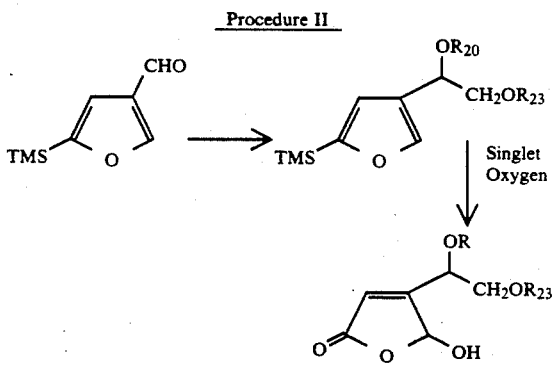

In this scheme, $R_{23}$ is naphthylalkyl, pyridylalkyl, or methoxyethoxymethoxymethyl.

Procedure III

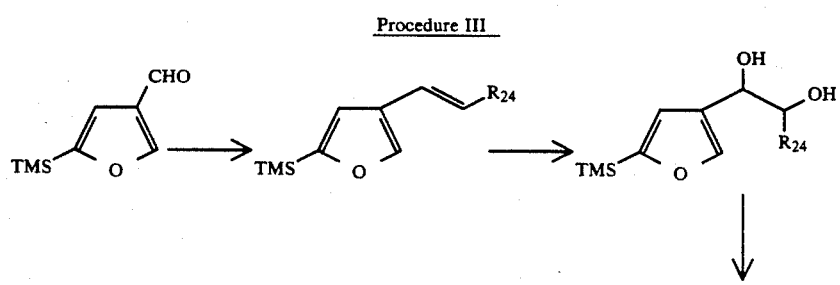

Procedure III

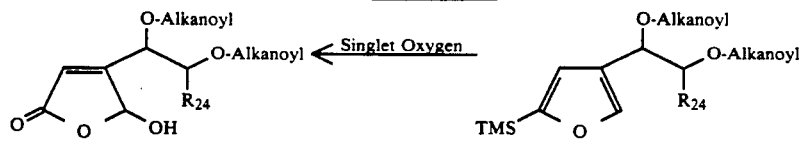

In this procedure $R_{24}$ is hydrogen or alkyl.

According to procedure II, the aldehyde group of 5-trimethylsilyl-3-furaldehyde is reacted with $R_{23}$ tributylstannylmethyl ether, the 2-OH group is optionally O-alkanoylated and the resulting 5-trimethylsilyl-3-(CH(OR)CH$_2$OR$_{23}$)-furan is converted to the corresponding 5-hydroxy-2-furanone by treating with oxygen and irradiating using an initiator such as Rose Bengal.

By procedure III the aldehyde group of 5-trimethylsilyl-3-furaldehyde is converted to a vinyl group, for example by Witting reaction with an alkyl triphenylphosphonium bromide/butyl lithium; the vinyl group is oxidized using, for example, osmium tetroxide; the resulting 1,2-dihydroxy groups are O-alkanoylated; and the resulting intermediate is oxidized as described above to give the 5-hydroxy-2-furanone.

The 5-trimethylsilyl-3-furaldehyde starting material may be prepared by brominating 3-furaldehyde to give 5-bromo-3-furaldehyde which is converted to the dimethylacetal, then treated with t-butyl lithium and trimethylsilyl chloride.

A preferred method for preparing 5-trimethylsilyl-3-furaldehyde is by reacting lithium morpholide with 5-bromo-3-furaldehyde to protect the aldehyde group, then reacting with t-butyl lithium and trimethylsilyl chloride to give 5-trimethylsilyl-3-furaldehyde.

An improved method for preparing 5-trimethylsilyl-3-furaldehyde consists of reacting lithium morpholide with 3-furaldehyde, followed by secondary-butyl lithium, followed by trimethylsilyl chloride. This method is also advantageous for the preparation of 5-triethylsilyl-3-furaldehyde using triethylsilylchloride. 5-triethylsilyl-3-furaldehyde is useful as an intermediate in place of the trimethyl compound in methods described herein for preparing compounds of this invention.

In addition, this invention relates to pharmaceutical compositions containing the compounds of Formula I as active ingredients and to methods of using the compounds and pharmaceutical compositions of this invention to produce anti-inflammatory, immunosuppressant and anti-proliferative activity. These compounds are useful in treating inflammation, in suppressing unwanted immune responses and in retarding proliferation of cells. Uses include treatment of rheumatoid arthritis, osteoarthritis, rheumatic carditis and autoimmune diseases such as allergic diseases, bronchial asthma and myasthenia gravis and ocular and dermal inflammatory diseases. The compounds are useful in treating psoriasis, acne, atopic diseases and allergic conjunctivitis. They are also useful as adjuvant therapy associated with organ and tissue transplants.

The activity of the compounds of this invention is demonstrated by inhibition of the enzyme phospholipase A$_2$ in vitro and by reduction of inflammation in the mouse ear anti-inflammatory assay in vivo.

The compounds also inhibit ornithine decarboxylase, a rate limiting enzyme in cellular growth, which indicates use in treating psoriasis and neoplasis.

The compounds also modify calcium homeostasis. This activity is shown by effect on intracellular calcium levels in experiments using gastric glands, spleen cells, epithelial cells, GH$_3$ cells, etc. Calcium is inhibited from entering through the plasma membrane calcium channels and calcium release from intracellular stores is also blocked. Modification of calcium homeostasis is expected to have application in diseases of the nervous system involving modification of membrane lipids or transmitter release (Parkinson's, Alzheimer's), diseases of the cardiovascular system involving application of cardiac or vascular smooth muscle contractility and platelet aggregation (hypertension, cardiac infarction and atherosclerosis), diseases of the gastrointestinal tract such as ulcer disease, diarrhea, motility due to secretion of acid or Cl$^-$, diseases of the kidney involving renal handling of fluid and electrolytes (metabolic acidosis, alkalosis), and disease of abnormal growth (neoplasia, psoriasis).

The compounds of this invention have activity which is similar to that of manoalide, that is the compounds appear to be devoid of the endocrine properties of the glucocorticoids while having anti-inflammatory and immunosuppressive properties. They have activity in substantially the same dose range as manoalide.

In the methods of this invention, the compounds of the invention are administered to mammals, including humans, in an effective amount to produce the desired activity, preferably in an amount of about 0.05 to 100 mg per day per kilogram of body weight. The amount of the compound depends upon the disease or condition being treated, the severity thereof, the route of administration and the nature of the host. The compounds may be administered topically, orally, parenterally or by other standard routes of administration.

Pharmaceutical compositions of this invention comprise compounds of Formula I and pharmaceutical carriers suitable for the route of administration. Standard methods for formulating pharmaceutical compositions of this type may be found in *Remington's Pharmaceutical Sciences*, Mack Publishing Company, Easton, Pa.

For topical administration, the pharmaceutical composition may be in the form of a salve, cream, ointment, spray, powder or the like. Standard pharmaceutical carriers for such compositions may be used. Preferably, compositions for topical administration will contain 0.05-5% of the active ingredient.

A typical cream formulation may contain the following:

| Ingredient | Parts by Weight |
| --- | --- |
| Water/glycol mixture (15% or more glycol) | 50-99 |
| Fatty alcohol | 1-20 |
| Non-ionic surfactant | 0-10 |
| Mineral oil | 0-10 |
| Typical pharmaceutical adjuvants | 0-5 |

-continued

| Ingredient | Parts by Weight |
| --- | --- |
| Active ingredient | 0.05-5 |

A typical ointment formulation may contain the following:

| Ingredients | Parts by Weight |
| --- | --- |
| White petrolatum | 40-94 |
| Mineral Oil | 5-20 |
| Glycol solvent | 1-15 |
| Surfactant | 0-10 |
| Stabilizer | 0-10 |
| Active ingredient | 0.05-5 |

For oral administration, suitable pharmaceutical carriers include mannitol, lactose, starch, magnesium stearate, talcum, glucose and magnesium carbonate. Oral compositions may be in the form of tablets, capsules, powders, solutions, suspensions, sustained release formulations, and the like.

A typical tablet or capsule may contain the following:

| Ingredients | Percent w/w |
| --- | --- |
| Lactose, spray-dried | 40-99 |
| Magnesium stearate | 1-2 |
| Cornstarch | 10-20 |
| Active ingredient | 0.001-20 |

Parenteral compositions are prepared in conventional suspension or solution forms, as emulsions or as solid forms for reconstruction. Suitable carriers are water, saline, dextrose, Hank's solution, Ringer's solution, glycerol, and the like. Parenteral administration is usually by injection which may be subcutaneous, intramuscular or intravenous.

The compounds of this invention may be combined with other known anti-inflammatory/immunosuppressive agents such as steroids or non-steroidal anti-inflammatory agents (NSAID) in the pharmaceutical compositions and methods described herein.

The following examples are intended to illustrate the invention but are not limiting. All temperatures are in degrees Centigrade. NMR data are recorded in delta ppm.

EXAMPLE 1

5-Bromo-3-furaldehyde, dimethylacetal

To a 250 ml 3 neck round-bottom flask equipped with a reflux condenser and addition funnel, containing a rapidly stirring solution of 3-furaldehyde (2.8 g., 29.44 mmol) in 100 ml of methylene chloride at 0° was added aluminum bromide (11.9 g., 44.22 mmol) under a positive pressure of argon. This mixture was then heated to reflux and bromine (5.30 g., 33.17 mmol) in 20 ml methylene chloride was added dropwise. After one hour the reaction mixture was cooled to room temperature and quenched by pouring over crushed ice. The resulting mixture was filtered through celite and partitioned between methylene chloride and a 5% sodium bicarbonate solution. The organic portion was washed with water, saturated sodium chloride solution, dried over magnesium sulfate, filtered and concentrated to yield the bromoaldehyde as an amber oil. This was immediately diluted with 100 ml of a 0.4M methanolic solution of cerium chloride heptahydrate. Trimethylorthoformate (32.2 g., 0.303 mol) was then added and the mixture was stirred at room temperature for 3.5 hours. The methanol was evaporated and the residue partitioned between ether and a 5% sodium bicarbonate solution. The organic portion was washed with saturated sodium chloride solution, dried over magnesium sulfate, filtered and concentrated to give an amber oil. This material was further purified by flash chromatography (5% ethyl acetate/hexane) to give the desired bromoacetal.

$^1$H NMR (CDCl$_3$): 7.43 (s, 1H); 6.32 (s, 1H); 5.36 (s, 1H); 3.30 (s, 3H); 3.29 (s, 3H).

$^{13}$C NMR (CDCl$_3$): 142.4, 126.4, 122.5, 110.4, 97.7, 52.0

5-Trimethylsilyl-3-furaldehyde

To a stirred solution of 5-bromo-3-furaldehyde, dimethyl acetal (1.26 g., 5.7 mmol) in 10 ml dry tetrahydrofuran at 78° under argon was added t-butyllithium (9.69 mmol in pentane), followed by the subsequent addition of trimethylsilyl chloride (1.36 g., 12.54 mmol). After two hours the reaction was quenched with a 10% ammonium chloride solution and the organic portion was washed with 5% sodium bicarbonate, water, saturated sodium chloride solution, dried over magnesium sulfate, filtered and concentrated to give a yellow oil. Purification by flash chromatography (10% ether/pet. ether) yielded the desired aldehyde.

$^1$H NMR (CDCl$_3$): 9.95 (s, 1H); 8.25 (s, 1H); 6.98 (s, 1H); 0.29 (s, 9H).

$^{13}$C NMR (CDCl$_3$): 184.5, 164.1, 155.3, 128.9, 116.2, −2.0.

MS exact mass calculated for $C_8H_{12}O_2Si(M+)$ 168.0607, found 168.0588.

Alternative Preparation of
5-Trimethylsilyl-3-furaldehyde n-Butyl lithium (a 1.6M solution in hexane, 31.0 ml, 49.7 mmol) was added dropwise to a solution of morpholine (4.33 ml, 49.7 mmol; freshly distilled from barium oxide) in tetrahydrofuran at −78° under argon. After 15 minutes, a solution of 5-bromo-3-furaldehyde (7.5 g, 49.7 mmol) in tetrahydrofuran was added dropwise. Stirring was continued for 30 min. and n-butyl lithium (a 1.6M solution in hexane; 46.6 ml, 74.5 mmol) was added dropwise. After 1 hour at −78°, chlorotrimethylsilane (18.9 ml, 149 mmol) was added and stirring continued while the cooling bath attained room temperature. The reaction mixture was quenched with 10% hydrochloric acid and the phases were separated. The aqueous phase was stirred, in the presence of ethyl ether (30 ml), with 10% hydrochloric acid at 0° C. for ½ hour. The organic phases were combined, washed (brine), dried (magnesium sulfate) and evaporated down. The residue was distilled under vacuum to give the title aldehyde as a colorless oil b.p. 48°-50°/0.25 torr.

Still Another Alternative Preparation of
5-Trimethylsilyl-3-furaldehyde n-Butyl lithium (a 2.5M solution in hexane; 28.8 ml, 72 mmol) was added to a solution of morpholine (6.28 ml, 72 mmol) in tetrahydrofuran (700 ml) at −78° under argon. After 20 minutes, 3-furaldehyde (7.0 g, 72 mmol) was added. After another 20 minutes, sec-butyl lithium (a 1.3M solution in cyclohexane; 55.4 ml, 72 mmol) was added dropwise and stirring continued at −78° for 7 hours before trimethylsilylchloride (27 ml, 216 mmol) was added. Stirring continued overnight (14 hours) while the cooling bath was allowed to attain room temperature. The solution was poured into ice cold 10% (v/v) hydrochloric acid (200 ml) and after stirring at 0° for 10 minutes, the layers were separated. The aqueous phase was extracted with diethyl ether. All the organic phases were combined, dried (magnesium sulfate) and evaporated down to give a light brown oil, which was purified by flash chromatography on silica using 2% ethyl ether/hexane. Fractions with $R_f$ of about 0.30 (silica, 10% ethyl ether/hexane) on evaporation gave the title aldehyde as a light yellow oil, b.p. 48°–50°/0.25 torr.

4-(1-Hydroxy-4-phenylbutyl)-2-trimethylsilylfuran

To a stirred solution of 3-phenylpropylmagnesium bromide (3.3 ml of an 0.313M solution in ethyl ether, 1.03 mmol, generated from 1-bromo-3-phenylpropane and magnesium) at 0° under argon, was added dropwise 5-trimethylsilyl-3-furaldehyde (0.145 g., 0.862 mmol) in 5 ml ethyl ether. This solution was allowed to warm to room temperature, stirred for one hour, and then poured over crushed ice containing several drops of concentrated sulfuric acid. The resulting mixture was partitioned between ethyl ether and 5% sodium bicarbonate. The organic portion was washed with water, saturated sodium chloride solution, dried over magnesium sulfate, filtered and concentrated to give the desired alcohol.

$^1$H NMR (CDCl$_3$): 7.54 (s, 1H); 7.1–7.3 (m, 5H); 6.59 (s, 1H); 4.67 (t, J=6.8 Hz, 1H); 2.65 (t, J=7.5 Hz, 2H); 1.5 to 1.9 (m, 5H); 0.25 (s, 9H).

$^{13}$C NMR (CDCl$_3$): 161.5, 143.1, 142.2, 129.0, 128.4, 128.3, 125.8, 118.2, 66.8, 37.4, 35.6, 27.4, −1.7.

4-(1-Hydroxy-4-phenylbutyl)-5-hydroxy-2(5H)-furanone

A stirred solution of 4-(1-hydroxy-4-phenylbutyl)-2-trimethylsilylfuran (0.132 g., 0.458 mmol) and Rose Bengal in methanol was flushed with oxygen and cooled to −78°. The solution was subsequently irradiated with a 150 Watt flood lamp while under a constant, positive pressure of oxygen until starting material was no longer visible by TLC. The solution was warmed to room temperature, concentrated to a red oil, and purified by flash chromatography (silica, 60% ethyl acetate/hexane) to give the desired hydroxybutenolide.

$^1$H NMR (mixture of diasteriomers), (d$^6$-acetone): 7.3 to 7.1 (m, 5H); 6.86 (broad s, 1H); 6.24 (broad s, 0.3H); 6.13 (broad s, 0.7H); 6.00 (s, 1H); 4.65 (broad s, 1.4H); 4.52 (broad s, 0.6H); 2.75 to 2.55 (m, 2H); 2.0 to 1.6 (m, 4H).

$^{13}$C NMR (mixture of diasteriomers), (d$^6$-acetone): 173.7, 170.8, 143.1, 129.14 and 129.09, 129.02 and 128.96, 126.45, 117.7 and 117.4, 98.9 and 98.2, 68.2 and 67.3, 36.13 and 36.06, 35.6 and 35.2, 27.9 and 27.6 m/z Calculated for C$_{14}$H$_{17}$O$_4$ (M+H)$^+$: 249.1127; obtained (EI+): 249.1131

EXAMPLE 2

4-(1-Hydroxy-5-methyl-4-hexenyl)-2-trimethylsilylfuran

To a stirred solution of 4-methyl-3-pentenylmagnesium bromide (0.74 mmol, prepared from 0.74 mmol 5-bromo-2-methyl-2-pentene and 1.46 mmol magnesium) in two ml anhydrous ethyl ether at 0° under argon was added dropwise 5-trimethylsilyl-3-furaldehyde (0.124 g., 0.74 mmol) in 1.5 ml ethyl ether. This solution was allowed to warm to room temperature, stirred for 30 minutes, and then poured over crushed ice containing several drops of concentrated sulfuric acid. The resulting mixture was partitioned between ethyl ether and 5% sodium bicarbonate. The organic portion was washed with water, saturated sodium chloride, dried over magnesium sulfate, filtered and concentrated to give a colorless oil. This material was purified by flash chromatography (silica, 10% ethyl acetate/hexane) to give the desired alcohol.

$^1$H NMR (CDCl$_3$): 7.54 (s, 1H); 6.62 (s, 1H); 5.14 (broad t, J=6.5 Hz, 1H); 4.64 (t, J=6.5 Hz, 1H); 2.0 to 2.15 (m, 2H); 1.94 (s, 1H); 1.70 to 1.85 (m, 2H); 1.69 (s, 3H); 1.59 (s, 3H); 0.25 (s, 9H).

$^{13}$C NMR (CDCl$_3$): 161.3, 143.1, 132.2, 129.0, 123.7, 118.3; 66.5, 37.8, 25.7, 24.3, 17.6, −1.7.

m/z Calculated for C$_{14}$H$_{24}$O$_2$Si: 252.1546; obtained (EI+): 252.1544.

4-(1-Acetoxy-5-methyl-4-hexenyl)-2-trimethylsilylfuran

A solution of 4-(1-hydroxy-5-methyl-4-hexenyl)-2-trimethylsilylfuran (0.074 g., 0.293 mmol), acetic anhydride (1 ml, excess), and pyridine (3 to 4 drops, excess) was stirred at room temperature until no starting material remained (as monitored by TLC). The reaction mixture was then partitioned between ethyl ether and a 5% ammonium chloride solution. The organic portion was washed repeatedly with saturated sodium bicarbonate solution, twice with aqueous cupric sulfate solution, water, saturated sodium chloride solution, dried over magnesium sulfate, filtered and concentrated to give a pale yellow oil. This material was further purified by flash chromatography (silica, 8% ethyl ether/petroleum ether) to give the desired acetate.

$^1$H NMR (CDCl$_3$): 7.52 (s, 1H); 6.52 (s, 1H); 5.68 (t, J=6.8 Hz, 1H); 5.02 (broad t, J=6.8 Hz, 1H); 2.0 to 1.65 (m, 4H); 1.96 (s, 3H); 1.60 (s, 3H); 1.48 (s, 3H); 0.17 (s, 9H).

$^{13}$C NMR (CDCl$_3$): 170.5, 161.2, 144.6, 132.4, 124.8, 123.1, 118.7, 68.1, 34.8, 25.7, 24.1, 21.3, 17.6, −1.7.

m/z Calculated for C$_{16}$H$_{26}$O$_3$Si: 294.1651; obtained (EI+): 294.1653.

4-(1-Acetoxy-5-methyl-4-hexenyl)-5-hydroxy-2(5H)-furanone

A stirred solution of 4-(1-acetoxy-5-methyl-4-hexenyl)-2-trimethylsilylfuran (0.072 g., 0.245 mmol) and Rose Bengal (trace) in methanol was flushed with oxygen and cooled to −78°. The solution was subsequently irradiated with a 150 Watt flood lamp while under a constant positive pressure of oxygen until starting material was no longer visible by TLC. The solution was warmed to room temperature, concentrated to a red oil, and purified by flash chromatography (silica, 40% ethyl acetate/hexane) to give the desired hydroxybutenolide.

$^1$H NMR (mixture of diasteriomers), (CDCl$_3$): 6.15 (d, J=9.4 Hz, 0.3H); 6.0 to 5.85 (m, 1.7H); 5.35 to 5.45 (m, 1H); 5.20 (d, J=10.1 Hz, 0.7H); 4.95 to 5.05 (m, 1.3H); 2.15 to 1.95 (m, 2H); 2.10 (s, 2H); 2.07 (s, 1H); 1.90 to 1.70 (m, 2H); 1.65 (s, 3H); 1.54 (s, 3H).

$^{13}$C NMR (mixture of diasteriomers), (CDCl$_3$); 171.2 and 170.7, 170.3 and 170.0, 167.1 and 166.6, 133.7 and 133.4, 122.2 and 121.9, 119.1 and 118.3, 98.0 and 97.9, 69.3 and 68.8, 33.1 and 32.9, 25.6, 23.6 and 23.4, 20.8, 18.0 and 17.7.

m/z Calculated for $C_{13}H_{19}O_5$ (MH+): 255.1232; obtained (CI+): 255.1232.

EXAMPLE 3

4-[1-Hydroxy-5-methyl-7-(2,6,6-trimethylcyclohex-1-enyl)-4-heptenyl]-2-trimethylsilylfuran To a stirred solution of 4-methyl-6-(2,6,6-trimethylcyclohex-1-enyl)-3-hexenylmagnesium bromide (0.70 mmol, prepared from 0.21 g., 0.70 mmol 1-bromo-4-methyl-6-(2,6,6-trimethylcyclohex-1-enyl)-3-hexene and 2.1 mmol magnesium, with a catalytic amount of 1,2-dibromoethane as initiator), in one ml ethyl ether at 0° under argon was added dropwise 5-trimethylsilyl-3-furaldehyde (0.13 g., 0.77 mmol) in one ml ether. This solution was allowed to warm to room temperature, stirred for 30 minutes, and then poured over crushed ice containing several drops of hydrochloric acid. The resulting mixture was partitioned between ethyl ether and 5% sodium bicarbonate. The organic portion was washed with water, saturated sodium chloride, dried over magnesium sulfate, filtered and concentrated to give a colorless oil. This material was purified by flash chromatography (silica, 20% ethyl ether/hexane) to give the desired alcohol.

$^1$H NMR (CDCl$_3$): 7.57 (s, 1H); 6.63 (s, 1H); 5.18 (t, J=7.2 Hz, 1H); 4.66 (t, J=7.2 Hz, 1H); 2.0 to 2.2 (m, 5H); 1.7 to 2.0 (m, 6H); 1.5 to 1.7 (m, 2H); 1.64 (s, 3H); 1.61 (s, 3H); 1.4 to 1.5 (m, 2H); 1.00 (s, 6H); 0.25 (s, 9H).

$^{13}$C NMR (CDCl$_3$): 161.3, 143.1, 137.01, 137.00, 129.0, 126.9, 122.9, 118.3, 66.6, 40.3, 39.8, 37.8, 34.9, 32.7, 28.6, 27.9, 24.3, 19.8, 19.5, 16.0, −1.7.

m/z Calculated for $C_{24}H_{40}O_2Si$: 388.2798; obtained (EI+): 388.2783.

4-[1-Acetoxy-5-methyl-7-(2,6,6-trimethylcyclohex-1-enyl)-hept-4-ene]-2-trimethylsilylfuran A stirred solution of 4-[1-hydroxy-5-methyl-7-(2,6,6-trimethylcyclohex-1-enyl)-hept-4-ene]-2-trimethylsilylfuran (0.134 g., 0.345 mmol), acetic anhydride (1ml, excess), and pyridine (3 to 4 drops, excess) was stirred at room temperature until no starting material remained (as monitored by TLC). The reaction mixture was then partitioned between ethyl ether and a 5% ammonium chloride solution. The organic portion was washed repeatedly with saturated sodium bicarbonate solution, twice with aqueous cupric sulfate solution, water, saturated sodium chloride solution, dried over magnesium sulfate, filtered and concentrated to give a pale yellow oil. This material was further purified by flash chromatography (silica, 20% ethyl acetate/hexane) to give the desired acetate.

$^1$H NMR (CDCl$_3$): 7.60 (s, 1H); 6.60 (s, 1H); 5.77 (t, J=7.2 Hz, 1H); 5.14 (broad t, J=7.2 Hz, 1H); 2.1 to 1.7 (m, 13H); 1.65 to 1.50 (m, 8H); 1.45 to 1.37 (m, 2H); 1.00 (s, 6H); 0.25 (s, 9H).

$^{13}$C NMR (CDCl$_3$): 170.4, 161.1, 144.5, 137.1, 137.0, 126.9, 124.8, 122.3, 118.6, 68.1, 40.2, 39.8, 34.9, 34.8, 32.7, 32.6, 28.6, 27.8, 24.0, 21.3, 19.8, 19.5, 15.9, −1.7.

m/z Calculated for $C_{24}H_{38}OSi$ (M+—HOAc): 370.2692; obtained (EI+): 370.2700.

4-[1-Acetoxy-5-methyl-7-(2,6,6-trimethylcyclohex-1-enyl)hept-4-ene]-5-hydroxy-2(5H)-furanone A stirred solution of 4-[1-acetoxy-5-methyl-7-(2,6,6-trimethylcyclohex-1-enyl)-hept-4-ene]-2-trimethylsilylfuran (0.119 g., 0.276 mmol) and Rose Bengal (trace) in methanol was flushed with oxygen and cooled to −78°. The solution was subsequently irradiated with a 150 Watt flood lamp while under a constant pressure of oxygen until starting material was no longer visible by TLC. The solution was warmed to room temperature, concentrated to a red oil, and purified by flash chromatography (silica, 30% ethyl acetate/hexane) to give the captioned compound.

$^1$H NMR (mixture of diasteriomers) (CDCl$_3$): 6.2 (s, 0.4H); 6.15 to 5.95 (m, 1.6H); 5.6 to 5.4 (m, 1H); 5.3 (broad s, 1H); 5.2 to 5.0 (m, 1H); 2.3 to 1.75 (m, 13H); 1.75 to 1.3 (m, 10H); 0.99 (s, 6H).

$^{13}$C NMR (mixture of diasteriomers) (CDCl$_3$): 171.1 and 170.7, 170.3 and 170.1, 167.1 and 166.7, 138.2 and 137.9, 136.9 and 136.8, 127.0, 121.5 and 121.2, 119.0 and 118.3, 98.1 and 98.0, 69.4 and 68.9, 40.1, 39.7, 34.9, 33.0, 32.7, 28.5, 27.7 and 27.2, 23.5, 23.4 and 23.3, 20.8, 19.8 and 19.5, 16.0.

m/z Calculated for $C_{21}H_{30}O_3$ (M+—HOAc): 330.2195; obtained (EI+): 330.2203.

EXAMPLE 4

5-Cyclohexylpentanol

To a solution of 5-phenylpentanol (2.21 g., 13.5 mmol) in ten ml glacial acetic acid was added amorphous platinum oxide (0.40 g., 1.76 mmol, oxygen activated). This mixture was subjected to three atm. of hydrogen with agitation (Parr hydrogenator) at room temperature for four hours. The reaction mixture was diluted with ethyl ether, filtered through celite, washed repeatedly with saturated sodium bicarbonate, followed by water and saturated sodium chloride solution. The organic portion was filtered, dried over magnesium sulfate, filtered and concentrated to give the desired alcohol.

$^1$H NMR (CDCl$_3$): 3.60 (t, J=7.1 Hz, 2H); 2.30 (s, 1H); 1.75 to 1.8 (m, 19H).

$^{13}$C NMR (CDCl$_3$): 62.8, 37.6, 37.4, 33.4, 32.7, 26.7, 26.6, 26.4, 26.0.

1-Bromo-5-cyclohexylpentane

To a stirred solution of 5-cyclohexylpentanol (1.74 g., 10.25 mmol) and pyridine (0.94 g., 11.1 mmol) at 0° under argon was added phosphorus tribromide (1.21 g., 4.5 mmol) dropwise. The reaction mixture became viscous, therefore 25 ml tetrahydrofuran was added. This mixture was stirred for 1.5 hours at room temperature, then partitioned between ethyl ether and 5% aqueous hydrochloric acid. The organic portion was washed with a 5% sodium bicarbonate solution, water, saturated sodium chloride solution, dried over magnesium sulfate, filtered and concentrated to give a dark yellow oil. Purification by flash chromatography (silica, hexane) yielded the desired alkyl halide.

$^1$H NMR (CDCl$_3$): 3.39 (t, J=7.1 Hz, 2H); 1.85 (m, 2H); 1.56 to 1.77 (m, 5H); 1.11 to 1.45 (m, 10H); 0.78 to 0.96 (m, 2H).

$^{13}$C NMR (CDCl$_3$): 37.5, 37.2, 33.8, 33.3, 32.8, 28.4, 26.7, 26.4, 25.9.

4-(6-Cyclohexyl-1-hydroxyhexyl)-2-trimethylsilylfuran

To a stirred solution of 5-cyclohexylpentyl-magnesium bromide (1.32 mmol, prepared from 0.31 g., 1.32 mmol 1-bromo-5-cyclohexylpentane and 2.88 mmol magnesium, with a catalytic amount of 1,2-dibromoethane as initiator), in 2.5 ml anhydrous tetrahydrofuran at 0° under argon was added dropwise 5-trimethylsilyl-3-furaldehyde (0.23 g., 1.40 mmol) in 2.5 ml tetrahydrofuran. This solution was allowed to warm to room temperature, stirred for one hour, and then poured over crushed ice containing several drops of concentrated sulfuric acid. The resulting mixture was partitioned between ethyl ether and 5% sodium bicarbonate. The organic portion was washed with water, saturated sodium chloride, dried over magnesium sulfate, filtered and concentrated to give a colorless oil (0.173 g.). This material was purified by flash chromatography (silica, 90% petroleum ether/ethyl ether) to give the desired alcohol.

$^{13}$H NMR (CDCl$_3$): 7.55 (s, 1H); 6.62 (s, 1H); 4.63 (t, J=7.1 Hz, 1H); 1.85 (s, 1H); 1.5–1.8 (m, 7H); 1.0–1.5 (m, 12H); 0.75 to 0.92 (m, 2H); 0.25 (s, 9H).

m/z Calculated for C$_{19}$H$_{34}$O$_2$Si: 322.2328; obtained (EI+): 322.2317.

4-(1-Acetoxy-6-cyclohexylhexyl)-2-trimethylsilylfuran

A stirred solution of 4-(6-cyclohexyl-1-hydroxyhexyl)-2-trimethylsilylfuran (0.065 g., 0.205 mmol), acetic anhydride (1 ml, excess), and pyridine (3 to 4 drops, excess) was stirred at room temperature until no starting material remained (as monitored by TLC). The reaction mixture was then partitioned between ethyl ether and a 5% ammonium chloride solution. The organic portion was washed repeatedly with saturated sodium bicarbonate solution, twice with aqueous cupric sulfate solution, water, saturated sodium chloride solution, dried over magnesium sulfate, filtered and concentrated to give a pale yellow oil. This material was further purified by flash chromatography (silica, 5% ethyl ether/hexane) to give the desired acetate.

$^1$H NMR (CDCl$_3$): 7.59 (s, 1H); 6.59 (s, 1H); 5.76 (t, J=7.2 Hz, 1H); 2.04 (s, 3H); 1.9 to 1.5 (m, 7H); 1.45 to 1.0 (m, 12H); 0.95 to 0.75 (m, 2H); 0.25 (s, 9H).

m/z Calculated for C$_{21}$H$_{36}$O$_3$Si: 364.2434; obtained (EI+): 364.2434.

4-(1-Acetoxy-6-cyclohexylhexyl)-5-hydroxy-2-(5H)-furanone

A stirred solution of 4-(1-acetoxy-6-cyclohexylhexyl)-2-trimethylsilylfuran (0.072 g., 0.198 mmol) and Rose Bengal (trace) in methanol was flushed with oxygen and cooled to −78°. The solution was subsequently irradiated with a 150 Watt flood lamp while under a constant pressure of oxygen until starting material was no longer visible by TLC. The solution was warmed to room temperature, concentrated to a red oil, and purified by flash chromatography (silica, 40% ethyl ether/hexane) to give the desired hydroxybutenolide.

$^1$H NMR (mixture of diasteriomers) (CDCl$_3$): 6.20 (s, 0.4H); 6.1 to 5.95 (m, 1.6H); 5.55 to 5.45 (m, 1H); 5.35 (broad s, 0.6H); 5.17 (broad s, 0.4H); 2.15 (s, 1.8H), 2.12 (s, 1.2H); 1.95 to 1.55 (m, 7H); 1.55 to 1.05 (m, 12H); 0.95 to 0.75 (m, 2H).

$^{13}$C NMR (mixture of diasteriomers) (CDCl$_3$): 171.2 and 170.8, 170.4 and 170.0, 167.2 and 166.6, 119.1 and 118.3, 98.1 and 98.0, 69.8 and 69.2, 37.5, 37.3, 33.4, 33.0, 29.4, 26.7, 26.5, 26.4, 24.9, 20.8.

m/z Calculated for C$_{18}$H$_{29}$O$_5$ (MH+): 325.2015; obtained (EI+): 325.2030.

EXAMPLE 5

6-(Benzo[b]thien-2-yl)-1-bromohexane

To a stirred solution of benzo[b]thiophene (1.92 g., 14.3 mmol) in 90 ml anhydrous tetrahydrofuran at −10° to 0° under argon was added n-butyllithium (7.8 ml of a 1.86M solution in hexane). After two hours, this solution was transferred dropwise into a stirred, 0° solution of 1,6-dibromohexane (6.5 ml, 0.043 mol) in 250 ml tetrahydrofuran. The solution was warmed to room temperature, stirred for 15 hours, quenched with water and concentrated. The residue was acidified and partitioned between ethyl ether and water. The aqueous portion was extracted twice with ether, and the combined organic portions were washed with water, saturated sodium chloride solution, dried over magnesium sulfate, filtered and concentrated to give a brown oil. Excess benzo[b]thiophene and 1,6-dibromohexane were removed by bulb to bulb distillation (85° to 90°/0.1 mm) to leave a dark brown syrup. This material was purified by flash chromatography (silica, hexane to 5% ethyl ether/hexane) to give the desired alkyl halide.

$^1$H NMR (CDCl$_3$): 7.77 (d, J=7.6 Hz, 1H); 7.67 (d, J=7.2 Hz, 1H); 7.29 (m, 2H); 7.00 (s, 1H); 3.41 (t, J=6.8 Hz, 2H); 2.92 (t, J=6.5 Hz, 2H); 1.85 (m, 4H); 1.5 (m, 4H).

$^{13}$C NMR (CDCl$_3$): 146.4, 140.2, 139.3, 124.0, 123.4, 122.7, 122.1, 120.5, 33.8, 32.7, 30.9, 30.6, 28.2, 27.9.

m/z Calculated for C$_{14}$H$_{17}$BrS: 296.0234; obtained (EI+): 296.0220.

4-(7-Benzo[b]thien-2-yl-1-hydroxyheptyl)-2-trimethylsilylfuran

To a stirred solution of 6-(benzo[b]thien-2-yl)hexylmagnesium bromide (1.22 mmol, prepared from 1.22 mmol 6-(benzo[b]thien-2-yl)-1-bromohexane and 2.44 mmol magnesium, initiated with a catalytic amount of 1,2-dibromoethane) in 1.5 ml tetrahydrofuran at 0° under argon was added dropwise 5-trimethylsilyl-3-furaldehyde (0.167 g., 0.99 mmol) in 1 ml tetrahydrofuran. This solution was allowed to warm to room temperature, stirred for 30 minutes, and then quenched with a 5% ammonium chloride solution. The resulting mixture was partitioned between ethyl ether and 5% sodium bicarbonate. The organic portion was washed with water, saturated sodium chloride, dried over magnesium sulfate, filtered and concentrated to give a pale yellow oil. This material was purified by flash chromatography (silica, 100% hexane to 20% ethyl acetate/hexane) to give the desired alcohol.

$^1$H NMR (CDCl$_3$): 7.73 (d, J=7.7 Hz, 1H); 7.63 (d, J=7.9 Hz, 1H); 7.52 (s, 1H); 7.21 to 7.33 (m, 2H); 6.95 (s, 1H); 6.60 (s, 1H); 4.59 (t, J=6.5 Hz, 1H); 2.86 (t, J=7.4 Hz, 2H); 1.83 (s, 1H); 1.63 to 1.83 (m, 4H); 1.27 to 1.52 (m, 6H); 0.24 (s, 9H).

$^{13}$C NMR (CDCl$_3$): 161.3, 146.6, 143.0, 140.2, 139.2, 129.2, 123.9, 123.3, 122.6, 122.0, 120.4, 118.2, 66.8, 37.8, 31.0, 30.7, 29.1, 28.9, 25.6, −1.7.

m/z Calculated for C$_{22}$H$_{30}$O$_2$SSi: 386.1736; obtained (EI+): 386.1728.

4-(1-Acetoxy-7-benzo[b]thien-2-ylheptyl)-2-trimethylsilylfuran

A stirred solution of 4-(7-benzo[b]thien-2-yl-1-hydroxyheptyl)-2-trimethylsilylfuran (0.102 g., 0.246 mmol), acetic anhydride (1 ml, excess), and pyridine (3 to 4 drops, excess) was stirred at room temperature until no starting material remained (as monitored by TLC). The reaction mixture was then partitioned between ethyl ether and a 5% ammonium chloride solution. The organic portion was washed repeatedly with saturated sodium bicarbonate solution, twice with aqueous cupric sulfate solution, water, saturated sodium chloride solution, dried over magnesium sulfate, filtered and concentrated to give a pale yellow oil. This material was further purified by flash chromatography (silica, 5% to 10% ethyl ether/petroleum ether) to give the desired acetate.

$^1$H NMR (CDCl$_3$): 7.72 (d, J=8.1 Hz, 1H); 7.63 (d, J=7.5 Hz, 1H); 7.58 (s, 1H); 7.4 to 7.15 (m, 2H); 6.95 (s, 1H); 6.59 (s, 1H); 5.77 (t, J=7.1 Hz, 1H); 2.85 (t, J=7.5 Hz, 2H); 2.02 (s, 3H); 2.0 to 1.65 (m, 4H); 1.5 to 1.2 (m, 6H); 0.24 (s, 9H).

$^{13}$C NMR (CDCl$_3$): 170.3, 161.1, 146.5, 144.4, 140.2, 139.2, 124.9, 123.9, 123.3, 122.6, 122.0, 120.4, 118.6, 68.4, 34.7, 30.9, 30.6, 28.9, 28.8, 25.3, 21.2, −1.7.

m/z Calculated for C$_{24}$H$_{32}$O$_3$SSi: 428.1841; obtained (EI+): 428.1843.

4-(1-Acetoxy-7-benzo[b]thien-2-ylheptyl)-5-hydroxy-2(5H)-furanone

A stirred solution of 4-(1-acetoxy-7-benzo[b]thien-2-ylheptyl)-2-trimethylsilylfuran (0.097 g., 0.226 mmol) and Rose Bengal (trace) in acetone was flushed with oxygen and cooled to −78°. The solution was subsequently irradiated with a 150 Watt flood lamp while under a constant pressure of oxygen until starting material was no longer visible by TLC. The solution was warmed to room temperature, concentrated to a red oil, and purified by flash chromatography (silica, 50% ethyl acetate/hexane) to give the desired hydroxybutenolide.

$^1$H NMR (CDCl$_3$): 7.74 (d, J=7.3 Hz, 1H); 7.64 (d, J=7.2 Hz, 1H); 7.4 to 7.15 (m, 2H); 6.2 to 5.9 (m, 2H); 5.7 to 5.3 (m, 2H); 2.87 (t, J=7.2 Hz, 2H); 2.09 (s, 3H); 1.95 to 1.60 (m, 4H); 1.55 to 1.15 (m, 6H).

$^{13}$C NMR (CDCl$_3$): 170.8, 170.2, 166.8, 146.4, 140.1, 139.2, 124.0, 123.3, 122.6, 122.0, 120.5, 118.5, 98.0, 69.4, 32.8, 30.8, 30.6, 28.7, 28.6, 24.7, 20.7.

m/z Calculated for C$_{21}$H$_{24}$O$_5$S: 388.1344; obtained (EI+): 388.1354.

EXAMPLE 6

4-(1-Cyclohexyl-1-hydroxymethyl)-2-trimethylsilylfuran

To a stirred solution of cyclohexylmagnesium chloride (0.24 ml, 0.484 mmol, 2.0M solution in ethyl ether) under argon at 0°, was added dropwise 5-trimethylsilyl-3-furaldehyde (0.072 g., 0.44 mmol) in 5 ml of dry tetrahydrofuran. This solution was allowed to warm to room temperature, stirred for 30 minutes and poured over crushed ice containing several drops of concentrated sulfuric acid. The resulting mixture was partitioned between ethyl ether and 5% sodium bicarbonate. The organic portion was washed with water, saturated sodium chloride solution, dried over magnesium sulfate, filtered and concentrated to give a colorless oil. This material was purified by flash chromatography (silica, 10% ethyl ether/pentane) to yield the desired alcohol.

$^1$H NMR (CDCl$_3$): 7.51 (s, 1H); 6.58 (s, 1H); 4.34 (d, J=6.7 Hz, 1H); 1.9 to 2.1 (m, 2H); 1.4 to 1.9 (m, 4H); 0.8 to 1.4 (m, 6H); 0.25 (s, 9H).

$^{13}$C NMR (CDCl$_3$): 161.0, 143.6, 127.7, 118.5, 71.6, 44.0, 29.1, 28.7, 26.4, 26.0, 25.9, −1.7.

m/z Calculated for C$_{14}$H$_{24}$O$_2$Si: 252.1546; obtained (EI+): 252.1549.

4-(1-Acetoxy-1-cyclohexylmethyl)-2-trimethylsilylfuran

A solution of 4-(1-cyclohexyl-1-hydroxymethyl)-2-trimethylsilylfuran (0.093 g., 0.37 mmol), acetic anhydride (excess), and pyridine (3 to 4 drops) was stirred at room temperature until no starting material remained (as monitored by TLC). The reaction mixture was then partitioned between ethyl ether and a 5% ammonium chloride solution. The organic portion was washed repeatedly with saturated sodium bicarbonate solution, twice with aqueous cupric sulfate solution, water, saturated sodium chloride solution, dried over magnesium sulfate, filtered and concentrated to give a pale yellow oil. This material was further purified by flash chromatography (silica, 5% ethyl ether/n-pentane) to give the desired acetate.

$^1$H NMR (CDCl$_3$): 7.55 (s, 1H); 6.54 (s, 1H); 5.55 (d, J=7.5 Hz, 1H); 2.04 (s, 3H); 1.9 to 1.5 (m, 6H); 1.30 to 0.85 (m, 5H); 0.25 (s, 9H).

$^{13}$C NMR (CDCl$_3$): 170.4, 160.9, 144.7, 123.6, 118.8, 72.7, 41.9, 28.9, 26.3, 25.8, 21.2, −1.7.

m/z Calculated for C$_{16}$H$_{26}$O$_3$Si: 294.1651; Obtained (EI+): 294.1656.

4-(1-Acetoxy-1-cyclohexylmethyl)-5-hydroxy-2(5H)-furanone

A stirred solution of 4-(1-acetoxy-1-cyclohexylmethyl)-2-trimethylsilylfuran (0.073 g., 0.248 mmol) and Rose Bengal (trace) in methanol was flushed with oxygen and cooled to −78°. The solution was subsequently irradiated with a 150 Watt flood lamp while under a constant positive pressure of oxygen until starting material was no longer visible by TLC. The solution was warmed to room temperature, concentrated to a red oil, and purified by flash chromatography (silica, 30% ethyl acetate/hexane) to give the desired hydroxybutenolide.

$^1$H NMR (mixture of diasteriomers) (CDCl$_3$): 6.20 (s, 0.03H); 6.1 to 5.9 (m, 1.7H); 5.7 (broad s, 0.7H); 5.6 (broad s, 0.3H); 5.34 (d, J=5.4 Hz, 0.3H); 5.26 (d, J=5.4 Hz, 0.7H); 2.15 (s, 2H); 2.11 (s, 1H); 1.95 to 1.6 (m, 6H); 1.45 to 1.0 (m, 5H).

$^{13}$C NMR (mixture of diasteriomers) (CDCl$_3$): 171.4 and 170.9, 170.3 and 170.0, 166.5 and 165.4, 119.9 and 119.1, 98.54 and 98.46, 73.6 and 73.5, 40.7 and 40.2, 29.4 and 28.9, 27.6 and 27.0, 25.8 and 25.7, 20.7.

m/z Calculated for C$_{13}$H$_{18}$O$_5$: 254.1154; obtained (EI+): 254.1177.

EXAMPLE 7

4-(1-Hydroxy-1-phenylmethyl)-2-trimethylsilylfuran

To a stirred solution of phenylmagnesium bromide (0.41 ml, 1.27 mmol, 3.1M solution in ethyl ether) under argon at 0°, was added dropwise 5-trimethylsilyl-3-furaldehyde (0.194 g., 1.15 mmol) in 2 ml tetrahydrofuran. This solution was allowed to warm to room temperature, stirred for 30 minutes, and poured over crushed ice containing several drops of concentrated sulfuric acid. The resulting mixture was partitioned between ethyl ether and 5% sodium bicarbonate. The organic portion was washed with water, saturated sodium chloride solution, dried over magnesium sulfate, filtered and concentrated to give a colorless oil. This material was purified by flash chromatography (silica, 10% ethyl acetate/hexane) to give the desired alcohol.

$^1$H NMR (CDCl$_3$): 7.1 to 7.4 (m, 6H); 6.54 (s, 1H); 5.70 (s, 1H); 2.44 (s, 1H); 0.22 (s, 9H).

$^{13}$C NMR (CDCl$_3$): 161.5, 144.0, 143.2, 128.8, 128.4, 127.6, 126.3, 118.9, 69.3, −1.7.

m/z Calculated for C$_{14}$H$_{18}$O$_2$Si: 246.1076; obtained (EI+): 246.1074.

4-(1-Acetoxy-1-phenylmethyl)-2-trimethylsilylfuran

A stirred solution of 4-(1-hydroxy-1-phenylmethyl)-2-trimethylsilylfuran (0.21 g., 0.852 mmol), acetic anhydride (1 ml, excess), and pyridine (3 to 4 drops, excess) was stirred at room temperature until no starting material remained (as monitored by TLC). The reaction mixture was then partitioned between ethyl ether and a 5% ammonium chloride solution. The organic portion was washed repeatedly with saturated sodium bicarbonate solution, twice with aqueous cupric sulfate solution, water, saturated sodium chloride solution, dried over magnesium sulfate, filtered and concentrated to give a pale yellow oil. This material was further purified by flash chromatography (silica, 8% ethyl ether/n-pentane) to give the desired acetate.

$^1$H NMR (CDCl$_3$): 7.5 to 7.25 (m, 6H); 6.81 (s, 1H); 6.53 (s, 1H); 2.10 (s, 3H); 0.22 (s, 9H).

$^{13}$C NMR (CDCl$_3$): 170.0, 161.5, 145.0, 139.5, 128.4, 128.0, 126.8, 125.4, 119.2, 70.3, 21.2, −1.8.

m/z Calculated for C$_{16}$H$_{20}$O$_3$Si: 288.1182; obtained (EI+): 288.1182.

4-(1-Acetoxy-1-phenylmethyl)-5-hydroxy-2(5H)-furanone

A stirred solution of 4-(1-acetoxy-1-phenyl-methyl)-2-trimethylsilylfuran (0.15 g., 0.555 mmol) and Rose Bengal (trace) in methanol was flushed with oxygen and cooled to −78°. The solution was subsequently irradiated with a 150 Watt flood lamp while under a constant pressure of oxygen until starting material was no longer visible by TLC. The solution was warmed to room temperature, concentrated to a red oil, and purified by flash chromatography (silica, 30% to 40% ethyl acetate/hexane) to give the desired hydroxybutenolide.

$^1$H NMR (mixture of diasteriomers) (CDCl$_3$): 7.31 (s, 5H); 6.51 to 6.48 (m, 1H); 6.2 to 6.08 (m, 1H); 5.75 to 5.5 (m, 2H); 2.07 (s, 1.5H); 2.05 (s, 1.5H).

$^{13}$C NMR (mixture of diasteriomers) (CDCl$_3$): 170.6 and 170.4, 170.0 and 169.9, 166.2 and 166.0, 135.6 and 135.0, 129.4 and 129.1, 128.8, 127.6 and 127.3, 120.8 and 117.1, 98.0 and 97.5, 71.8 and 70.6, 20.8.

m/z Calculated for C$_{11}$H$_8$O$_3$ (M+−HOAc): 188.0473; obtained (EI+): 188.0473.

EXAMPLE 8

4-(1-Hydroxypentyl)-2-trimethylsilylfuran

To a stirred solution of 5-trimethylsilyl-3-furaldehyde (0.134 g., 0.796 mmol) in 15 ml tetrahydrofuran at −78° under argon was added n-butyllithium (0.836 mmol in hexane). The reaction mixture was allowed to warm to room temperature, stirred for 30 minutes and quenched with a 5% ammonium chloride solution. The resulting mixture was partitioned between ethyl ether and 5% sodium bicarbonate solution. The organic portion was washed with water, saturated sodium chloride solution, dried over magnesium sulfate, filtered and concentrated to give the desired alcohol. This material was carried on without further purification.

$^1$H NMR (CDCl$_3$): 7.55 (s, 1H); 6.61 (s, 1H); 4.62 (t, J=7.2 Hz, 1H); 1.65 to 1.95 (m, 3H); 1.15 to 1.45 (m, 4H); 0.70 to 0.98 (m, 3H); 0.24 (s, 9H).

$^{13}$C NMR (CDCl$_3$): 160, 143, 128, 118, 66.3, 36.4, 26.5, 22.0, 18.5, −1.7.

4-(1-Acetoxypentyl)-2-trimethylsilylfuran

A stirred solution of 4-(1-hydroxypentyl)-2-trimethylsilylfuran (approx. 0.80 mmol), acetic anhydride (1 ml, excess), and pyridine (3 to 4 drops, excess) was stirred at room temperature until no starting material remained (as monitored by TLC). The reaction mixture was then partitioned between ethyl ether and a 5% ammonium chloride solution. The organic portion was washed repeatedly with saturated sodium bicarbonate solution, twice with aqueous cupric sulfate solution, water, saturated sodium chloride solution, dried over magnesium sulfate, filtered and concentrated to give a pale yellow oil. This material was further purified by flash chromatography (silica, 10% ethyl ether/petroleum ether) to give the desired acetate.

$^1$H NMR (CDCl$_3$): 7.59 (s, 1H); 6.58 (s, 1H); 5.77 (t, J=7.2 Hz, 1H); 2.05 (s, 3H); 1.95 to 1.7 (m, 2H); 1.4 to 1.2 (m, 4H); 0.90 (t, J=6.8 Hz, 3H); 0.25 (s, 9H).

$^{13}$C NMR (CDCl$_3$): 170.5, 160.8, 144.4, 125.0, 118.6, 68.6, 34.5, 27.7, 22.4, 21.3, 14.0, −1.7.

m/z Calculated for C$_{14}$H$_{24}$O$_3$Si: 268.1495; obtained (EI+): 268.1509.

4-(1-Acetoxypentyl)-5-hydroxy-2(5H)-furanone

A stirred solution of 4-(1-acetoxypentyl)-2-trimethylsilylfuran (0.110 g., 0.410 mmol) and Rose Bengal (trace) in acetone was flushed with oxygen and cooled to −78°. The solution was subsequently irradiated with a 150 Watt flood lamp while under a constant pressure of oxygen until starting material was no longer visible by TLC. The solution was warmed to room temperature, concentrated to a red oil, and purified by flash chromatography (silica, 50% ethyl ether/petroleum ether) to give the desired hydroxybutenolide.

$^1$H NMR (mixture of diasteriomers) (CDCl$_3$): 6.1 (broad s, 1H); 5.98 (s, 1H); 5.72 (broad s, 1H); 5.54 (m, 1H); 2.14 (s, 3H); 1.95 to 1.70 (m, 2H); 1.45 to 1.20 (m, 4H); 1.0 to 0.85 (m, 3H).

$^{13}$C NMR (mixture of diasteriomers) (CDCl$_3$): 170.9, 170.4, 167.0, 118.6 and 118.4, 98.1, 69.6 and 69.5, 32.5, 26.9, 22.2, 20.7, 13.7.

m/z Calculated for C$_{11}$H$_{17}$O$_5$ (MH+): 229.1076; obtained (EI+): 229.1069.

EXAMPLE 9

4-[(Acetoxy)benzo[b]thien-2-ylmethyl]-5-hydroxy-2(5H)-furanone

To a stirred solution of benzo[b]thiophene (0.193 g., 1.44 mmol) in 7 ml tetrahydrofuran at −20° under argon was added n-butyllithium (1.51 mmol in hexane). After one hour the solution was cooled to −78°, and 5-trimethylsilyl-3-furaldehyde (0.22 g., 1.31 mmol) was added dropwise in 5 ml tetrahydrofuran. The reaction mixture was allowed to warm to room temperature and then quenched with a 10% ammonium chloride solution. The organic layer was washed with a 5% sodium bicarbonate solution, water, saturated sodium chloride solution, dried over magnesium sulfate, filtered and concentrated to yield the desired alcohol as an unstable, pale yellow oil. The alcohol was treated immediately with acetic anhydride (excess) and pyridine (0.20 g., 2.6 mmol) at room temperature under argon and stirred until TLC showed no remaining starting material. The mixture was partitioned between ethyl ether and a 5% ammonium chloride solution, and the organic portion was washed repeatedly with saturated sodium bicarbonate, twice with 5% aqueous cupric sulfate solution, water, saturated sodium chloride solution, dried over magnesium sulfate, filtered and concentrated to give the acetate (also unstable) as a yellow oil. This material was taken up in oxygenated methanol and cooled to −78°. A catalytic amount of Rose Bengal was added, and while oxygen was continuously being bubbled through the solution it was irradiated with a 150 Watt flood lamp until starting material was no longer visible by TLC. The mixture was warmed to room temperature and concentrated to give a red oil. Purification by flash chromatography (0.173 g. material, silica, 70% ethyl ether/hexane) yielded the hydroxybutenolide.

$^1$H NMR (mixture of diasteriomers) (CDCl$_3$): 7.72 to 7.82 (m, 2H); 7.33 to 7.45 (m, 3H); 6.92 (s, 1H); 6.27 (s, 0.3H); 6.24 (s, 0.7H); 6.07 (s, 0.3H); 5.88 (s, 0.7H); 4.9 to 5.3 (s, 1H); 2.17 (s, 2H); 2.15 (s, 1H).

$^{13}$C NMR (mixture of diasteriomers) (CDCl$_3$): 169.9 and 169.7, 169.8 and 169.6, 164.7 and 164.4, 140.1 and 139.8, 138.7 and 138.1, 137.4, 125.5, 125.4 and 125.3, 124.9 and 124.8, 124.4 and 124.2, 122.5 and 122.45, 121.5 and 118.2, 97.5 and 97.3, 67.4 and 66.8, 20.8 and 20.75.

m/z Calculated for C$_{15}$H$_{12}$O$_5$S: 304.0405; obtained (EI+): 304.0419.

EXAMPLE 10

5-Bromo-3-furaldehyde

3-Furaldehyde (11.6 g, 121 mmol) was added dropwise to a solution of anhydrous aluminum bromide (48.1 g, 180 mmol) in dry dibromomethane (200 ml). An exothermic reaction ensued and a dark brown color developed. After 10 min, bromine (6.82 ml, 133 mmol) was added dropwise and the mixture was warmed at ca. 50° for 1h. On cooling, the mixture was poured into crushed ice and the organic layer was separated. The aqueous phase was extracted with methylene chloride. All the organic layers were combined, washed (successively with water, 5% aqueous sodium bicarbonate and brine) and filtered through celite (to assist separation) if necessary. Distillation of the dried (magnesium sulfate) extract gave 5-bromo-3-furaldehyde as a colorless oil: bp 55°/0.25 torr.

$^1$H NMR (CDCl$_3$): 6.80 (s, 1H), 8.10 (s, 1H) and 9.91 (s, 1H).

4-(1-Hydroxynonyl)-2-trimethylsilylfuran

A mixture of 1-bromooctane (1.33 g, 6.9 mmol) and magnesium turnings (174 mg, 7.3 mmol) in tetrahydrofuran (8 ml) was refluxed under argon for 60 min. After cooling to 0°, a solution of 5-bromo-3-furaldehyde (1.21 g, 6.9 mmol) in THF (1 ml) was added and conditions maintained for 60 min. The mixture was further cooled to −78° and tert-butyl lithium (a 1.7M solution in pentane, 4.26 ml, 7.3 mmol) was added dropwise, followed by chlorotrimethylsilane (2.63 ml, 20.7 mmol) after 1h. Stirring was continued overnight while the cooling bath attained room temperature. The mixture was quenched with saturated aqueous ammonium chloride, diluted with water (15 ml) and extracted with ether. Evaporation of the dried (magnesium sulfate) extract gave a brown oil, which was subjected to flash chromatography on silica using 15% ethyl ether/petroleum ether. Fractions with R$_f$ 0.2 on evaporation gave the captioned compound as a yellow oil.

$^1$H NMR (CDCl$_3$): 0.32 (s, 9H), 0.94 (t, 3H, J=7.3 Hz), 1.33 (broad s, 12H), 1.70 (br, 1H), 1.85 (m, 2H), 4.71 (t, 1H, J=6.8 Hz), 7.32 (s, 1H) and 7.63 (s, 1H).

$^{13}$C NMR (CDCl$_3$): −1.70, 14.0, 22.6, 25.4, 25.6, 25.7, 29.2 29.5, 31.8, 36.8, 37.6, 37.9, 66.7, 66.9, 110.2, 118.3, 129.2, 140.4, 143.4 and 161.2.

MS m/e (% abundance) 282 (M+, 2) (3), 249 (4), 247 (4), 182 (3), 177 (11), 175 (12), 169 (9), 167 (3) and 147 (5); exact mass calculated for C$_{16}$H$_{30}$SiO$_2$ 282.2015, found 282.2009.

4-(1-Acetoxynonyl)-2-trimethylsilylfuran

A mixture of 4-(1-hydroxynonyl)-2-trimethylsilylfuran (1.65 g, 5.9 mmol), acetic anhydride (2 ml) and pyridine (3 ml) was stirred under argon at ca. 20° for 17h. After most of the solvent was removed under high vacuum (<40°), the residue was dissolved in ether (40 ml) and washed thoroughly with aqueous copper sulfate and water. Drying (magnesium sulfate) and evaporation gave a brown oil, which was flash chromatographed on silica using 5% ethyl ether/petroleum ether. Fractions with R$_f$0.32 on evaporation afforded 4-(1-acetoxynonyl)-2-trimethyl-silylfuran as a pale yellow oil.

$^1$H NMR (CDCl$_3$): 0.26 (s, 9H), 0.89 (t, 3H, J=7.6 Hz), 1.27 (broad s, 12H), 1.90 (m, 2H), 2.06 (s, 3H), 5.78 (t, 1H, J=6.7 Hz), 6.60 (s, 1H) and 7.61 (s, 1H).

$^{13}$C NMR (CDCl$_3$): −1.73, 14.0, 21.1, 21.2, 22.6, 25.3, 25.5, 29.2, 29.2, 29.4, 31.8, 34.4, 34.8, 68.0, 68.3, 68.6, 110.5, 118.6, 125.0, 141.8, 144.4, 161.1 and 170.4.

MS m/e (% abundance) 325 (M++1, 5), 324 (21), 283 (13), 282 (56), 265 (16), 183 (27), 170 (36), 169 (41), 154 (14), 153 (13), 117 (32) and 73 (100); exact mass calculated for C$_{18}$H$_{32}$SiO$_3$ 324.2121, found 324.2115.

4-(1-Acetoxynonyl)-5-hydroxy-2(5H)-furanone

A mixture of 4-(1-acetoxynonyl)-2-trimethylsilylfuran (323 mg, 0.9 mmol) and Rose Bengal (5 mg) in THF (10 ml) was exposed to singlet oxygen for 5.5h at −78°. The residue, after solvent removal, was flash chromatographed on silica using 60% ethyl ether/petroleum ether. Fractions with R$_f$0.13 on evaporation afforded the captioned compound as colorless prisms.

mp 54°-5°.

$^1$H NMR (CDCl$_3$): 0.96 (t, 3H, J=6.7 Hz), 1.34 (broad s, 12H), 1.89 (m, 2H), 2.20 (s, 3H), 2.21 (s, 3H), 4.54 (d, 1H, J=7.6 Hz, exchanged with D$_2$O), 5.12 (d, 1H, J=10.5 Hz, exchanged with D$_2$O), 5.47 (t, 1H, J=6.3 Hz), 5.55 (t, 1H, J=6.3 Hz), 6.06 (2d+s) and 6.26 (d, 1H, J=7.3 Hz).

$^{13}$C NMR (CDCl$_3$): 14.0, 20.8, 22.6, 24.9, 25.0, 29.1, 29.3, 31.7, 32.9, 33.0, 69.3, 69.8, 98.0, 98.2, 118.3, 119.0, 166.7, 167.1, 170.0 and 171.1.

MS m/e: exact mass cald for C$_{15}$H$_{24}$O$_5$ 284.1624, found 284.1691.

EXAMPLE 11

5-Acetoxy-4-(1-acetoxynonyl)-2(5H)-furanone

A mixture of 4-(1-acetoxynonyl)-5-hydroxy-2(5H)-furanone (77.3 mg, 0.27 mmol), acetic anhydride (½ ml) and pyridine (1 ml) was stirred under argon at ca. 20° for 20h. After most of the solvent was removed under high vacuum (<40°), the residue was dissolved in ether (20 ml) and washed thoroughly with aqueous copper sulfate and water. Drying (magnesium sulfate) and evaporation gave a brown oil, which was flash chromatographed on silica using 30% ethyl ether/petroleum ether. Fractions with R$_f$0.22 on evaporation afforded the title compound as a light yellow oil.

$^1$H NMR (CDCl$_3$): 0.92 (t, 3H, J=7.4 Hz), 1.31 (broad s, 12H), 1.83 (m, 2H), 2.13-2.24 (4s, 6H), 5.58 (t, 1H, J=7.5 Hz), 5.69 (t, 1H, J=7.5 Hz), 6.11 (s, 1H), 6.14 (s, 1H), 6.95 (s, 1H) and 7.04 (s, 1H).

$^{13}$C NMR (CDCl$_3$): 14.0, 20.6, 22.5, 24.7, 29.1, 29.2, 31.7, 32.6, 33.1, 68.0, 69.1, 92.3, 92.6, 119.2, 120.0, 164.5, 164.6, 168.7, 168.8, 169.7 and 170.0.

MS m/e: exact mass cald for $C_{17}H_{27}O_6$ $(M+H)^+$ 326.1808, found 326.1804.

EXAMPLE 12

4-(1-Acetoxynonyl)-5-octanoyloxy-2(5H)-furanone

Octanoyl chloride (83.6 μl, 0.49 mmol), followed by triethylamine (68.2 μl, 0.49 mmol), was added to 4-(1-acetoxynonyl)-5-hydroxy-2(5H)-furanone (132.6 mg, 0.47 mmol) in tetrahydrofuran (6 ml) at 0°. Stirring was continued for 14h while the ice bath attained room temperature. The mixture was diluted with water (10 ml) and extracted with dichloromethane. Evaporation of the dried (magnesium sulfate) extract gave a yellow oil, which was flash chromatographed on silica using 30% ethyl ether/petroleum ether. Fractions with $R_f$ 0.38 on evaporation gave the title compound as a colorless oil.

$^1H$ NMR (CDCl$_3$): 0.95 (t, 3H, J=5.7 Hz), 1.30 (broad s, 20H), 1.7 (m, 4H), 2.16 (s, 3H), 2.45 (t, 2H, J=7.2 Hz), 5.68 (t, 1H, J=5.6 Hz), 6.11 (s, 1H), 6.96 (s, 1H).

$^{13}C$ NMR (CDCl$_3$): 13.9, 20.5, 22.4, 24.3, 24.4, 24.6, 24.7, 28.7, 28.8, 29.0, 29.2, 31.5, 31.7, 32.6, 33.1, 33.8, 68.0, 69.1, 92.2, 92.5, 119.0, 119.9, 164.6, 168.7, 169.6 and 171.5.

MS m/e: exact mass cald for $C_{23}H_{38}O_6$ 410.2668, found 410.2674.

EXAMPLE 13

4-(1-Hydroxyundecyl)-2-trimethylsilylfuran

A mixture of 1-bromodecane (2.83 g, 13 mmol) and magnesium turnings (322 mg, 13.5 mmol) in THF (10 ml) was refluxed under argon for 60 min. After cooling to 0°, a solution of 5-bromo-3-furaldehyde (2.24 g, 13 mmol) in tetrahydrofuran (3 ml) was added and conditions maintained for 20 min. The mixture was further cooled to −78° and tert-butyl lithium (a 1.7M solution in pentane; 9.04 ml, 15.4 mmol) was added dropwise, followed by chlorotrimethylsilane (4.88 ml, 38.4 mmol) after 20 min. Stirring was continued overnight (12h) while the cooling bath attained room temperature. The mixture was quenched with saturated aqueous ammonium chloride, diluted with water (15 ml) and extracted with ether. Evaporation of the dried (magnesium sulfate) extract gave a brown oil, which was flash chromatographed on silica using 15% ethyl ether/petroleum ether. Fractions with about $R_f$ 0.22 on evaporation gave the title compound as a yellow oil.

$^1H$ NMR (CDCl$_3$): 0.26 (s, 9H), 0.89 (t, 3H, J=7.3 Hz), 1.27 (broad s, 16H), 1.62 (br, 1H), 1.75 (m, 2H), 4.65 (t, 1H, J=6.8 Hz), 6.63 (s, 1H) and 7.57 (s, 1H).

MS m/e (% abundance) 293 (M$^+$−OH, 2), 221 (5), 177 (31), 175 (33), 97 (14), 87 (10), 85 (64), 83 (100), 73 (14) and 57 (12).

4-(1-Acetoxyundecyl)-2-trimethylsilylfuran

A mixture of 4-(1-hydroxyundecyl)-2-trimethylsilylfuran (1.21 g, 3.89 mmol), acetic anhydride (4 ml) and pyridine (6 ml) was stirred under argon at ca. 20° for 14h. After most of the solvent was removed under high vacuum (<40°), the residue was dissolved in ether (40 ml) and washed thoroughly with aqueous copper sulfate and water. Drying (magnesium sulfate) and evaporation gave a brown oil, which was flash chromatographed on silica using 5% ethyl ether/petroleum ether. Fractions with $R_f$ of about 0.3 on evaporation afforded the captioned compound as a pale yellow oil.

$^1H$ NMR (CDCl$_3$): 0.26 (s, 9H), 0.89 (t, 3H, J=7.6 Hz), 1.26 (broad s, 16H), 1.85 (m, 2H), 2.06 (s, 3H), 5.77 (t, 1H, J=6.8 Hz), 6.59 (s, 1H) and 7.60 (s, 1H).

MS m/e (% abundance) 353 (M$^+$+1, 9), 352 (33), 311 (23), 310 (90), 293 (12), 292 (12), 183 (28), 170 (38), 169 (39), 154 (20), 153 (11), 117 (30) and 73 (100).

4-(1-Acetoxyundecyl)-5-hydroxy-2(5H)-furanone

A mixture 4-(1-acetoxyundecyl)-2-trimethylsilylfuran (290.8 mg, 0.83 mmol) and Rose Bengal (5 mg) in tetrahydrofuran (7 ml) was exposed to singlet oxygen for 3.5h at −78°. The residue, after solvent removal, was flash chromatographed on silica using 40% ethyl ether/petroleum ether. Fractions with $R_f$ of about 0.26 (60% ethyl ether/petroleum ether) on evaporation gave the title furanone as colorless prisms.

mp 59°-60°.

$^1H$ NMR (CDCl$_3$): 0.91 (t, 3H, J=7.1 Hz), 1.29 (broad s, 16H), 1.83 (m, 2H), 2.15 (s, 3H), 2.17 (s, 3H), 4.80 (br, 1H), 5.36 (t, 1H, J=6.8 Hz), 5.50 (t, 1H, J=6.8 Hz), 6.02 (s, 2H), 6.03 (s, 1H) and 6.22 (s, 1H).

$^{13}C$ NMR (CDCl$_3$): 14.1, 20.8, 22.6, 24.9, 25.1, 29.1, 29.3, 29.3, 29.5, 32.9, 33.1, 69.2, 69.8, 98.0, 98.1, 118.4, 119.1, 166.8, 167.2, 170.0, 170.8 and 171.2.

MS m/e: exact mass calculated for $C_{17}H_{28}O_5$ 312.2015, found 312.2025

EXAMPLE 14

4-(1-Hydroxytridecyl)-2-trimethylsilylfuran

A mixture of 1-bromododecane (3.45 g, 14 mmol) and magnesium turnings (349 mg, 14.5 mmol) in tetrahydrofuran (10 ml) was refluxed under argon for 1h. After cooling to 0°, a solution of 5-bromo-3-furaldehyde (2.42 g, 14 mmol) in tetrahydrofuran (3 ml) was added and conditions maintained for 20 min. The mixture was further cooled to −78° and tert-butyl lithium (a 1.7M solution in pentane; 9.77 ml, 1.67 mmol) was added dropwise, followed by chlorotrimethylsilane (5.27 ml, 41.5 mmol) after 20 min. Stirring was continued overnight (12h) while the cooling bath attained room temperature. The mixture was quenched with saturated aqueous ammonium chloride, diluted with water (15 ml) and extracted with ethyl ether. Evaporation of the dried (magnesium sulfate) extract gave a brown oil, which was flash chromatographed on silica using 15% ethyl ether/petroleum ether. Fractions with $R_f$ of about 0.25 on evaporation afforded the title trimethylsilylfuran as a pale yellow oil.

$^1H$ NMR (CDCl$_3$): 0.26 (s, 9H), 0.91 (t, 3H), J=6.7 Hz), 1.29 (broad s, 20H), 1.64 (br, 1H), 1.77 (m, 2H), 4.67 (t, 1H, J=6.8 Hz), 6.65 (s, 1H) and 7.59 (s, 1H).

MS m/e (% abundance) 339 (m$^+$+1, 9), 338 (31), 170 (35), 169 (100), 75 (15) and 73 (50).

4-(1-Hydroxytridecyl)-5-hydroxy-2(5H)-furanone

A mixture of 4-(1-hydroxytridecyl)-2-trimethylsilylfuran (271.2 mg, 0.8 mmol) and Rose Bengal (5 mg) in tetrahydrofuran (10 ml) was exposed to singlet oxygen for 2 hr at −78°. The residue, after solvent removal, was flash chromatographed on silica using 70% ethyl ether/petroleum ether. Fractions with $R_f$ of about 0.09 (60% ethyl ether/petroleum ether) on evaporation afforded the captioned furanone as a colorless oil.

$^1H$ NMR (CDCl$_3$): 0.91 (t, 3H, J=6.8 Hz), 1.29-1.34 (broad m, 20H), 1.75 (m, 2H), 4.00 (br, 2H, exchanged with D$_2$O), 4.68 (m, 1H), 5.99 (s, 1H), 6.10 (d, 1H, J=7.5 Hz, sharpened into a singlet on D$_2$O exchange), 6.15 (d, 1H, sharpened into a singlet on D$_2$O exchange) and 6.28 (s, 1H).

$^{13}$C NMR (CDCl$_3$): 14.1, 22.7, 25.1, 25.1, 25.7, 29.1, 29.3, 29.5, 29.6, 29.6, 29.8, 31.9, 35.3, 35.6, 68.0, 68.2, 97.5, 97.6, 117.6, 118.1, 168.9, 170.4, 170.6 and 170.9.

MS m/e: exact mass calculated for C$_{17}$H$_{31}$O$_4$ (M+H)$^+$ 299.2222, found 299.2231.

EXAMPLE 15

4-(1-Acetoxytridecyl)-2-trimethylsilylfuran

A mixture of 4-(1-hydroxytridecyl)-2-trimethylsilylfuran (1.32 g, 3.89 mmol), acetic anhydride (4 ml) and pyridine (6 ml) was stirred under argon at ca. 20° for 16 h. After most of the solvent was removed under high vacuum (<40°), the residue was dissolved in ethyl ether (40 ml) and washed thoroughly with aqueous copper sulfate and water. Drying (magnesium sulfate) and evaporation gave a brown oil, which was flash chromatographed on silica using 5% ethyl ether/petroleum ether. Fractions with R$_f$ of about 0.55 (10% ethyl ether/petroleum ether) on evaporation gave the desired trimethylsilylfuran as a pale yellow oil.

$^1$H NMR (CDCl$_3$): 0.29 (s, 9H), 0.93 (t, 3H, J=6.8 Hz), 1.30 (broad s, 20H), 1.90 (m, 2H), 2.09 (s, 3H), 5.81 (t, 1H, J=6.8 Hz), 6.63 (s, 1H) and 7.64 (s, 1H).

MS m/e (% abundance) 381 (M$^+$+1, 13), 380 (42), 346 (11), 339 (28), 338 (100), 321 (29), 320 (17), 183 (23), 170 (36), 169 (29), 154 (26), 153 (11), 117 (27), 75 (23) and 73 (90).

4-(1-Acetoxytridecyl)-5-hydroxy-2(5H)-furanone

A mixture of 4-(1-acetoxytridecyl)-2-trimethylsilylfuran (314.2 mg, 0.83 mmol) and Rose Bengal (5 mg) in tetrahydrofuran (7 ml) was exposed to singlet oxygen for 2.5 hrs. at −78°. The residue, after solvent removal, was flash chromatographed on silica using 45% ethyl ether/petroleum ether. Fractions with R$_f$ of about 0.21 (60% ethyl ether/petroleum ether) on evaporation afforded the 4-(1-acetoxytridecyl)-5-hydroxy-2(5H)-furanone as colorless prisms: mp 67°-8°.

$^1$H NMR (CDCl$_3$): 0.88 (t, 3H, J=7.5 Hz), 1.26 (broad s, 20H), 1.82 (m, 2H), 2.11 (s, 3H), 2.14 (s, 3H), 4.06 (broad d, 1H, exchanged with D$_2$O), 4.86 (broad d, 1H, exchanged with D$_2$O), 5.36 (t, 1H, J=5.6 Hz), 5.50 (t, 1H, J=5.6 Hz), 5.95 (s, 1H), 5.99 (s, 1H), 6.00 (d, 1H, J=10 Hz) and 6.19 (d, 1H, J=7.5 Hz).

$^{13}$C NMR (CDCl$_3$): 14.1, 20.8, 22.7, 25.0, 25.1, 29.2, 29.3, 29.3, 29.5, 31.9, 33.0, 33.2, 69.2, 69.8, 98.0, 118.5, 119.2, 167.1, 169.8, 170.7 and 171.2.

MS m/e: exact mass calculated for C$_{19}$H$_{36}$O$_5$N (M+NH$_4$)$^+$ 358.2593, found 358.2597.

EXAMPLE 16

4-(1-Methoxytridecyl)-2-trimethylsilylfuran

A mixture of 4-(1-hydroxytridecyl)-2-trimethylsilylfuran (318.5 mg, 0.9 mmol), sodium hydride (60% dispersion in oil; 150 mg, 3.8 mmol) and iodomethane (0.29 ml, 4.7 mmol) in tetrahydrofuran (7 ml) was refluxed for 16 hr. On cooling, the mixture was diluted with ethyl ether (20 ml), quenched with methanol (2 ml) and washed with water. Evaporation of the dried (magnesium sulfate) organic phase gave a deep yellow oil, identified as 4-(1-methoxytridecyl)-2-trimethylsilylfuran.

$^1$H NMR (CDCl$_3$): 0.32 (s, 9H), 0.94 (t, 3H, J=7.1 Hz), 1.31 (broad s, 20H), 1.65 (m, 1H), 1.85 (m, 1H), 3.28 (s, 1H), 4.14 (t, 1H, J=10 Hz), 6.63 (s, 1H) and 7.58 (s, 1H). The product was used directly in the next stage without further purification.

4-(1-Methoxytridecyl)-5-hydroxy-2(5H)-furanone

A mixture of 4-(1-methoxytridecyl)-2-trimethylsilylfuran (280 mg, 0.8 mmol) and Rose Bengal (5 mg) in tetrahydrofuran (7 ml) was exposed to singlet oxygen for 5 hr at −78°. The residue, after solvent removal, was flash chromatographed on silica using 60% ethyl ether/petroleum ether. Fractions with R$_f$ of about 0.21 on evaporation afforded the 4-(1-methoxytridecyl)-5-hydroxy-2(5H)-furanone as a colorless prism: mp 53°-4°.

$^1$H NMR (CDCl$_3$): 0.99 (t, 3H, J=8.3 Hz), 1.28 (broad s, 20H), 1.75 (m, 2H), 3.40 (s, 3H), 3.41 (s, 3H), 4.10 (m, 1H), 4.30 (br, 1H), 6.04 (s, 1H), 6.05 (s, 1H), 6.08 (s, 1H) and 6.19 (s, 1H).

$^{13}$C NMR (CDCl$_3$): 14.2, 22.7, 25.0, 25.1, 29.4, 29.5, 29.5, 29.6, 29.7, 29.9, 32.0, 32.9, 33.8, 57.6, 57.9, 97.1, 97.8, 118.5, 119.7 and 168.6.

MS m/e: exact mass cald for C$_{18}$H$_{33}$O$_4$ (M+H)$^+$ 313.2379, found 313.2381.

EXAMPLE 17

4-(1-Methoxy-4-phenylbutyl)-2-trimethylsilylfuran

To a stirred suspension of sodium hydride (0.063 g., 1.05 mmol) in 10 ml tetrahydrofuran at 0° under argon, was added dropwise via syringe 4-(1-hydroxy-4-phenylbutyl)-2-trimethylsilylfuran (0.274 g., 0.951 mmol). This was followed by the addition of iodomethane (0.352 g., 2.48 mmol) and warming of the reaction mixture to room temperature. Several more equivalents of sodium hydride and iodomethane were subsequently added in increments over 2.5 hours until TLC indicated that no starting material remained. The reaction mixture was carefully filtered through celite and partitioned between ethyl ether and 5% hydrochloric acid. The organic portion was washed with 5% sodium bicarbonate, water, saturated sodium chloride, dried over magnesium sulfate, filtered and concentrated to give an oil. Purification by flash chromatography (silica, hexane to 5% ethyl ether/hexane) yielded the desired methyl ether.

$^1$H NMR (CDCl$_3$): 7.51 (s, 1H); 7.1 to 7.3 (m, 5H); 6.54 (s, 1H); 4.09 (t, J=6.1 Hz, 1H); 3.21 (s, 3H); 2.61 (t, J=7.0 Hz, 2H); 1.5 to 1.9 (m, 4H); 0.25 (s, 9H).

$^{13}$C NMR (CDCl$_3$): 161.4, 144.2, 142.4, 128.4, 128.2, 125.8, 125.7, 118.4, 75.6, 56.1, 35.9, 35.8, 27.5, −1.7.

m/z Calculated for C$_{18}$H$_{26}$O$_2$Si: 302.1702; obtained (EI+): 302.1700

5-Hydroxy-4-(1-methoxy-4-phenylbutyl)-2-(5H)-furanone

A stirred solution of 4-(1-methoxy-4-phenylbutyl)2-trimethylsilylfuran (0.173 g., 0.572 mmol) and Rose Bengal (trace) in methanol was flushed with oxygen and cooled to −78°. The solution was subsequently irradiated with a 150 Watt flood lamp while under a constant, positive pressure of oxygen until starting material was no longer visible by TLC. The solution was warmed to room temperature, concentrated to a red oil (0.154 g.), and purified by flash chromatography (silica, 50% ethyl acetate/hexane) to give the desired hydroxybutenolide.

$^1$H NMR (mixture of diasteriomers) (CDCl$_3$): 7.3 to 7.1 (m, 5H); 6.2 (m, 0.3H); 5.99 (s, 1H); 5.95 (m, 0.7H); 5.5 (broad s, 0.7H); 5.35 (broad s, 0.3H); 4.1 (m, 0.7H);

4.03 (m, 0.3H); 3.34 (s, 2H); 3.33 (s, 1H); 2.7 to 2.55 (m, 2H); 1.9 to 1.5 (m, 4H).

$^{13}$C NMR (mixture of diasteriomers) (CDCl$_3$): 171.2 and 171.1, 169.4 and 168.0, 141.5, 128.2, 125.7, 118.8 and 117.8, 98.4 and 97.5, 76.6 and 76.4, 57.6 and 57.3, 35.2, 32.9 and 32.1, 26.4.

m/z Calculated for C$_{15}$H$_{19}$O$_4$ (MH+): 263.1283. Obtained (EI+): 263.1289.

EXAMPLE 18

4-(1-Acetoxy-4-phenylbutyl)-2-trimethylsilylfuran

A solution of 4-(1-hydroxy-4-phenylbutyl)-2-trimethylsilylfuran (0.249 g., 0.862 mmol), acetic anhydride (1 ml, excess) and pyridine (3 to 4 drops, excess) was stirred at room temperature until no starting material remained (as monitored by TLC). The reaction mixture was then partitioned between ethyl ether and a 5% ammonium chloride solution. The organic portion was washed repeatedly with saturated sodium bicarbonate solution, twice with aqueous cupric sulfate solution, water, saturated sodium chloride solution, dried over magnesium sulfate, filtered and concentrated to give a pale yellow oil (0.396 g). This material was further purified by flash chromatography (silica, 5% ethyl acetate/hexane) to give the desired acetate.

$^1$H NMR (CDCl$_3$): 7.56 (s, 1H); 7.33 to 7.10 (m, 5H); 6.55 (s, 1H); 5.80 (t, J=7.1 Hz, 1H); 2.63 (t, J=7.4 Hz, 2H); 2.03 to 1.55 (m, 4H); 2.03 (s, 3H); 0.24 (s, 9H).

$^{13}$C NMR (CDCl$_3$): 170.4, 161.2, 144.4, 141.9, 128.3, 126.0, 125.8, 124.7, 118.5, 68.3, 35.4, 34.2, 27.2, 21.3, −1.7.

4-(1-Acetoxy-4-phenylbutyl)-5-hydroxy-2(5H)-furanone

A stirred solution of 4-(1-acetoxy-4-phenylbutyl)2-trimethylsilylfuran (0.065 g., 0.20 mmol) and Rose Bengal (trace) in methanol was flushed with oxygen and cooled to −78°. The solution was subsequently irradiated with a 150 Watt flood lamp while under a constant positive pressure of oxygen until starting material was no longer visible by TLC. The solution was warmed to room temperature, concentrated to a red oil (0.117 g.), and purified by flash chromatography (silica, 30% ethyl acetate/hexane) to give the title hydroxybutenolide.

$^1$H NMR (mixture of diasteriomers) (CDCl$_3$): 7.35 to 7.10 (m, 5H); 6.17 (s, 0.3H); 5.95 (m, 1.7H); 5.51 (m, 1H); 5.33 (broad s, 0.7H); 5.20 (broad s, 0.3H); 2.75 to 2.55 (m, 2H); 2.12 (s, 2H); 2.09 (s, 1H); 2.0 to 1.6 (m, 4H).

$^{13}$C NMR (mixture of diasteriomers) (CDCl$_3$): 171.0 and 170.6, 170.3 and 169.9, 166.8 and 166.4, 141.4 and 141.1, 128.5 and 128.4, 128.3, 126.1 and 126.0, 119.2 and 118.5, 98.0 and 97.8, 69.5 and 69.0, 35.2 and 35.1, 32.4, 26.7 and 26.6, 20.8.

m/z Calculated for C$_{14}$H$_{14}$O$_3$ (M+−HOAc): 230.0943, obtained (EI+): 230.0939.

EXAMPLE 19

4-(1-Acetoxy-4-phenylbutyl)-5-methoxy-2(5H)-furanone

A solution of 4-(1-acetoxy-4-phenylbutyl)-5-hydroxy-2(5H)-furanone (0.020 g., 0.069 mmol) and p-toluene sulfonic acid (approx. 3 mg.) in 2.5 ml methanol was stirred for 72 hours at room temperature. The reaction mixture was concentrated and partitioned between ethyl ether and water. The organic portion was washed with saturated sodium chloride solution, dried over magnesium sulfate, filtered and concentrated to give an oil (0.027 g.) This material was purified by flash chromatography (30% ethyl acetate/hexane) to give a diasteriomeric mixture of the two methoxybutenolides. The mixture was subsequently separated by semi-preparative HPLC on a Whatman Partisil M-9 silica column, with an elution rate of 4 ml/min with 20% ethyl acetate/hexane. One diasteriomer (A) was eluted at 11 minutes, followed by the other (B) at 12 minutes. Concentration gave the purified compounds.

Diasteriomer (A). —$^1$H NMR (CDCl$_3$): 7.4 to 7.1 (m, 5H); 5.97 (s, 1H); 5.69 (m, 1H); 5.57 (s, 1H); 3.50 (s, 3H); 2.55 to 2.75 (m, 2H); 2.13 (s, 3H); 1.5 to 1.9 (m, 4H).

$^{13}$C NMR (CDCl$_3$): 169.8, 169.3, 164.4, 141.2, 128.5, 128.4, 126.1, 119.2, 102.6, 69.2, 56.7, 35.1, 31.8, 26.3, 20.8

Diasteriomer (B). —$^1$H NMR (CDCl$_3$): 7.35 to 7.1 (m, 5H); 5.98 (s, 1H); 5.78 (s, 1H); 5.44 (broad t, J=6.7 Hz, 1H); 3.56 (s, 3H); 2.7 to 2.55 (m, 2H); 2.09 (s, 3H); 1.95 to 1.5 (m, 4H).

$^{13}$C NMR (CDCl$_3$): 170.1, 169.4, 164.7, 141.4, 128.41, 128.36, 126.0, 119.7, 103.7, 68.7, 57.8, 35.2, 32.3, 26.7, 20.7.

m/z calculated for C$_{17}$H$_{21}$O$_5$ (MH+)=305.1389, obtained (CI+)=305.1395.

EXAMPLE 20

4-(1-Dodecoyloxy-4-phenylbutyl)-2-trimethylsilylfuran

To a stirred solution of 3-phenylpropylmagnesium bromide (2.28 ml of a 0.6M solution in tetrahydrofuran, 1.37 mmol, generated from 1-bromo-3-phenylpropane and magnesium) at 0° under argon, was added dropwise 5-trimethylsilyl-3-furaldehyde (0.20 g., 1.19 mmol) in two ml tetrahydrofuran. This solution was warmed to room temperature and stirred for thirty minutes, then cooled again to 0°. Lauroyl chloride (0.296 g., 1.35 mmol) was added dropwise and the reaction mixture was warmed to room temperature and partitioned between ethyl ether and a 5% sodium bicarbonate solution. The organic portion was washed with water, saturated sodium chloride solution, dried over magnesium sulfate, filtered and concentrated to give an oil (0.844 g.). Purification by flash chromatography (silica, 5% ethyl ether/petroleum ether) yielded the desired furan ester.

$^1$H NMR (CDCl$_3$): 7.55 (s, 1H); 7.3 to 7.1 (m, 5H); 6.54 (s, 1H); 5.82 (t, J=6.8 Hz, 1H); 2.63 (t, J=7.5 Hz, 2H); 2.27 (t, J=7.5 Hz, 2H); 2.0 to 1.5 (m, 6H); 1.45 to 1.15 (m, 16H); 0.88 (t, J=6.2 Hz, 3H); 0.24 (s, 9H).

$^{13}$C NMR (CDCl$_3$): 173.1, 161.1, 144.3, 141.8, 128.29, 128.25, 125.8, 124.9, 118.5, 68.0, 35.3, 34.5, 34.3, 31.9, 29.6, 29.4, 29.3, 29.2, 29.0, 27.2, 25.0, 22.6, 14.1, −1.7.

m/z Calculated for C$_{29}$H$_{46}$O$_3$Si: 470.3216. obtained (EI+): 470.3202

4-(1-Dodecoyloxy-4-phenylbutyl)-5-hydroxy-2(5H)-furanone

A stirred solution of 4-(1-dodecoyloxy-4-phenylbutyl)-2-trimethylsilylfuran (0.563 g., 1.19 mmol) and Rose Bengal (trace) in acetone was flushed with oxygen and cooled to −78°. The solution was subsequently irradiated with a 150 Watt flood lamp while under a constant, positive pressure of oxygen until starting material was no longer visible by TLC. The solution was warmed to room temperature, concentrated to a red oil, and purified by flash chromatography (silica, 40% ethyl ether/petroleum ether) to give the desired hydroxybutenolide.

$^1$H NMR (mixture of diasteriomers) (CDCl$_3$): 7.05 to 7.3 (m, 5H); 6.17 (s, 0.4H); 5.95 (broad s, 0.4H); 5.91 (m, 1.6H); 5.75 (broad s, 0.6H); 5.60 (m, 0.6H); 5.52 (m, 0.4H); 2.7 to 2.5 (m, 2H); 2.25 to 2.4 (m, 2H); 2.0 to 1.5 (m, 6H); 1.4 to 1.15 (m, 16H), 0.86 (t, J=6.6 Hz, 3H).

$^{13}$C NMR (mixture of diasteriomers) (CDCl$_3$): 173.4 and 173.3, 170.7 and 170.4, 167.0 and 166.8, 141.4 and 141.1, 128.3, 128.2, 125.9 and 125.8, 118.7 and 118.1, 98.2 and 97.8, 69.1 and 68.7, 35.1 and 35.0, 34.0, 32.2 and 32.1, 31.7, 29.4, 29.3, 29.2, 29.1, 29.0, 26.6 and 26.4, 24.7, 22.5 and 14.0.

m/z Calculated for C$_{26}$H$_{38}$O$_5$: 430.2719, obtained (EI+): 430.2707.

EXAMPLE 21

4-(1-Hydroxynonadecyl)-2-trimethylsilylfuran.

To a stirred solution of octadecylmagnesium bromide (10.2 ml of a 0.34M solution in ethyl ether, 3.46 mmol, generated from 1-bromooctadecane and magnesium using iodine as an initiator) at 0° under argon, was added dropwise 5-trimethylsilyl-3-furaldehyde (0.265 g., 1.57 mmol) in 2 ml tetrahydrofuran. This solution was allowed to warm to room temperature, stirred for 30 minutes, and quenched with a 5% ammonium chloride solution. The resulting mixture was partitioned between ethyl ether and 5% sodium bicarbonate. The organic portion was washed with 10% sodium bisulfite, water, saturated sodium chloride solution, dried over magnesium sulfate, filtered and concentrated to give a residue. This was taken up in ethyl ether and filtered. The ether portion was concentrated to give a waxy residue which was purified by flash chromatography (silica, 10% ethyl ether/petroleum ether) to give the desired alcohol.

$^1$H NMR (CDCl$_3$): 7.56 (s, 1H); 6.62 (s, 1H); 4.64 (t, J=6.7 Hz, 1H); 1.7 to 1.8 (m, 2H); 1.64 (broad s, 1H); 1.2 to 1.4 (m, 32H); 0.88 (t, J=6.7 Hz, 3H); 0.25 (s, 9H).

$^{13}$C NMR (CDCl$_3$): 161.4, 143.1, 129.2, 118.3, 67.0, 37.9, 31.9, multiple peaks from 29.7 to 29.3, 25.8, 22.7, 14.1, −1.7.

m/z Calculated for C$_{26}$H$_{50}$O$_2$Si: 422.3580, obtained (EI+): 422.3583.

4-(1-Acetoxynonadecyl)-2-trimethylsilylfuran

A solution of 4-(1-hydroxynonadecyl)-2-trimethylsilylfuran (0.294 g., 0.697 mmol), acetic anhydride (3 ml, excess) and pyridine (0.064 g., 0.761 mmol) was stirred at room temperature until no starting material remained (as monitored by TLC). The reaction mixture was then concentrated under high vacuum for 6 hours to give a yellow oil. This material was purified by flash chromatography (silica, 2.5% ethyl ether/petroleum ether) to give the desired acetate.

$^1$H NMR (CDCl$_3$): 7.58 (s, 1H); 6.59 (s, 1H); 5.77 (t, J=7.2 Hz, 1H); 2.03 (s, 3H); 1.7 to 1.95 (m, 2H); 1.2 to 1.4 (m, 32H); 0.88 (t, J=6.5 Hz, 3H); 0.25 (s, 9H).

$^{13}$C NMR (CDCl$_3$): 170.4, 161.0, 144.4, 124.9, 118.6, 68.5, 34.7, 31.9, multiple peaks from 29.7 to 29.3, 25.5, 22.7, 21.2, 14.1, −1.7.

m/z Calculated for C$_{28}$H$_{52}$O$_3$Si: 464.3686, obtained (EI+): 464.3682.

4-(1-Acetoxynonadecyl)-5-hydroxy-2(5H)-furanone.

A stirred solution of 4-(1-acetoxynonadecyl)-2-trimethylsilylfuran (0.240 g., 0.517 mmol) and Rose Bengal (trace) in 250 ml acetone was flushed with oxygen and cooled to −78°. The solution was subsequently irradiated with a 150 Watt flood lamp while under a constant positive pressure of oxygen until starting material was no longer visible by TLC. The solution was warmed to room temperature, concentrated to a red oil and the residue was purified by flash chromatography (silica, ethyl ether) to give the desired hydroxybutenolide.

$^1$H NMR (mixture of diasteriomers) (CDCl$_3$): 6.2 (broad s, 0.4H); 5.95 to 6.05 (m, 1.6H); 5.4 to 5.5 (m, 1H); 5.2 to 5.3 (m, 0.6H); 5.0 (broad s, 0.4H); 2.14 (s, 1.8H); 2.11 (s, 1.2H); 1.75 to 1.9 (m, 2H); 1.2 to 1.45 (m, 32H); 0.88 (m, 3H).

$^{13}$C NMR (mixture of diasteriomers) (CDCl$_3$): 171.2 and 170.7, 170.1 and 169.9, 167.2 and 166.5, 119.1 and 118.4, 98.0, 69.7 and 69.2, 33.1, 33.0, 31.9, multiple peaks between 29.7 and 29.2, 25.1, 25.0, 22.7, 20.8, 14.1.

m/z Calculated for C$_{25}$H$_{48}$NO$_5$ (M+NH$_4$)+: 442.3532, obtained (CI+): 442.3546.

4-(1-Hydroxymethyl)-2-trimethylsilylfuran.

To a stirred suspension of lithium aluminum hydride (0.01 g., 0.263 mmol) in 1 ml dry tetrahydrofuran at 0° under argon was added dropwise 5-trimethylsilyl-3-furaldehyde (0.09 g., 0.535 mmol). This mixture was allowed to warm to room temperature, stirred for 15 minutes, quenched with a 5% ammonium chloride solution, and extracted twice with ethyl ether. The organic portion was washed with 5% sodium bicarbonate, water, saturated sodium chloride solution, dried over magnesium sulfate, filtered and concentrated to give the desired alcohol. This material was used without further purification.

$^1$H NMR (CDCl$_3$): 7.57 (s, 1H); 6.64 (s, 1H); 4.50 (s, 2H); 2.75 (broad s, 1H); 0.25 (s, 9H).

$^{13}$C NMR (CDCl$_3$): 161.5, 144.0, 125.0, 119.7, 56.2, −1.8.

m/z Calculated for C$_8$H$_{14}$O$_2$Si: 170.0763, obtained (EI+): 170.0766.

4-Dodecoyloxymethyl-2-trimethylsilylfuran

To a stirred solution of 4-hydroxymethyl-2-trimethylsilylfuran (0.288 g., 1.70 mmol) and pyridine (0.214 g., 2.55 mmol) in 30 ml dry tetrahydrofuran at 0° was added lauroyl chloride (0.408 g., 1.86 mmol). This solution was allowed to warm to room temperature, stirred 30 minutes, and partitioned between ethyl ether and 5% sodium bicarbonate solution. The organic portion was washed with aqueous cupric sulfate solution, water, saturated sodium chloride solution, dried over magnesium sulfate, filtered and concentrated to a colorless oil. This material was purified by flash chromatography (silica, 5% ethyl ether/petroleum ether) to give the desired ester.

$^1$H NMR (CDCl$_3$): 7.64 (s, 1H); 6.63 (s, 1H); 4.97 (s, 2H); 2.31 (t, J=7.3 Hz, 2H); 1.55 to 1.7 (m, 2H); 1.2 to 1.4 (m, 16H); 0.89 (t, J=6.3 Hz, 3H); 0.25 (s, 9H).

$^{13}$C NMR (CDCl$_3$): 173.5, 161.4, 145.6, 120.3, 57.4, 34.2, 31.8, 29.5, 29.4, 29.3, 29.2, 29.0, 24.9, 22.6, 14.0, −1.8.

m/z Calculated for C$_{20}$H$_{36}$O$_3$Si: 352.2434, obtained (CI+): 352.2448.

4-Dodecoyloxymethyl-5-hydroxy-2(5H)-furanone

A stirred solution of 4-dodecoyloxymethyl-2-trimethylsilylfuran (0.375 g., 1.07 mmol) and Rose Bengal (trace) in 275 ml of acetone was flushed with oxygen and cooled to −78°. The solution was subsequently irradiated with a 300 Watt flood lamp while under constant positive pressure of oxygen until the starting material was no longer visible by TLC. The solution was warmed to room temperature and concentrated to a pale, orange solid residue. This material was purified by passing through a small plug of silica (ethyl ether as eluent) to give the desired hydroxybutenolide.

$^1$H NMR (CDCl$_3$): 6.16 (broad s, 1H); 6.05 (broad s, 1H); 5.55 (broad s, 1H); 4.97 (m, 2H); 2.41 (m, 2H); 1.6 to 1.75 (m, 2H); 1.2 to 1.4 (m, 16H); 0.88 (m, 3H).

$^{13}$C NMR (CDCl$_3$): 173.4, 170.6, 163.2, 118.7, 97.6, 58.8, 33.9, 31.9, 29.5, 29.4, 29.3, 29.2, 29.1, 24.8, 22.6, 14.1.

m/z Calculated for C$_{17}$H$_{32}$NO$_5$ (M+NH$_4$)$^+$: 330.2280, obtained (CI+): 330.2282.

EXAMPLE 22

4-[1-hydroxy-2-(2-ethenyl)-2,6,10-trimethylundeca-5,9-diene]-2-trimethylsilylfuran To a stirred solution of farnesylmagnesium chloride (1.83 mmol, prepared from 1.83 mmol farnesyl chloride and 3.65 mmol magnesium, initiated with a catalytic amount of 1,2-dibromoethane) in 1.5 ml tetrahydrofuran at 0° under argon was added dropwise 5-trimethylsilyl-3-furaldehyde (0.277 g., 1.64 mmol) in 3 ml tetrahydrofuran. This solution was allowed to warm to room temperature, stirred for 1 hour, and then quenched with a 5% ammonium chloride solution. The resulting mixture was partitioned between ethyl ether and 5% sodium bicarbonate. The organic portion was washed with water, saturated sodium chloride, dried over magnesium sulfate, filtered and concentrated to give a pale yellow oil. This material was purified by flash chromatography (silica, 5% to 10% ethyl ether/petroleum ether) to give the alcohol.

$^1$H NMR (mixture of diasteriomers) (CDCl$_3$): 7.53 (s, 0.6H); 7.50 (s, 0.4H); 6.59 (s, 0.6H); 6.54 (s, 0.4H); 5.75 to 5.95 (m, 1H); 5.15 to 5.35 (m, 2H); 5.0 to 5.15 (m, 2H); 4.41 (s, 1H); 2.0 to 2.15 (s, 1H); 1.8 to 2.0 (m, 6H); 1.67 (s, 3H); 1.59 (s, 3H); 1.56 (s, 3H); 1.3 to 1.5 (m, 2H); 1.08 (s, 1.2H); 0.98 (s, 1.8H); 0.25 (s, 9H).

$^{13}$C NMR (mixture of diasteriomers) (CDCl$_3$): 160.2, 144.5 and 144.2, 144.0 and 142.9, 134.9 and 134.8, 131.3, 125.8 and 125.0, 124.7 and 124.6, 124.4, 120.0 and 119.8, 115.8 and 115.1, 74.0 and 73.2, 45.5 and 44.9, 39.7, 37.5 and 36.5, 26.7, 25.7, 22.6, 19.0, 17.7, 16.5 and 16.0, −1.6.

m/z Calculated for C$_{23}$H$_{38}$O$_2$Si: 374.2641, obtained (EI+): 374.2634.

4-[1-Acetoxy-2-(2-ethenyl)-2,6,10-trimethylundeca-5,9-diene]-2-trimethylsilylfuran A stirred solution of 4-[1-hydroxy-2-(2-ethenyl)2,6,10-trimethylundeca-5,9-diene]-2-trimethylsilylfuran (0.060 g., 0.160 mmol), acetic anhydride (0.5 ml, excess), and pyridine (5 drops, excess) was stirred at room temperature until no starting material remained (as monitored by TLC). The reaction mixture was then partitioned between ethyl ether and a 5% ammonium chloride solution. The organic portion was washed repeatedly with saturated sodium bicarbonate solution, twice with aqueous cupric sulfate solution, water, saturated sodium chloride solution, dried over magnesium sulfate, filtered and concentrated to give a pale yellow oil. This material was further purified by flash chromatography (silica, 5% ethyl ether/petroleum ether) to give the desired acetate as a diasteriomeric mixture.

$^1$H NMR (mixture of diasteriomers) (CDCl$_3$): 7.53 (s, 0.6H); 7.50 (s, 0.4H); 6.54 (s, 0.6H); 6.51 (s, 0.4H); 5.75 to 5.95 (m, 1H); 5.67 (s, 1H); 4.95 to 5.25 (m, 4H); 2.06 (s, 1.8H); 2.03 (s, 1.2H); 1.85 to 2.03 (m, 6H); 1.67 (s, 3H); 1.59 (s, 3H); 1.56 (s, 3H); 1.3 to 1.5 (m, 2H); 1.04 (s, 1.8H); 1.00 (s, 1.2H); 0.24 (s, 9H).

$^{13}$C NMR (mixture of diasteriomers) (CDCl$_3$): 170.0, 160.0, 145.0 and 144.7, 142.8 and 142.2, 134.9, 131.2, 124.5 and 124.4, 124.3, 122.3 and 122.2, 120.2, 114.6, 74.9 and 74.4, 44.1 and 43.7, 39.6, 37.2 and 36.6, 26.7, 25.6, 22.5, 21.1, 18.8, 18.0 and 17.6, 15.9, −1.7.

m/z Calculated for C$_{25}$H$_{40}$O$_3$Si: 416.2747, obtained (EI+): 416.2756.

4-[1-Acetoxy-2-(2-ethenyl)-2,6,10-trimethylundeca-5,9-diene]-5-hydroxy-2(5H)-furanone A stirred solution of 4-[1-acetoxy-2-(2-ethenyl)2,6,10-trimethylundeca-5,9-diene]-2-trimethylsilylfuran (0.042 g., 0.10 mmol) and Rose Bengal (trace) in acetone was flushed with oxygen and cooled to −78°. The solution was subsequently irradiated with a 150 Watt flood lamp while under a constant pressure of oxygen until starting material was no longer visible by TLC. The solution was warmed to room temperature, concentrated to a red oil and purified by flash chromatography (silica, 40% ethyl acetate/hexane) to give the desired hydroxybutenolide as a mixture of several diasteriomers.

$^1$H NMR (mixture of diasteriomers) (CDCl$_3$): 5.7 to 6.0 (m, 3H); 5.2 to 5.4 (m, 2H); 4.95 to 5.0 (m, 3H); 4.94 (s, 1H); 1.2 to 2.2 (m, 20H); 1.14 (s, 1.8H); 1.09 (s, 1.3H).

$^{13}$C NMR (mixture of diasteriomers) (CDCl$_3$): 172.3, 169.3, 165.6 and 165.0, 100.2 and 100.0, 75.3 and 75.0, 20.9.

m/z Calculated for C$_{22}$H$_{36}$NO$_5$ (M+NH$_4$)$^+$: 394.2593, obtained (CI+): 394.2571.

3-(1-Hydroxy-4-phenylbutyl)furan

To a stirred solution of 3-phenylpropyl magnesium bromide (4.5 ml of a 2.73M solution in ethyl ether, 12.3 mmol, generated from 1-bromo-3-phenylpropane and magnesium and initiated with iodine) at 0° under argon, was added dropwise 3-furaldehyde (1.08 g., 11.2 mmol) in 5 ml ethyl ether. This solution was allowed to warm to room temperature, stirred for 20 minutes, and then poured over crushed ice containing several drops of concentrated sulfuric acid. The resulting mixture was partitioned between ethyl ether and 5% sodium bisulfite. The organic portion was washed with 5% sodium bicarbonate solution, water, saturated sodium chloride solution, dried over magnesium sulfate, filtered and concentrated to give an oil. This material was further purified by flash chromatography (silica, 20% ethyl acetate/hexane) to give the desired alcohol.

$^1$H NMR (CDCl$_3$): 7.1 to 7.35 (m, 7H); 6.3 (s, 1H); 4.57 (t, 1H); 2.60 (t, 2H); 2.25 (s, 1H); 1.55 to 1.70 (m, 4H).

$^{13}$C NMR (CDCl$_3$): 143.2, 142.1, 138.9, 128.9, 128.3, 128.2, 125.7, 108.4, 66.6, 37.1, 35.5, 27.3.

3-(1-Acetoxy-4-phenylbutyl)furan

A solution of 3-(1-hydroxy-4-phenylbutyl)-furan (0.167 g., 0.772 mmol), acetic anhydride (1 ml, excess) and pyridine (3 to 4 drops, excess), was stirred at room temperature until no starting material remained (as monitored by TLC). The reaction mixture was then partitioned between ethyl ether and a 5% ammonium chloride solution. The organic portion was washed repeatedly with saturated sodium bicarbonate solution, aqueous cupric sulfate solution, water, saturated sodium chloride solution, dried over magnesium sulfate, filtered and concentrated to give 3-(1-acetoxy-4-phenylbutyl)-furan.

$^1$H NMR (CDCl$_3$): 7.1 to 7.3 (m, 7H); 6.35 (s, 1H); 5.79 (t, 1H); 2.63 (t, 2H); 2.04 (s, 3H); 1.6 to 1.95 (m, 4H).

3-(1-Acetoxy-4-phenylbutyl)-5-hydroxy-2(5H)-furanone 4-(1-Acetoxy-4-phenylbutyl)-5-hydroxy-2(5H)-furanone A stirred solution of 3-(1-acetoxy-4-phenylbutyl)-furan (0.244 g., 0.95 mmol) and Rose Bengal (trace) in methanol was flushed with oxygen and cooled to −78°. The solution was subsequently irradiated with a 150 Watt flood lamp while under a constant positive pressure of oxygen until starting material was no longer visible by TLC. The solution was warmed to room temperature, concentrated to a red oil (0.284 g.), and purified by flash chromato-graphy (silica, 20% ethyl acetate/methylene chloride) to give a mixture of two regioisomers [0.236 g.] The mixture was separated by semi-preparative HPLC on a Whatman Partisil M-9 silica column, using an elution rate of 4 ml/min. with 20% ethyl acetate/methylene chloride. The 4-substituted furanone product was eluted at 9.5 minutes, followed by the 3-substituted furanone product at 10.5 minutes. Concentration gave the purified the titled compounds, separately, as clear glasses which solidified on standing.

4-(1-Acetoxy-4-phenylbutyl)-5-hydroxy-2(5H)-furanone

Spectral data for this compound was the same here as described for this compound in Example 18.

3-(1-Acetoxy-4-phenylbutyl)-5-hydroxy-2(5H)-furanone $^1$H NMR (mixture of diasteriomers) (CDCl$_3$): 7.1 to 7.3 (m, 5H); 6.7 (s, 1H); 6.09 (2 s, 1H); 5.75 (broad s, 1H); 5.57 (broad s, 1H); 2.62 (m, 2H); 2.08 (s, 1.8H); 2.07 (s, 1.2H); 1.85 (m, 2H); 1.65 (m, 2H).

$^{13}$C NMR (mixture of diasteriomers) (CDCl$_3$): 170.4 and 170.3, 169.41 and 169.40, 145.3 and 145.2, 141.5, 136.53 and 136.46, 128.5 and 128.2, 125.8, 97.1 and 96.8, 68.3 and 68.1, 60.5, 35.1, 32.3 and 32.1, 26.6, 20.9 and 20.7.

m/z Calculated for C$_{14}$H$_{14}$O$_3$(M+-HOAc): 230.0943, obtained (EI+): 230.0952.

EXAMPLE 25

3-Dodecoyloxymethylfuran

To a stirred solution of 3-hydroxymethylfuran (1.01 g., 10.3 mmol) and pyridine (0.87 g., 10.3 mmol) in 30 ml dry tetrahydrofuran at 0° under argon was added lauroyl chloride (2.36 g., 10.8 mmol). This solution was allowed to warm to room temperature, during which time a white precipitate formed. After one hour, the mixture was filtered and the solution partitioned between ethyl ether and a 5% ammonium chloride solution. The organic portion was washed twice with 5% sodium bicarbonate solution, three times with aqueous cupric sulfate solution, water, saturated sodium chloride solution, dried over magnesium sulfate, filtered and concentrated to give a yellow oil. This material was further purified by flash chromatography (silica, 5% ethyl ether/petroleum ether) to give the desired ester.

$^1$H NMR (CDCl$_3$): 7.45 (broad s, 1H); 7.37 (broad s, 1H); 6.41 (broad s, 1H); 4.97 (s, 2H); 2.30 (t, 2H); 1.55 to 1.7 (m, 2H); 1.2 to 1.4 (m, 16H); 0.88 (t, 3H).

$^{13}$C NMR (CDCl$_3$): 173.3, 143.1, 141.3, 120.5, 110.4, 57.3, 34.1, 31.8, 29.5, 29.3, 29.2, 29.1, 29.0, 24.8, 22.6, 13.9.

m/z Calculated for C$_{17}$H$_{28}$O$_3$: 280.2194, obtained (EI+): 280.2042.

3-Dodecoyloxymethyl-5-hydroxy-2(5H)-furanone

A stirred solution of 3-dodecoyloxymethylfuran (0.602 g., 2.15 mmol) and Rose Bengal (trace) in 225 ml acetone was flushed with oxygen and cooled to −78°. The solution was subsequently irradiated with a 150 Watt flood lamp while under a constant pressure of oxygen until starting material was no longer visible by TLC. The solution was warmed to room temperature, concentrated to a red oil and the residue was purified by flash chromatography (silica, 60% ethyl ether/petroleum ether) to give the 3-substituted hydroxybutenolide as the only isolated product.

$^1$H NMR (CDCl$_3$): 7.11 (broad s, 1H); 6.20 (broad s, 1H); 5.42 (broad s, 1H); 4.85 (s, 2H); 2.38 (t, 2H); 1.55 to 1.7 (m, 2H); 1.2 to 1.4 (m, 16H); 0.88 (t, 3H).

$^{13}$C NMR (CDCl$_3$): 173.5, 170.0, 146.4, 133.0, 97.5, 57.2, 33.9, 31.8, 29.5, 29.4, 29.3, 29.2, 29.1, 24.8, 22.6, 14.1.

m/z Calculated for C$_{17}$H$_{32}$NO$_5$ (M+NH$_4$)+: 330.2281, obtained (CI+): 330.2283.

5-Dodecoyloxy-3-dodecoyloxymethyl-2(5H)-furanone

To a stirred solution of 3-dodecoyloxymethyl-5-hydroxy-2(5H)-furanone (0.098 g., 0.313 mmol) and pyridine (0.026 g., 0.313 mmol) in 3 ml anhydrous tetrahydrofuran at 0° was added lauroyl chloride (0.082 g., 0.376 mmol). The solution was allowed to warm to room temperature, stirred until starting material was no longer visible by TLC, and partitioned between ethyl ether and a 5% ammonium chloride solution. The organic portion was washed twice with 5% sodium bicarbonate solution, twice with aqueous cupric sulfate solution, water, saturated sodium chloride solution, dried over magnesium sulfate, filtered and concentrated to give a solid residue. This material was further purified by recrystallization (acetone/methanol) to give the desired ester.

$^1$H NMR (CDCl$_3$): 7.13 (s, 1H); 6.97 (s, 1H); 4.88 (s, 2H); 2.35 to 2.50 (m, 4H); 1.6 to 1.75 (m, 4H); 1.2 to 1.5 (m, 32H); 0.85 to 0.95 (m, 6H).

$^{13}$C NMR (CDCl$_3$): 172.9, 171.6, 168.4, 144.0, 133.9, 92.4, 57.1, 33.9, 33.8, 31.8, multiple peaks between 30.3 and 28.9, 24.8, 24.4, 22.6, 14.1.

m/z Calculated for C$_{29}$H$_{54}$NO$_6$ (M+NH$_4$)+: 512.3951, obtained (CI+): 512.3939.

EXAMPLE 27

5-Acetoxy-3-dodecoyloxymethyl-2(5H)-furanone

A stirred solution of 3-dodecoyloxymethyl-5-hydroxy-2(5H)-furanone (0.165 g., 0.527 mmol), acetic anhydride (0.5 ml, excess), and pyridine (7 drops, excess) was stirred at room temperature until no starting material remained (as monitored by TLC). The reaction mixture was then partitioned between ethyl ether and 5% ammonium chloride solution. The organic portion was washed repeatedly with saturated sodium bicarbonate solution, twice with aqueous cupric sulfate solution, water, saturated sodium chloride solution, dried over magnesium sulfate, filtered and concentrated to give a dark, yellow oil. This material was further purified by flash chromatography (silica, 30% to 40% ethyl ether/petroleum ether) to give the titled diester.

$^1$H NMR (CDCl$_3$): 7.13 (s, 1H); 6.95 (s, 1H); 4.89 (s, 2H); 2.39 (t, 2H); 2.17 (s, 3H); 1.6 to 1.75 (m, 2H); 1.2 to 1.5 (m, 16H); 0.88 (t, 3H).

$^{13}$C NMR (CDCl$_3$): 172.9, 168.8, 168.4, 143.9, 134.0, 92.5, 57.1, 33.9, 31.9, 29.6, 29.4, 29.3, 29.2, 29.1, 24.8, 22.7, 20.6, 14.1.

m/z Calculated for C$_{19}$H$_{34}$NO$_6$ (M+NH$_4$)$^+$: 372.2386, obtained (CI+): 372.2369.

EXAMPLE 28

3-(1-Hydroxy)undecylfuran.

A solution of decyl bromide in (3.00 g, 13.5 mmol) in 25 ml of tetrahydrofuran was added to 0.33 g. of magnesium turnings (0.33 g., 13.7 mmol). The mixture was stirred at room temperature for 2 hr, then heated at reflux for 1 hr, then cooled to room temperature. A solution of 3-furaldehyde (1.31 g., 13.6 mmol) in 25 ml of THF was added dropwise over 1 hr. The mixture was stirred for 1 hr, then cooled to 0° and quenched with a saturated aqueous ammonium chloride solution. The mixture was diluted with 100 ml of ether, washed with brine (3×50 ml), dried over magnesium sulfate and filtered. The solvent was removed in vacuo to give an orange oil. The product was purified by flash chromatography (10% ethyl acetate/hexane on silica gel) to give 3-(1-hydroxy)undecylfuran.

$^1$H NMR (CDCl$_3$): 7.36 (s, 2H), 6.38 (s, 1H), 4.61 (t, J=6.5 Hz, 1H), 2.10 (s, 1H), 1.72 (m, 2H), 1.25 (m, 16H, CH$_2$ envelope), 0.88 (t, J=5.6 Hz, 3H) $^{13}$C NMR (CDCl$_3$): 143.21, 138.90, 129.23, 108.41, 66.94, 37.81, 31.93, 29.36, 25.62, 22.66, 14.01.

3-(1-Keto)undecylfuran

A solution of 0.35 g. of 3-(1-hydroxy)undecylfuran in 5 ml of dichloromethane was added to a flask containing 0.32 g. of pyridinium chlorochromate and 25 ml of dry dichloromethane. The reaction was stirred at room temperature for 12 hr before diluting with ether (100 ml) and filtering through celite. The filtrate was washed with 5% aqueous sodium bicarbonate solution (50 ml) and brine. It was then dried over magnesium sulfate, filtered and the solvent removed to give a brown oil. Flash chromatography (10% ethyl acetate/hexane on silica gel) yielded the 3-(1-keto)undecylfuran, m.p. 51°-52°.

$^1$H NMR (CDCl$_3$): 8.02 (s, 1H), 7.43 (s, 1H), 6.77 (s, 1H) 2.73 (t, J=7.2 Hz, 2H) 1.31 (m, 14H, CH$_2$ envelope), 0.88 (t, J=5.8 Hz, 3H).

$^{13}$C NMR (CDCl$_3$): 195.31, 146.92, 144.11, 127.70, 108.64, 40.52, 31.83, 29.57, 29.45, 29.37, 24.45, 22.61, 14.01.

5-Hydroxy-4-(1-keto)undecyl-2(5H)-furanone

A mixture of 20 ml of methanol and 150 ml of tetrahydrofuran was saturated with oxygen by bubbling gas through the solution. The solution was cooled to −78° (dry ice/acetone) and 0.23 g. of 3-(1-keto)undecylfuran and 0.005 g of Rose Bengal were added to the solution. The solution was irradiated with a 300 Watt quartz-halogen spotlight for 4 hr at −78° while a stream of oxygen was passed continuously through the solution. The irradiation was stopped, the reaction warmed to room temperature and the solvent removed by evaporation. The residue was chromatographed on silica gel (20% ethyl acetate/hexane) to yield a fraction with R$_f$ of about 0.1. This fraction was triturated with 40% ethyl acetate/hexane to yield the captioned furanone, m.p. 65°-67°.

$^1$H NMR (CDCl$_3$): 6.59 (s, 1H), 6.45 (s, 1H), 2.80 (m; 2H), 1.67 (m, 2H), 1.26 (m, 14H, CH$_2$ envelope) and 0.88 (t, J=5.2 Hz, 3H).

$^{13}$C NMR (CDCl$_3$): 196.11, 157.81, 126.10, 97.15, 41.22, 31.91, 29.64, 29.51, 29.41, 29.12, 23.39, 22.74, 14.21.

Exact mass calculated for C$_{15}$H$_{24}$O$_4$ m/z 268.1674, found 268.1669.

EXAMPLE 29

3-bromo-4-(1-hydroxytridecyl)-5-hydroxy-2(5H)-furanone

A mixture of 0.8 g. of 4-(1-hydroxytridecyl)-5-hydroxy-2(5H)-furanone and 43 ml of methanol with a catalytic amount of BF$_3$.OEt$_2$ (3 drops) is stirred under argon for 15 hours. The mixture is diluted with methylene chloride, washed with water and dried over magnesium sulfate. The mixture is filtered and the solvent removed in vacuo. The resulting oil is purified by flash chromatography to give 4-(1-hydroxytridecyl)-5-methoxy-2(5H)-furanone.

A mixture of 0.3 g. of 4-(1-hydroxytridecyl)-5-methoxy-2(5H)-furanone and 0.5 ml of carbon tetrachloride is cooled to 0° and 0.55 ml of a 3.1M solution of bromine in carbon tetrachloride is added dropwise over 15 minutes. Two drops of glacial acetic acid are added and the mixture is allowed to warm to room temperature. The reaction is monitored by TLC. After one hour, the mixture is cooled to 0° and 25 ml of pyridine is added over 5 minutes. The mixture is stirred for one hour, filtered to remove pyridine hydrobromide and solvent removed to give a residue which is purified by flash chromatography to give 3-bromo-4-(1-hydroxytridecyl)-5-methoxy-2(5H)-furanone.

The methoxy group is cleaved by refluxing for 1.5 hr in concentrated hydrochloric acid to give 3-bromo-4-(1-hydroxytridecyl)-5-hydroxy-2(5H)-furanone.

EXAMPLE 30

4-(1-acetoxytridecyl)-5-hydroxy-2-tetrahydrofuranone

A solution of 4-(1-acetoxytridecyl)-5-hydroxy-2(5H)-furanone (0.11 g, 0.32 mmol) and 5% rhodium on alumina (24 mg) in 6 ml of methanol was stirred rapidly under a hydrogen atmosphere for two hours. The mixture was concentrated, taken up in ethyl acetate, filtered through celite, and concentrated to give the tetrahydrofuranone as a colorless glass.

$^1$H NMR (mixture of diasteriomers) (CDCl$_3$): 5.75 (brs, 1H, sharpens to 2S, 5.81 and 5.69 on D$_2$O exchange); 5.15 (brm, 1H, sharpens to 2 m, 5.20 and 5.19 and 1s, 4.83 on D$_2$O exchange), 2.4 (m, 3H); 2.08 and 2.06 (2 s, 3H); 1.3 (m); 0.88 (t, J=6.6 Hz, 3H).

$^{13}$C NMR (mixture of diasteriomers) (CDCl$_3$): 176.0, 171.1, 101.1, 73.1 and 72.3, 60.5, 46.2, 32.4, 31.8, 30.8, 29.6, 29.4, 29.3, 29.25, 29.20, 29.0, 28.6, 25.2, 22.6, 20.8, 14.0.

m/z Calculated for C$_{22}$H$_{43}$O$_5$Si .(M=TMS): 415.2880, obtained (CI+): 415.2897.

EXAMPLE 31

4-[1-(4-Phenylbutanoyloxy)tridecyl]-2-trimethylsilylfuran tert-Butyl lithium (a 1.7M solution in pentane; 0.47 ml, 0.79 mmol) was added dropwise to a solution of 4-(1-hydroxytridecyl)-2-trimethylsilylfuran (256.4 mg, 0.76 mmol), prepared as in Example 38, in tetrahydrofuran (5 ml) at −78° under argon. After 10 minutes, a solution of 4-phenylbutyryl chloride (145 mg, 0.79 mmol) was added. Stirring was continued at room temperature for 2 days and the mixture was quenched with water. Extraction and evaporation of the dried (magnesium sulphate) extracts gave an oil, which was purified by preparative thin-layer chromatography (20×20 cm, 1000μ silica plate; developed with 10% ethyl ether/hexane). The title ester was obtained as a light yellow oil.

$^1$H NMR (CDCl$_3$): 0.28 (s, 9H), 0.91 (t, 3H, J=7.0 Hz), 1.28 (m, 20H), 1.85 (m, 2H), 1.97 (p, 2H, J=7.7 Hz), 2.35 (t, 2H, J=7.4 Hz), 2.65 (t, 2H, J=7.8 Hz), 5.82 (t, 1H, J=6.9 Hz), 6.61 (s, 1H), 7.25 (m, 2H) and 7.62 (s, 1H).

MS m/e (% abundance) 485 (M$^+$, 7), 339 (28), 321 (32), 170 (12), 154 (19), 153 (18), 147 (84), 91 (46) and 73 (100).

4-[1-(4-Phenylbutanoyloxy)tridecyl]-5-hydroxy-2(5H)-furanone

A mixture of 4-[1-(4-phenylbutanoyloxy) tridecyl]-2-trimethylsilylfuran (203 mg, 0.42 mmol) and Rose Bengal (5 mg) in tetrahydrofuran (7 ml) was exposed to singlet oxygen at −78° for 100 minutes. The residue, after solvent removal, was purified by preparative TLC (20×20 cm, 500 μ silica plate; developed with 60% ethyl ether/hexane). The title furanone was isolated as a colorless oil.

$^1$H NMR (CDCl$_3$): 0.93 (t, 3H, J=6.4 Hz), 1.30 (brs, 20H), 1.95 (br, 2H), 2.03 (p, 2H, J=7.5 Hz), 2.43 (t, 2H, J=7.3 Hz), 2.71 (t, 2H, J=7.4 Hz), 5.45 (br, 1H), 5.99 (brs, 1H), 6.05 (brs, 1H), 5.25 (br, 1H), 6.20 (br, 1H) and 7.30 (m, 5H).

$^{13}$C NMR (CDCl$_3$): 14.1, 22.7, 25.0, 26.2, 29.1, 29.3, 29.5, 29.6, 31.9, 33.2, 33.4, 35.0, 69.0, 69.6, 98.0, 118.5, 119.1, 126.2, 128.4, 140.9, 167.2, 169.7 and 173.6.

MS m/e: exact mass calculated for C$_{27}$H$_{44}$NO$_5$ (M+NH$_4$)$^+$462.3219, found 462.3220.

EXAMPLE 32

4-[1-(3-Phenylpropanoyloxy(tridecyl]-2-trimethylsilylfuran tert-Butyl lithium (a 1.7M solution in pentane; 0.25 ml, 0.42 mmol) was added dropwise to a solution of 4-(1-hydroxytridecyl)-2-trimethylsilylfuran (118 mg, 0.35 mmol) in tetrahydrofuran (6 ml) at −78° under argon. After 25 minutes, a solution of hydrocinnamoyl chloride (62.2 μl, 0.42 mmol) in tetrahydrofuran (½ ml) was added. Stirring was continued at room temperature for 7 hours and quenched with water. Extraction (ethyl ether) and evaporation of the dried (magnesium sulphate) extracts gave an oil, which was purified by preparative TLC (20×20 cm, 500 μ silica plate; developed with 60% ethyl ether/hexane). The title ester was obtained as a colorless oil.

$^1$H NMR (CDCl$_3$): 0.27 (s, 9H), 0.93 (t, 3H), 1.27 (brs, 20H), 1.85 (m, 2H), 2.65 (t, 2H, J=6.9 Hz), 2.96 (2H, t, J=6.9 Hz), 5.80 (t, 1H, J=7.5 Hz), 6.57 (s, 1H), 7.17–7.32 (m, 5H) and 7.57 (s, 1H).

MS m/e (% abundance) 456 (M$^+$, 8), 338 (30), 321 (15), 247 (5), 193 (9), 153 (17), 91 (56) and 73 (100).

4-[1-(3-Phenylpropanoyloxy)tridecyl]-5-hydroxy-2(5H)-furanone

A mixture of 4-[1-(3-phenylpropanoyloxy) tridecyl]-2-trimethylsilylfuran (70 mg, 0.15 mmol) and Rose Bengal (5 mg) in tetrahydrofuran (7 ml) was exposed to singlet oxygen at −78° for 80 minutes. The residue, after solvent removal, was purified by preparative TLC (20×20 cm, 500 μ silica plate; developed with 60% ethyl ether/hexane). The title furanone was isolated as a light yellow oil.

$^1$H NMR (mixture of diasteriomers) (CDCl$_3$): 0.87 (t, 3H, J=6.9 Hz), 1.26 (brs, 20H), 1.72 (m, 2H), 2.73 (brt, 2H), 2.97 (t, 2H, J=7.2 Hz), 4.77 (br, 1H), 5.30 (brt, 1H), 5.48 (brt, 1H), 5.65 (s, 1H), 5.85 (s, 1H), 5.90 (s, 1H), 5.95 (s, 1H) and 7.25 (m, 5H).

$^{13}$C NMR (mixture of diasteriomers) (CDCl$_3$): 14.1, 22.7, 24.8, 25.9, 28.9, 29.1, 29.3, 29.5, 29.6, 30.6, 30.8, 31.7, 31.8, 31.9, 32.7, 32.9, 33.1, 35.3, 35.4, 35.6, 53.3, 69.7, 97.9, 118.5, 126.7, 128.2, 128.6, 139.8, 166.8 and 169.7.

MS m/e: exact mass calculated for C$_{26}$H$_{42}$NO$_5$ (M+NH$_4$)$^+$448.3062, found 448.3052.

EXAMPLE 33

4-[1-(Phenylacetoxy)tridecyl]-2-trimethylsilylfuran tert-Butyl lithium (a 1.7M solution in pentane; 0.29 ml, 0.49 mmol) was added dropwise to a solution of 4-(1-hydroxytridecyl)-2-trimethylsilylfuran (138.2 mg, 0.41 mmol) in tetrahydrofuran (7 ml) at −78° under argon. After 25 minutes, a solution of phenylacetyl chloride (65 μl, 0.49 mmol) in tetrahydrofuran (½ ml) was added. Stirring was continued at room temperature for 16 hours and quenched with water. Extraction (ethyl ether) and evaporation of the dried (magnesium sulphate) extracts gave an oil, which was purified by preparative TLC (20×20 cm, 500 μ silica plate; developed with 10% ethyl ether/hexane). The title ester was obtained as a pale yellow oil.

$^1$H NMR (CDCl$_3$): 0.25 (s, 9H), 0.89 (t, 3H, J=7.0 Hz), 1.27 (brs, 20H), 1.85 (m, 2H), 3.75 (dd, 2H), 5.80 (m, 1H), 6.52 (2s, 2H), 7.20 (m, 5H), 7.52 (s, 1H) and 7.54 (s, 1H).

MS m/e (% abundance) 456 (M$^+$, 8), 338 (30), 321 (15), 247 (5), 193 (9), 153 (17), 91 (56) and 73 (100).

4-[1-(Phenylacetoxy)tridecyl]-5-hydroxy-2(5H)-furanone

A mixture of 4-[1-(phenylacetoxy)tridecyl]-2-trimethylsilylfuran (60 mg, 0.13 mmol) and Rose Bengal (5 mg) in tetrahydrofuran (5 ml) was exposed to singlet oxygen at −78° for 2 hours. The residue, after solvent removal, was purified by preparative TLC (20×20 cm, 500 μ silica plate; developed with 60% ethyl ether/hexane). The title furanone was isolated as a yellow oil.

$^1$H NMR (mixture of diasteriomers and enol forms) (CDCl$_3$): 0.91 (t, 3H, J=6.3 Hz), 128 (brs, 20H), 1.85 (m, 2H), 3.65 (brs, 2H), 5.40–6.20 (m, 4H) and 7.40 (m, 5H).

$^{13}$C NMR (mixture of diasteriomers and enol forms) (CDCl$_3$): 14.1, 22.7, 24.5, 24.7, 24.9, 28.8, 29.1, 29.3, 29.5, 29.6, 31.9, 32.9, 33.1, 33.2, 41.4, 43.6, 48.5, 53.4, 69.5, 70.0, 70.1, 97.3, 97.7, 97.8, 118.4, 119.2, 126.0, 126.1, 126.3, 126.9, 127.1, 127.2, 127.5, 127.6, 128.3, 128.5, 128.7, 128.8, 129.0, 129.2, 129.4, 129.5, 129.8, 129.9, 130.0, 131.3, 166.7, 169.5 and 171.6.

MS m/e: exact mass calculated for $C_{25}H_{40}NO_5$ $(M+NH_4)^+$ 434.2906, found 434.2914.

EXAMPLE 34

4-[1-(Cyclohexanoyloxy)tridecyl]-2-trimethylsilylfuran tert-Butyl lithium (a 1.7M solution in pentane; 0.33 ml, 0.55 mmol) was added dropwise to a solution of 4-(1-hydroxytridecyl)-2-trimethylsilylfuran (170 mg, 0.50 mmol) in tetrahydrofuran (5 ml) at 0° under argon. After 10 minutes, cyclohexanecarboxylic acid chloride (74 μl, 0.55 mmol) was added. The mixture was stirred at room temperature for 15 hours and quenched with water. Extraction and evaporation of the dried (magnesium sulphate) extracts gave an oil, which was purified by preparative TLC (20×20 cm, 1000μ silica plate; developed with 5% ethyl ether/hexane). The title ester was obtained as a pale yellow oil.

$^1$H NMR (CDCl$_3$): 0.23 (s, 9H), 0.94 (t, 3H, J=6.9 Hz), 1.31 (br, 20H), 1.21 (m, 12H), 2.35 (tt, 1H, J=11.3 Hz, 3.7 Hz), 5.82 (t, 1H, J=7.5 Hz), 6.61 (s, 1H), and 7.62 (s, 1H).

MS m/e (% abundance) 448 (M+, 12), 339 (18), 338 (67), 337 (20), 185 (12), 170 (10), 154 (13), 153 (13), 111 (33), 84 (11), 83 (100) and 73 (71).

4-[1-(Cyclohexanoyloxy)tridecyl]-5-hydroxy-2(5H)-furanone

A mixture of 4-[1-(cyclohexanoyloxy)tridecyl]-2-trimethylsilylfuran (70 mg, 0.16 mmol) and Rose Bengal (5 mg) in tetrahydrofuran (6 ml) was exposed to singlet oxygen at −78° for 2 hours. The residue, after solvent removal, was purified by preparative TLC (20×20 cm, 1000μ silica plate; developed with 60% ethyl ether/hexane). The title furanone was obtained as a colorless oil.

$^1$H NMR (CDCl$_3$): 0.91 (t, 3H, J=6.8 Hz), 1.29 (m, 6H), 1.70-2.00 (m, 6H), 2.40 (m, 1H), 5.45 (br, 2H), 5.98 (br, 1H) and 6.05 (br, 1H).

$^{13}$C NMR (CDCl$_3$): 14.1, 22.7, 25.1, 25.3, 25.6, 28.8, 28.9, 29.2, 29.4, 29.5, 29.7, 31.9, 33.3, 43.1, 68.7, 69.3, 98.1, 118.3, 119.0 and 167.6.

MS m/e: exact mass calculated for $C_{24}H_{41}O_5$ $(M+H)^+$ 409.2953, found 409.2971.

EXAMPLE 35

4-[1-(Dodecanoyloxy)tridecyl]-2-trimethylsilylfuran tert-Butyl lithium (a 1.7M solution in pentane; 0.21 ml, 0.36 mmol) was added dropwise to a solution of 4-(1-hydroxytridecyl)-2-trimethylsilylfuran (124.5 mg, 0.37 mmol) in tetrahydrofuran (5 ml) at 0° under argon. After 5 minutes, the cooling bath was removed and lauroyl chloride (88 μl) was added. The mixture was stirred at room temperature for 16 hours and quenched with water. Extraction (ethyl ether) and evaporation of the dried (magnesium sulphate) extracts gave an oil, which was purified by preparative TLC (20×20 cm, 1000μ silica plate; developed with 5% ethyl ether/hexane). The title ester was obtained as a colorless oil.

$^1$H NMR (CDCl$_3$): 0.23 (s, 9H), 0.88 (t, 3H, J=6.9 Hz), 1.25 (brs, 36H), 1.57-1.92 (m, 2H), 2.29 (t, 2H, J=7.2 Hz), 5.77 (t, 1H, J=7.5 Hz), 6.57 (s, 1H) and 7.57 (s, 1H).

MS m/e (% abundance) 520 (M+, 9), 338 (45), 320 (18), 257 (10), 183 (16), 170 (10), 154 (25), 73 (100).

4-[1-(Dodecanoyloxy)tridecyl]-5-hydroxy-2(5H)-furanone

A mixture of 4-[1-(dodecanoyloxy)tridecyl]-2-trimethylsilylfuran (55 mg, 0.11 mmol) and Rose Bengal (5 mg) in tetrahydrofuran (7 ml) was exposed to singlet oxygen at −78° for 2 hours. The residue, after solvent removal, was purified by preparative TLC (20×20 cm, 500μ silica plate; developed with 60% ether/hexane). The title furanone was obtained as a colorless oil.

$^1$H NMR (CDCl$_3$): 0.92 (t, 6H, J=6.4 Hz), 1.29 (brs, 38H), 1.60-1.90 (m, 2H), 2.40 (t, 2H, J=7.4 Hz), 5.40 (br, 1H) and 6.02 (br, 2H).

$^{13}$C NMR (mixture of diasteriomers) (CDCl$_3$): 14.0, 14.1, 15.2, 22.7, 24.7, 24.9, 25.0, 25.4, 25.6, 27.9, 28.1, 28.2, 28.3, 28.5, 28.6, 28.7, 28.8, 28.9, 29.1, 29.3, 29.5, 29.6, 30.0, 30.2, 30.4, 30.5, 31.9, 33.1, 34.2, 34.3, 53.4, 65.9, 68.0, 69.3, 69.4, 69.5, 98.0, 118.3, 167.0, 170.0 and 173.5.

MS m/e: exact mass calculated for $C_{29}H_{53}O_5$ $(M+H)^+$ 481.3893, found 481.3895.

EXAMPLE 36

4-[1-(Methylcarbamoyl)tridecyl]-2-trimethylsilylfuran tert-Butyl lithium (a 1.7M solution in pentane; 0.21 ml, 0.36 mmol) was added dropwise to a solution of 4-(1-hydroxytridecyl)-2-trimethylsilylfuran (110 mg, 0.33 mmol) in tetrahydrofuran (5 ml) at 0° under argon. After 10 minutes, a solution of methyl isocyanate (21μl, 0.36 mmol) in tetrahydrofuran (½ ml) was added. Stirring was continued at room temperature for 2 days and the mixture was quenched with water. Extraction (ethyl ether) and evaporation of the dried (magnesium sulphate) extracts gave a © oi<Å which was purified by preparative TLC 20×20 cmÅ 1000μ silica plate; developed with 20% ethyl ether/hexane). The title carbamate was obtained as a yellow oil.

$^1$H NMR (CDCl$_3$): 0.27 (s, 9H), 0.91 (t, 3H, J=6.9 Hz), 1.28 (brs, 20H), 1.85 (m, 2H), 2.81 (d, 3H, J=4.9 Hz), 4.60 (br, 1H), 5.70 (t, 1H, J=7.5 Hz), 6.61 (s, 1H) and 7.62 (s, 1H).

MS m/e (% abundance) 395 (M+, 3), 339 (19), 338 (71), 320 (16), 183 (17), 169 (15), 154 (25), 132 (11), 75 (25) and 73 (100).

4-[1-(Methylcarbamoyl)tridecyl]-5-hydroxy-2(5H)-furanone

A mixture of 4-[1-(methylcarbamoyl)tridecyl]-2-trimethylsilylfuran (12.5 mg, 0.03 mmol) and Rose Bengal (2 mg) in tetrahydrofuran (5 ml) was exposed to singlet oxygen at −78° for 80 minutes. The residue, after solvent removal, was purified by preparative TLC (20×20 cm, 250μ silica plate; developed with 70% ethyl ether/hexane). The title furanone was obtained as a pale yellow oil.

$^1$H NMR (mixture of diasteriomers) (CDCl$_3$): 0.91 (t, 3H, J=6.8 Hz), 1.29 (brs, 20H), 1.80 (m, 2H), 2.83 (d, 3H, J=4.9 Hz), 2.90 (d, 3H, J=4.9 Hz), 4.80 (br, 1H), 4.95 (bd, 1H), 5.25 (brt, 1H), 5.45 (brt, 1H), 6.01 (brs, 1H) and 6.04 (brs, 1H).

$^{13}$C NMR (mixture of diasteriomers) (CDCl$_3$): 14.1, 22.7, 25.1, 27.6, 29.2, 29.4, 29.5, 29.6, 31.9, 33.2, 33.7, 69.7, 69.9, 97.9, 98.5, 118.4, 118.9, 156.7, 168.4 and 169.9.

MS m/e exact mass calculated for $C_{19}H_{33}NO_5$ $(M+NH_4)^+$ 373.2702, found 373.2711.

EXAMPLE 37

4-[1-((R)-(+)-α-Methylbenzylcarbamoyl) tridecyl]-2-trimethylsilylfuran tert-Butyl lithium (a 1.7M solution in pentane; 0.59 ml, 1.0 mmol) was added dropwise to a solution of 4-(1-hydroxytridecyl)-2-trimethylsilylfuran (335.5 mg, 0.99 mmol) in tetrahydrofuran (6 ml) at 0° under argon. After 20 minutes, a solution of (R)-(+)-α-methylbenzyl isocyanate (146 mg, 0.99 mmol) in THF (½ ml) was added. Stirring was continued for 16 hours while the cooling bath attained room temperature. The mixture was quenched with water and extracted with ethyl ether. Evaporation of the dried (magnesium sulphate) extracts gave an oil, which was purified by preparative TLC (20×20 cm, two 1000μ silica plates; developed with 20% ethyl ether/hexane). The title carbamate was obtained as a light yellow oil.

$^1$H NMR (CDCl$_3$): 0.30 (2s, 9H), 0.92 (brt, 3H), 1.29 (brs, 28H), 1.80 (br, 2H), 4.85-5.00 (2 brs, 2H), 5.68 (t, 1H, J=7.5 Hz), 6.60 (s, 1H), 6.70 (s, 1H), and 7.30 (m, 5H).

MS m/e (% abundance) 503 (M+NH$_4$+), 0.1), 485 (M+, 0.2), 442 (1), 322 (33), 321 (100), 320 (4), 238 (4), 183 (5), 122 (8) and 106 (4).

4-[1-((R)-(+)-α-Methylbenzylcarbamoyl) tridecyl]-5-hydroxy-2(5H)-furanone

A mixture of 4-[1-((R)-(+)-α-methylbenzylcarbamoyl)tridecyl]-2-trimethylsilylfuran (71 mg, 0.15 mmol) and Rose Bengal (5 mg) in tetrahydrofuran (5 ml) was exposed to singlet oxygen at −78° for 2 hours. The residue, after solvent removal, was purified by preparative TLC (20×20 cm, 500μ silica plate; developed with 60% ethyl ether/hexane). The title furanone was obtained as a pale yellow oil.

$^1$H NMR (mixture of diasteriomers) (CDCl$_3$): 0.91 (t, 3H, J=7.0 Hz), 1.28 (brs, 18H), 1.38 (d, 3H, J=7.0 Hz), 1.50 (m, 2H), 1.78 (m, 2H), 4.80 (brm, 1H), 5.26 (m, 1H), 5.38 (m, 1H), 5.98 (brs, 1H), 6.05 (brs, 1H) and 7.35 (m, 5H).

$^{13}$C NMR (mixture of diasteriomers) 14.1, 15.3, 17.9, 22.1, 22.3, 22.7, 25.0, 29.0, 29.1, 29.3, 29.5, 29.6, 31.9, 33.2, 33.4, 33.6, 51.0, 63.8, 69.8, 69.9, 97.9, 98.3, 98.4, 104.2, 118.3, 118.4, 118.8, 125.7, 125.8, 125.9, 127.7, 128.8, 142.7, 155.3, 161.8, 169.8 and 169.9.

MS m/e: exact mass calculated for C$_{25}$H$_{36}$NO$_5$ (M+—CH$_3$): 430.2593, found 430.2603.

EXAMPLE 38

4-(1-Trichloroacetoxy)tridecyl-2-trimethylsilylfuran tert-Butyl lithium (a 1.7M solution in pentane; 0.32 ml, 0.54 mmol) was added dropwise to a solution of 4-(1-hydroxytridecyl)-2-trimethylsilylfuran (151.3 mg, 0.45 mmol) in tetrahydrofuran (10 ml) at 0° under argon. After 10 minutes trichloroacetic anhydride (98 μl, 0.54 mmol) was added and stirring was continued at room temperature overnight. The mixture was quenched with water and extracted with ethyl ether. Evaporation of the dried (magnesium sulphate) extracts afforded an oil, which was purified by preparative TLC (20×20 cm, 500μ silica plate; developed with 10% ethyl ether/petroleum ether). The title ester was obtained as a pale yellow oil.

$^1$H NMR (CDCl$_3$): 0.28 (s, 9H), 0.91 (t, 3H, J=6.0 Hz), 1.28 (brs, 20H), 2.0 (m, 2H), 5.88 (t, 1H, J=7.5 Hz), 6.64 (s, 1H) and 7.70 (s, 1H).

MS m/e (% abundance) 460/462/464 ((M+NH$_4$)+, 16, 16, 5), 426 (13), 316 (21), 300 (69), 299 (21) and 298 (100).

4-(1-Trichloroacetoxy)tridecyl-5-hydroxy-2(5H)-furanone

A mixture of 4-(1-trichloroacetoxy)tridecyl-2-trimethylsilylfuran (120 mg, 0.25 mmol) and Rose Bengal (5 mg) in tetrahydrofuran (5 mg) was exposed to singlet oxygen at −78° for ½ hour. The residue, after solvent removal, was purified by preparative TLC (20×20 cm, 500μ silica plate; developed with 60% ethyl ether/hexane). The title furanone was obtained as a light yellow oil.

$^1$H NMR (CDCl$_3$): 0.92 (t, 3H, J=7.0 Hz), 1.29 (brs, 20H), 2.02 (br, 2H), 5.75 (br, 1H), 6.18 (brs+s, 2H).

$^{13}$C NMR (CDCl$_3$): 14.1, 22.7, 24.6, 28.8, 29.0, 29.3, 29.4, 29.5, 29.6, 29.9, 31.7, 31.9, 32.7, 74.6, 89.5, 97.6, 119.1, 161.1, 164.5 and 169.8.

MS m/e: exact mass calculated for C$_{19}$H$_{33}$Cl$_3$NO$_5$ (M+NH$_4$)+460.1424, found 460.1403.

EXAMPLE 39

5-Palmitoyloxy-4-(1-acetoxytridecyl)-2(H)-furanone

To a stirred solution of palmitoyl chloride (41 mg, 0.15 mmole) in THF (2 ml) at 0° C., was added 4-(1-acetoxytridecyl)-5-hydroxy-2(5H)-furanone (30 mg, 0.088 mmole), prepared as in Example 41, and triethylamine (15 mg, 0.15 mmole). The flask was warmed to room temperature until no starting material remained (as monitored by TLC). The solution was diluted with pentane, then washed with water. The aqueous portion was extracted with ethyl ether and the combined organic portions were dried over magnesium sulfate, filtered, concentrated and purified by preparative TLC (20×20 cm, 250μ silica plate; developed with 30% ethyl ether/hexane). The titled furanone was obtained as a colorless solid.

$^1$H NMR (CDCl$_3$): 7.02 (s, 1H), 6.95 (s, 1H), 6.12 (s, 1H), 6.08 (s, 1H), 5.65 (t, J=3.75, 1H), 5.54 (t, J=3.75, 1H), 2.4 (t, J=7.5 Hz, 2H), 2.35 (t, J=7.5 Hz, 2H), 2.1 (s, 3H), 2.05 (s, 3H), 1.82 (m, 2H), 1.63 (m, 2H), 1.25 (m, 46H), 0.85 (m, 6H).

$^{13}$C NMR (CDCl$_3$): 172, 170, 169, 164.6, 120, 119, 92.6, 92, 69, 68, 66, 33.9, 33.8, 33.1, 29.5, 29.3, 29.2, 29.1, 28.9, 24.7, 24.5, 22.7, 20.7, 15.2, 14.1.

MS m/e=exact mass calculated for C$_{35}$H$_{62}$O$_6$ 578.4546 (M+), found 578.4560.

EXAMPLE 40

Ethyl 9-phenylnonanoate

To (E)-ethyl 9-phenyl-2,6-nonadienoate (0.798 g, 3.09 mmol) in ethyl acetate (5 ml) was added 10% palladium on carbon (0.013 g). This mixture was subjected to one atmosphere of hydrogen at room temperature with stirring for 12 hours. The reaction mixture was filtered and concentrated to give the desired saturated ester which was carried on without further purification.

IR (CHCl$_3$): 2930, 2860, 1720 cm$^{-1}$.

$^1$H NMR (CDCl$_3$): 7.0 to 7.2 (m, 5H); 4.01 (q, J=7.0 Hz, 2H); 2.49 (t, J=7.8 Hz, 2H); 2.17 (t, J=7.6 Hz, 2H); 1.4 to 1.6 (m, 4H); 1.18 to 1.30 (m, 8H); 1.13 (t, J=7.1 Hz, 3H).

$^{13}$C NMR (CDCl$_3$): 173.5, 142.6, 128.2, 128.0, 127.8, 125.4, 59.9, 35.8, 34.2, 31.3, 29.1, 29.0, 28.9, 28.7, 24.8, 14.1.

m/z Calculated for $C_{17}H_{26}O_2$ (M+): 262.1933, obtained (EI+): 262.1933.

9-Phenylnonan-1-ol

To a stirred solution of ethyl 9-phenylnonanoate (0.884 g, 3.37 mmol) in methylene chloride (10 ml) under argon at 0° was added diisobutylaluminum hydride (8.43 ml of a 1.0M solution). This mixture was warmed to room temperature and quenched with 10% aqueous hydrochloric acid. The organic portion was washed with 5% sodium bicarbonate, water, saturated sodium chloride solution, dried over magnesium sulfate, filtered and concentrated to give the desired alcohol which was carried on without further purification.

IR (CHCl$_3$): 3610, 3440 (broad), 2910 cm$^{-1}$.

'H NMR (CDCl$_3$): 7.10 to 7.30 (m, 5H); 3.59 (t, J=6.7 Hz, 2H); 2.59 (t, J=7.7 Hz, 2H); 1.6 (broad s, 1H); 1.45 to 1.75 (m, 4H); 1.29 (m, 10H).

$^{13}$C NMR (CDCl$_3$): 142.8, 128.3, 128.1, 125.5, 62.8, 35.9, 32.7, 31.4, 29.4, 29.3, 29.2, 25.6.

m/z Calculated for $C_{15}H_{24}O$ (M+): 220.1827, obtained (EI+): 220.1831.

1-Bromo-9-phenylnonane

To 1,2 bis(diphenylphosphino)ethane (1.53 g, 3.84 mmol) in methylene chloride (25 ml) at 0° was added bromine (1.23 g, 7.68 mmol) in methylene chloride (4 ml) and stirred for 15 minutes. To this mixture was added 9-phenylnonan-1-ol (0.705 g, 3.20 mmol) in methylene chloride (5 ml). The reaction mixture was allowed to warm to room temperature, stirred for 1 hour and quenched by the addition of ethyl ether/pentane (1:2). This mixture was filtered through silica and concentrated to give the desired bromide which was carried on without further purification.

IR (CHCl$_3$): 3028, 2910, 2850 cm$^{-1}$.

'H NMR (CDCl$_3$): 7.10 to 7.30 (m, 5H); 3.35 (t, J=6.8 Hz, 2H); 2.58 (t, J=7.8 Hz, 2H); 1.75 to 1.87 (m, 2H); 1.55 to 1.67 (m, 2H); 1.20 to 1.45 (m, 10H).

$^{13}$C NMR (CDCl$_3$): 142.7, 128.3, 128.1, 125.5, 35.9, 33.8, 32.8, 31.4, 29.3, 29.2, 28.7, 28.1, 28.0.

m/z Calculated for $C_{15}H_{23}Br$ (M+): 282.0983, obtained (EI+): 282.0976.

4-(1-Hydroxy-10-phenyldecyl)-2-trimethylsilylfuran

To a stirred solution of 9-phenylnonylmagnesium bromide (1.35 mmol, prepared from 0.383 g, 1.35 mmol of 1-bromo-9-phenylnonane and 4.11 mmol magnesium) in tetrahydrofuran (5 ml) at 0° under argon was added dropwise, 5-trimethylsilyl-3-furaldehyde (0.227 g, 1.35 mmol) in tetrahydrofuran (3 ml). The solution was warmed to room temperature and stirred for 30 minutes, quenched with 5% ammonium chloride and extracted into ethyl ether. The organic portion was washed with saturated sodium bicarbonate, water, saturated sodium chloride solution, dried over magnesium sulfate, filtered and concentrated to give a yellow oil. Purification by flash chromatography (silica, 5 to 20% ethyl acetate/hexane) gave the desired alcohol.

IR (CHCl$_3$): 3620, 3450 (broad), 2930, 1250 cm$^{-1}$.

'H NMR (CDCl$_3$): 7.51 (s, 1H); 7.10 to 7.30 (m, 5H); 6.61 (s, 1H); 4.58 (t, J=6.7 Hz, 1H); 2.58 (t, J=7.8 Hz, 2H); 2.01 (s, 1H); 1.65 to 1.80 (m, 2H); 1.53 to 1.65 (m, 2H); 1.20 to 1.45 (m, 12H); 0.25 (s, 9H).

$^{13}$C NMR (CDCl$_3$): 161.2, 143.1, 142.8, 129.2, 128.3, 128.2, 125.5, 118.3, 66.8, 37.9, 35.9, 31.4, 29.5, 29.3, 25.7, −1.7.

m/z Calculated for $C_{23}H_{36}O_2Si$ (M+): 372.2485, obtained (EI+): 372.2496.

4-(1-Acetoxy-10-phenyldecyl)-2-trimethylsilylfuran

A solution of 4-(1-hydroxy-10-phenyldecyl)-2-trimethylsilylfuran (0.178 g, 0.478 mmol), acetic anhydride (0.5 ml) and pyridine (0.081 g, 0.956 mmol) was stirred at room temperature until no starting material was visible by TLC. The reaction mixture was taken up in ethyl ether, washed repeatedly with saturated sodium bicarbonate, aqueous cupric sulfate solution, water, saturated sodium chloride solution, dried over magnesium sulfate, filtered and concentrated to give the desired acetate which was carried on without further purification.

IR (CHCl$_3$): 2920, 1720, 1250 cm$^{-1}$.

'H NMR (CDCl$_3$): 7.58 (s, 1H); 7.10 to 7.30 (m, 5H); 6.59 (s, 1H); 5.77 (t, J=6.8 Hz, 1H); 2.58 (t, J=7.6 Hz, 2H); 2.01 (s, 3H); 1.70 to 1.95 (m, 2H); 1.54 to 1.68 (m, 2H); 1.15 to 1.39 (m, 12H); 0.24 (s, 9H).

$^{13}$C NMR (CDCl$_3$): 170.3, 161.0, 144.4, 142.7, 128.3, 128.1, 125.5, 124.9, 118.6, 68.5, 35.9, 34.7, 31.4, 29.4, 29.2, 25.4, 21.1, −1.8.

m/z Calculated for $C_{25}H_{38}O_3Si$ (M+): 414.2590, obtained (EI+): 414.2610.

4-(1-Acetoxy-10-phenyldecyl)-5-hydroxy-2(5H)-furanone

A stirred solution of 4-(1-acetoxy-10-phenydecyl)-2-trimethylsilylfuran (0.167 g, 0.403 mmol) and Rose Bengal (3 mg) in acetone (25 ml) was flushed with oxygen and cooled to −78°. The solution was subsequently irradiated with a 150 watt flood lamp while under constant positive pressure of oxygen until starting material was no longer visible by TLC. The solution was warmed to room temperature and concentrated to a red oil (0.198 g). Purification by flash chromatography (silica, 20 to 40% ethyl acetate/hexane) gave the desired hydroxybutenolide.

IR (CHCl$_3$): 3380 (broad), 3050, 2920, 2850, 1700 (broad) cm$^{-1}$.

'H NMR (CDCl$_3$): (mixture of diastereomers): 7.15 to 7.35 (m, 5H); 6.10 (brs, 1H); 5.96 (s, 1H); 5.78 (brs, 1H); 5.55 (brs, 1H); 2.59 (t, J=7.7 Hz, 2H); 2.11 (s, 3H); 1.69 to 1.90 (m, 2H); 1.50 to 1.67 (m, 2H); 1.15 to 1.40 (m, 12H).

$^{13}$C NMR (CDCl$_3$): (mixture of diastereomers): 170.8, 170.4, 166.9, 142.7, 128.3, 128.1, 125.4, 118.4 and 118.2, 98.0, 69.5, 35.8, 32.8, 31.3, 29.3, 29.2, 29.1, 29.0, 24.8, 20.7.

m/z Calculated for $C_{22}H_{34}O_5N$ (M+NH$_4^+$): 392.2437, obtained (CI+): 392.2426.

EXAMPLE 41

5-Phenylpent-1-en-3-ol

To vinyl magnesium bromide (550 ml of a 1.0M solution) was added 3-phenylpropionaldehyde (36.68 g, 0.273 mol) in tetrahydrofuran (300 ml) under argon at 0°. This mixture was stirred for one hour at room temperature, quenched with aqueous ammonium chloride and ice, and extracted into ethyl ether. The organic portion was washed with 5% sodium bicarbonate, water, saturated sodium chloride solution, dried over magnesium sulfate, filtered and concentrated to give the desired alcohol which was carried on without further purification.

(E)-Ethyl 7-phenyl-4-heptenoate

A mixture of 5-phenylpent-1-en-3-ol (11.48 g, 70.9 mmol), triethylorthoacetate (80.47 g, 496.0 mmol) and p-toluenesulfonic acid (0.81 g, 4.25 mmol) was refluxed under argon for 5.5 hours. The reaction mixture was cooled to room temperature, diluted with water and stirred for an additional 1.5 hours. This mixture was partitioned between an aqueous saturated sodium bicarbonate solution and ethyl ether. The organic layer was washed with water, dried over magnesium sulfate, filtered and concentrated to give a yellow oil (14.57 g). Purification by flash chromatography (silica, 3% ethyl acetate/hexane) gave the desired ester.

IR (CHCl$_3$): 3028, 2930, 1736 cm$^{-1}$.

'H NMR (CDCl$_3$): 7.1 to 7.3 (m, 5H); 5.35 to 5.55 (m, 2H); 4.13 (q, J=7.4 Hz, 2H); 2.64 (t, J=7.3 Hz, 2H); 2.2 to 2.4 (m, 6H); 1.23 (t, J=6.5 Hz, 3H).

$^{13}$C NMR (CDCl$_3$): 173.0, 141.8, 130.6, 128.7, 128.3, 128.2, 125.7, 60.1, 35.9, 34.2, 27.8, 14.2.

m/z Calculated for C$_{15}$H$_{20}$O$_2$ (M+): 232.1463, obtained (EI+): 232.1463.

(E), (E)-Ethyl 9-phenyl-2,6-nonadienoate and (E), (Z)-Ethyl 9-phenyl-2,6-nonadienoate To triethylphosphonoacetate (12.38 g, 55.2 mmol) in tetrahydrofuran (500 ml) at −78° under argon was added n-butyl lithium (36.90 ml of a 1.53M solution) followed after 20 minutes by (E)-ethyl 7-phenylhept-4-enoate (12.60 g, 54.28 mmol) in tetrahydrofuran (60 ml). After one hour stirring at −78°, diisobutylaluminum hydride (54.28 ml of a 1.0M solution) was added dropwise. The mixture was slowly warmed and allowed to stir at room temperature for 15 hours. The reaction was quenched with aqueous sodium sulfate, filtered and concentrated. The residue was taken up in ethyl ether, washed with saturated sodium bicarbonate, water, saturated sodium chloride solution, dried over magnesium sulfate, filtered and concentrated to give a pale oil. Purification by flash chromatography (silica, 3 to 5% ethyl acetate/hexane) gave the desired trans, trans-unsaturated ester and a mixture of cis-trans isomers.

IR (CHCl$_3$): 2930, 1710 cm$^{-1}$.

'H NMR (CDCl$_3$): 7.1-7.3 (m, 5H); 6.94 (dt, J=15.7 Hz, J=7.4 Hz, 1H); 5.80 (d, J=15.7 Hz, 1H); 5.32 to 5.55 (m, 2H); 4.18 (q, J=7.0 Hz, 2H); 2.66 (t, J=7.9 Hz, 2H); 2.10 to 2.35 (m, 6H); 1.28 (t, J=7.1 Hz, 3H).

$^{13}$C NMR (CDCl$_3$): 166.5, 148.4, 141.8, 130.6, 129.1, 128.4, 128.2, 125.7, 121.5, 60.0, 35.9, 34.2, 32.0, 30.9, 14.2.

m/z Calculated for C$_{17}$H$_{22}$O$_2$ (M+): 258.1620, obtained (EI+): 258.1616.

(E)-Ethyl 9-phenylnon-6-enoate

To 1.24 g of magnesium stirring in methanol (85 ml) at 0° was added a cis-trans mixture of (E), (Z)-ethyl 9-phenyl-2,6-nonadienoate (4.14 g, 16.96 mmol) in methanol (15 ml). After the magnesium had been consumed the reaction was quenched with 10% HCl at 0° and extracted with ethyl ether. The organic portions were combined, washed with 5% sodium bicarbonate, water, saturated sodium chloride solution, dried over magnesium sulfate, filtered and concentrated to give a pale oil. Purification by flash chromatography (silica, 3 to 5% ethyl acetate/hexane) gave the desired ester.

IR (CHCl$_3$): 3028, 2935, 1735 cm$^{-1}$.

'H NMR (CDCl$_3$): 7.1 to 7.3 (m, 5H); 5.3 to 5.5 (m, 2H); 4.05 (q, J=7.0 Hz, 2H); 2.63 (t, J=7.8 Hz, 2H); 2.14 to 2.35 (m, 4H); 1.8 to 2.0 (m, 2H); 1.45 to 1.65 (m, 2H); 1.2 to 1.4 (m, 2H); 1.27 (t, J=7.0 Hz, 3H).

(E)-9-Phenylnon-6-en-1-ol

To a stirred solution of (E)-ethyl 9-phenylnon-6-enoate (1.45 g, 5.53 mmol) in methylene chloride (35 ml) under argon at 0° was added diisobutylaluminum hydride (15.0 ml of a 1.0M solution). This mixture was warmed to room temperature and quenched with 10% aqueous hydrochloric acid. The organic portion was washed with saturated sodium bicarbonate solution, water, saturated sodium chloride solution, dried over magnesium sulfate, filtered and concentrated to give a colorless oil. Purification by flash chromatography (silica, 20% ethyl acetate/hexane) gave the desired alcohol.

IR (CDCl$_3$): 3622, 3450 (broad), 3028, 2932 cm$^{-1}$.

'H NMR (CDCl$_3$): 7.07 to 7.27 (m, 5H); 5.30 to 5.50 (m, 2H); 3.53 (t, J=6.6 Hz, 2H); 3.29 (s, 1H); 2.63 (t, J=7.8 Hz, 2H); 2.15 to 2.35 (m, 2H); 1.90 to 2.05 (m, 2H); 1.40 to 1.55 (m, 2H); 1.20 to 1.40 (m, 4H).

$^{13}$C NMR (CDCl$_3$): 141.8, 130.6, 129.2, 128.2, 127.9, 125.4, 62.2, 35.8, 34.2, 32.3, 29.1, 25.0.

m/z Calculated for C$_{15}$H$_{26}$ON (M+NH$_4$)+: 236.2014, obtained (CI+): 236.2024.

(E)-1-Bromo-9-phenylnon-6-ene

To 1,2-bis(diphenylphosphino)ethane (0.918 g, 2.30 mmol) in methylene chloride (12 ml) at 0° was added bromine (0.736 g, 4.60 mmol) in methylene chloride (4 ml) and stirred for 15 minutes. To this mixture was added (E)-9-phenylnon-6-en-1-ol (0.419 g, 1.92 mmol) in methylene chloride (5 ml). The reaction mixture was allowed to warm to room temperature, stirred for 1½ hours and quenched by the addition of ethyl ether/pentane (1:2). This mixture was passed through silica to filter off the solid residues and the filtrate was concentrated to give the desired bromide which was carried on without further purification.

IR (CHCl$_3$): 3000, 2930, 2860 cm$^{-1}$.

'H NMR (CDCl$_3$): 7.13 to 7.33 (m, 5H); 5.35 to 5.52 (m, 2H); 3.38 (t, J=6.9 Hz, 2H); 2.67 (t, J=7.8 Hz, 2H); 2.25 to 2.40 (m, 2H); 1.95 to 2.05 (m, 2H); 1.78 to 1.90 (m, 2H); 1.27 to 1.45 (m, 4H).

$^{13}$C NMR (CDCl$_3$): 142.1, 130.6, 129.8, 128.4, 128.2, 125.7, 36.1, 34.3, 33.8, 32.7, 32.2, 28.6, 27.6.

m/z Calculated for C$_{15}$H$_{21}$Br (M+): 280.0827, obtained (EI+): 280.0822.

(E)-4-(1-Hydroxy-10-phenyldec-7-enyl)-2-trimethylsilylfuran

To a stirred solution of (E)-9-phenylnon-6-enyl magnesium bromide (0.861 mmol, prepared from 0.242 g, 0.861 mmol, of (E)-1-bromo-9-phenylnon-6-ene and 2.88 mmol magnesium) in tetrahydrofuran (10 ml) at 0° under argon was added dropwise, 5-trimethylsilyl-3-furaldehyde (0.145 g, 0.861 mmol) in tetrahydrofuran (5 ml). The solution was warmed to room temperature, stirred for 5 hours, quenched with 5% ammonium chloride and extracted into ethyl ether. The organic portion was washed with 5% sodium bicarbonate, water, saturated sodium chloride solution, dried over magnesium sulfate, filtered and concentrated to give yellow oil. Purification by flash chromatography (silica, 5 to 20% ethyl acetate/hexane) gave the desired alcohol.

IR (CDCl$_3$): 3600, 3440 (broad), 2930, 1250 cm$^{-1}$.

'H NMR (CDCl$_3$): 7.55 (s, 1H); 7.12 to 7.35 (m, 5H); 6.62 (s, 1H); 5.37 to 5.50 (m, 2H); 4.63 (t, J=6.7 Hz, 1H);

2.66 (t, J=7.8 Hz, 2H); 2.25 to 2.40 (m, 2H); 1.90 to 2.05 (m, 2H); 1.60 to 1.80 (m, 3H); 1.20 to 1.50 (m, 6H); 0.25 (s, 9H).

$^{13}$C NMR (CDCl$_3$): 161.4, 143.1, 142.1, 130.9, 129.4, 129.2, 128.4, 128.2, 125.6, 118.2, 67.0, 37.8, 36.1, 34.4, 32.4, 29.4, 28.9, 25.6, −1.7.

m/z Calculated for C$_{23}$H$_{34}$O$_2$Si (M+): 370.2328, obtained (EI+): 370.2332.

(E)-4-(1-Acetoxy-10-phenyldec-7-enyl)-2-trimethylsilylfuran

A solution of 4-(1-hydroxy-10-phenyldec-7-enyl)-2-trimethylsilylfuran (0.136 g, 0.367 mmol), acetic anhydride (1 ml) and pyridine (0.062 g, 0.735 mmol) was stirred at room temperature until no starting material was visible by TLC. The reaction mixture was taken up in ethyl ether, washed repeatedly with saturated sodium bicarbonate solution, aqueous cupric sulfate solution, water, saturated sodium chloride solution, dried over magnesium sulfate, filtered and concentrated to give the desired acetate which was carried on without further purification. [Yield: 0.133 g, 88%.]

IR (CHCl$_3$): 2920, 1720, 1250 cm$^{-1}$.

$^1$H NMR (CDCl$_3$): 7.59 (s, 1H); 7.12 to 7.22 (m, 5H); 6.58 (s, 1H); 5.76 (t, J=7.0 Hz, 1H); 5.35 to 5.49 (m, 2H); 2.66 (t, J=7.8 Hz, 2H); 2.25 to 2.37 (m, 2H); 2.05 (s, 3H); 1.65 to 2.05 (m, 4H); 1.20 to 1.40 (m, 6H); 0.25 (s, 9H).

$^{13}$C NMR (CDCl$_3$): 170.5, 161.2, 144.4, 142.1, 130.9, 129.5, 128.4, 128.2, 125.7, 125.0, 118.6, 68.6, 36.1, 34.7, 34.4, 32.4, 29.3, 28.7, 25.4, 21.3, −1.7.

m/z Calculated for C$_{25}$H$_{36}$O$_3$Si (M+): 412.2434, obtained (EI+): 412.2433.

(E)-4-(1-Acetoxy-10-phenyldec-7-enyl)-5-hydroxy-2(5H)-furanone

A stirred solution of 4-(1-acetoxy-10-phenyldec-7-enyl)-2-trimethylsilylfuran (0.133 g, 0.322 mmol) and Rose Bengal (3 mg) in acetone (10 ml) was flushed with oxygen and cooled to −78°. The solution was subsequently irradiated with a 150 watt flood lamp while under constant positive pressure of oxygen until starting material was no longer visible by TLC. The solution was warmed to room temperature and concentrated to a pink. Purification by flash chromatography (silica, 20 to 40% ethyl acetate/hexane) gave the title compound.

IR (CHCl$_3$): 3400 (broad), 3020, 2920, 1750 cm$^{-1}$.

$^1$H NMR (CDCl$_3$): (mixture of diastereomers): 7.08 to 7.30 (m, 5H); 6.05 (broad s, 1H); 5.97 (s, 1H); 5.67 (broad s, 1H); 5.43 to 5.57 (broad m, 1H); 5.31 to 5.43 (m, 2H); 2.66 (t, J=7.8 Hz, 2H); 2.20 to 2.33 (m, 2H); 2.12 (s, 3H); 1.88 to 2.00 (m, 2H); 1.68 to 1.87 (m, 2H); 1.18 to 1.43 (m, 6H).

$^{13}$C NMR (CDCl$_3$): (mixture of diastereomers): 170.8, 170.3, 166.9, 142.0, 130.6, 129.6, 128.3, 128.1, 125.6, 118.6 and 118.3, 98.0, 69.6, 36.0, 34.2, 32.8, 32.2, 29.1, 28.4, 24.7, 20.7.

m/z Calculated for C$_{22}$H$_{32}$O$_5$N (M+NH$_4$)+: 390.2280, obtained (CI+): 390.2281.

EXAMPLE 42

1-(4-Bromophenyl)pent-1-yne

A solution of 4-bromo-iodobenzene (4.23 g, 14.9 mmol), palladium (II) acetate (5 mg), triphenylphosphine (5 mg) in triethylamine (40 ml) was deareated with argon for 5 minutes. After 1-pentyne (1.77 ml, 18 mmol) was added, the solution was rapidly heated to reflux under argon and conditions maintained for 16 hours. On cooling, the mixture was poured into excess ice cold dilute hydrochloric acid and extracted with ethyl ether. Evaporation of the dried (magnesium sulphate) extracts gave an oil, which was flash chromatographed on silica using 5% ethyl ether/hexane. The title acetylene was obtained as a light brown oil (3.27 g, 99%).

$^1$H NMR (CDCl$_3$): 1.07 (t, 3H, J=7.4 Hz), 1.63 (sextet, 2H, J=8.3 Hz), 2.39 (t, 2H, J=7.1 Hz), 7.29 (d, 2H, J=7.8 Hz) and 7.42 (d, 2H, J=7.8 Hz).

MS m/e (% abundance) 224/222 (M+, 65, 67), 195 (60), 193 (61), 143 (48), 128 (100) and 114 (38).

4-[1-Acetoxy-1-[4-(pent-1-ynl)phenyl]methyl]-2-trimethylsilylfuran tert-Butyl lithium (a 1.7M solution in pentane; 5.27 ml, 8.9 mmol) was added dropwise to a solution of 1-(4-bromophenyl)pent-1-yne (1 g, 4.48 mmol) in tetrahydrofuran (15 ml) at −78° under argon. After 25 minutes, a solution of 5-trimethylsilyl-3-furaldehyde (753 mg, 4.48 mmol) in tetrahydrofuran (2 ml) was added, followed by acetic anhydride (1.26 ml, 1.35 mmol) after 1 hour. The mixture was allowed to warm to room temperature gradually over 4 hours and quenched with water. Extraction (ethyl ether) and evaporation of the dried (magnesium sulphate) extract gave an oil, which was flash chromatographed using 5% ethyl ether/hexane. Fractions with R$_f$ of about 0.22 on evaporation afforded the title acetate as a light yellow oil.

$^1$H NMR (CDCl$_3$): 0.15 (s, 9H), 0.97 (t, 3H, J=7.3 Hz), 1.56 (sextet, 2H, J=8.3 Hz), 2.04 (s, 3H), 2.31 (t, 2H, J=7.0 Hz), 6.41 (s, 1H), 6.71 (s, 1H), 7.22 (d, 2H, J=8.3 Hz), 7.31 (d, 2H, J=8.3 Hz) and 7.34 (s, 1H).

MS m/e (% abundance) 354 (M+, 62), 312 (45), 295 (47), 222 (15), 169 (24), 144 (11), 117 (12), 83 (23) and 73 (100).

4-[1-Acetoxy-1-[4-(pent-1-ynl)phenyl]methyl]-5-hydroxy-2(5H)-furanone

A mixture of 4-[1-acetoxy-1-[4-(pent-1-ynl)phenyl]methyl]-2-trimethylsilylfuran (271.5 mg) and Rose Bengal (5 mg) in tetrahydrofuran (7 ml) was exposed to singlet oxygen at −78° for 2 hours. The residue, after solvent removal, was purified by preparative TLC (20×20 cm, 1000μ, developed with 60% ethyl ether/hexane). The title furanone was obtained as a yellow oil.

$^1$H NMR (CDCl$_3$): 1.08 (t, 3H, J=7.4 Hz), 1.66 (sextet, 2H, J=6.8 Hz), 2.17 (s, 3H), 2.19 (s, 3H), 2.42 (t, 2H, J=6.8 Hz), 4.45 (br, 1H), 4.75 (br, 1H), 5.70 (d, 1H, J=8.6 Hz), 5.85 (s, 1H), 6.19 (s, 1H), 6.28 (d, 1H, J=8.6 Hz), 6.55 (brs, 1H), 7.32 (d, 1H, J=8.2 Hz) and 7.45 (d, 2H, J=8.3 Hz).

$^{13}$C NMR (mixture of diasteriomers) (CDCl$_3$): 13.4, 20.7, 20.8, 21.1, 21.3, 22.0, 25.5, 70.4, 71.5, 79.8, 80.0, 91.6, 91.9, 97.5, 97.9, 117.3, 120.9, 125.11, 125.5, 127.3, 127.6, 131.9, 132.2, 134.0, 134.7, 165.7, 165.9, 169.9, 170.2 and 170.4.

MS m/e: exact mass calculated for C$_{18}$H$_{18}$O$_5$ (M+) 314.1154, found 314.1169.

EXAMPLE 43

4-[1-Acetoxy-1-(4-pentylphenyl)methyl]-2-trimethylsilylfuran and
4-[1-Acetoxy-1-(4-pentylphenyl)methyl]-5-hydroxy-2(5H)-furanone A solution of 4-[1-acetoxy-1-[4-(pent-1-ynl)phenyl]methyl]-2-trimethylsilylfuran (187.5 mg, 0.53 mmol) in ethyl ether (10 ml) was hydrogenated over Lindlar catalyst (10 mg) for 2½ hours at room temperature. The mixture was filtered through celite and on evaporation gave the title acetate, which was used in the next step.

$^1$H NMR (CDCl$_3$): 0.26 (s, 9H), 0.92 (t, 3H, J=6.7 Hz), 1.35 (m, 4H), 1.65 (p, 2H, J=7.5 Hz), 2.14 (s, 3H), 2.62 (t, 2H, J=8.0 Hz), 6.56 (s, 1H), 6.82 (s, 1H), 7.19 (d, 2H, J=8.0 Hz), 7.32 (d, 2H, J=8.0 Hz) and 7.46 (s, 1H).

MS m/e (% abundance) 358 (M+, 40), 343 (8), 316 (40), 299 (38), 245 (15), 169 (20), 117 (15), 75 (31) and 73 (100).

A mixture of 4-[1-acetoxy-1-(4-pentylphenyl)methyl]-2-trimethylsilylfuran (from above) and Rose Bengal (5 mg) in tetrahydrofuran (7 ml) was exposed to singlet oxygen at −78° for 2 hours. The residue, after solvent removal, was purified by preparative TLC (20×20 cm, 1000μ silica plate; developed with 60% ethyl ether/hexane). The title furanone was obtained as a yellow oil $^1$H NMR (mixture of diasteriomers) (CDCl$_3$): 0.93 (t, 3H, J=6.5 Hz), 1.35 (m, 4H), 1.65 (m, 2H), 2.17 (s, 3H), 2.20 (s, 3H), 2.65 (t, 2H, J=8.2 Hz), 4.39 (d, 1H, J=9.2 Hz), 5.74 (d, 1H, J=9.2 Hz), 5.90 (s, 1H), 6.19 (brs, 1H), 6.26 (d, 1H), 6.54 (brs, 1H) and 6.57 (s, 1H).

$^{13}$C NMR (mixture of diasteriomers) (CDCl$_3$): 13.9, 20.7, 20.9, 22.4, 30.9, 31.4, 35.6, 70.7, 71.8, 76.6, 97.6, 98.0, 117.0, 120.8, 127.4, 127.7, 128.0, 128.9, 129.2, 132.1, 144.6, 166.5, 170.1, 170.2 and 170.5.

MS m/e: exact mass calculated for C$_{16}$H$_{18}$O$_3$ (M+-HOAc) 258.1256, found 258.1246.

EXAMPLE 44

4-(1-Acetoxyundeca-2,6-diynl)-2-trimethylsilylfuran n-Butyl lithium (a 1.6M solution in hexane; 0.98 ml, 1.56 mmol) was added dropwise to a solution of 1,5-decadiyne (199.7 mg, 1.49 mmol) in tetrahydrofuran (5 ml) at 0° under argon. After 30 minutes, a solution of 5-trimethylsilyl-3-furaldehyde (250 mg, 1.49 mmol) in tetrahydrofuran (250 mg, 1.49 mmol) was added, followed by acetic anhydride (0.42 ml) after 1 hour. The mixture was stirred at room temperature for 4 hours and quenched with water. Extraction (ethyl ether) and evaporation of the dried (magnesium sulphate) extracts gave an oil, which was flash chromatographed on silica using 10% ethyl ether/petroleum ether. Fractions with R$_f$ of about 0.5 on evaporation afforded the title acetate as a light yellow oil.

$^1$H NMR (CDCl$_3$): 0.30 (s, 9H), 0.94 (t, 3H, J=6.9 Hz), 1.45 (m, 4H), 2.14 (s, 3H), 2.15 (m, 2H), 2.45 (m, 4H), 6.45 (brs, 1H), 6.72 (s, 1H) and 7.85 (s, 1H).

MS m/e (% abundance) 344 (M+, 7), 301 (3), 285 (10), 242 (4), 207 (4), 169 (16), 75 (23) and 73 (100).

4-(1-Acetoxyundeca-2,6-diynl)-5-hydroxy-2(5H)-furanone

A mixture of 4-(1-acetoxyundeca-2,6-diynl)-2-trimethylsilylfuran (240 mg, 0.70 mmol) and Rose Bengal (5 mg) in tetrahydrofuran (7 ml) was exposed to singlet oxygen at −78° for 2 hours. The residue, after solvent removal, was purified by preparative TLC (20×20 cm, 1000μ silica plate; developed with 60% ethyl ether/hexane). The title furanone was obtained as a light yellow oil.

$^1$H NMR (CDCl$_3$): 0.92 (t, 3H, J=7.2 Hz), 1.40 (m, 4H), 2.17–2.19 (2s+brs, 5H), 2.43 (brm, 4H), 4.15 (d, 1H), 4.25 (d, 1H), 5.32 (brs, 1H), 6.10–6.25 (brs+d, 2H) and 6.40 (brs, 1H).

$^{13}$C NMR (CDCl$_3$): 13.5, 18.2, 18.4, 19.2, 20.6, 21.8, 30.8, 58.6, 59.5, 73.3, 73.9, 81.8, 88.0, 88.3, 97.2, 97.3, 97.6, 118.7, 122.1, 162.6, 162.9, 169.6, 169.6 and 170.0.

MS m/e: exact mass calculated for C$_{17}$H$_{20}$O$_5$ (M+) 304.1311, found 304.1316.

EXAMPLE 45

5-(2-Pyridyl)-4-pentyn-1-ol

A mixture of 2-bromopyridine (5 g, 31.6 mmol), palladium (II) acetate (5 mg), copper (I) iodide (5 mg), triphenylphosphine (5 mg) in triethylamine (40 ml) was deaerated with argon for 5 minutes. After 4-pentyn-1-ol (3.49 ml, 37.9 mmol) was added, the solution was rapidly heated to reflux under argon and conditions maintained for 22 hours. On cooling, the mixture was poured into 2M sodium hydroxide (ca. 30 ml) and extracted thoroughly with ethyl acetate. Evaporation of the dried (magnesium sulphate) extracts gave an oil, which was flash chromatographed on silica using 60% ethyl acetate/chloroform. Fractions with R$_f$ of about 0.12 on evaporation gave the title alcohol as a pale brown oil.

$^1$H NMR (CDCl$_3$): 1.91 (p, 2H, J=6.4 Hz), 2.20 (br, 1H), 2.60 (t, 2H, J=7.0 Hz), 3.85 (t, 2H, J=6.1 Hz), 7.18 (m, 1H), 7.38 (dd, 1H, J=7.8 Hz, 1.2 Hz), 7.64 (dt, 1H, J=7.7 Hz, 1.9 Hz) and 8.55 (d, 1H, J=4.8 Hz).

$^{13}$C NMR (CDCl$_3$): 15.7, 30.9, 60.6, 80.1, 90.7, 122.2, 126.7, 136.1, 143.3 and 149.2.

MS m/e (% abundance) 161 (M+, 25), 142 (11), 131 (100), 130 (99), 117 (44), 104 (17), 89 (18) and 78 (21).

5-(2-Pyridyl)-1-pentanol

A solution of 5-(2-pyridyl)-4-pentyn-1-ol (1 g, 6.2 mmol) in diethyl ether (15 ml) was hydrogenated over 10% palladium on carbon at room temperature for 16 h. The mixture was filtered through celite and the filtrate on evaporation gave an oil, which was flash chromatographed on silica using 80% ethyl acetate/chloroform. Fractions with R$_f$ of about 0.06 on evaporation gave the title alcohol as a yellow oil.

$^1$H NMR (CDCl$_3$): 1.49 (p, 2H, J=8.8 Hz), 1.66 (p, 2H, J=7.3 Hz), 1.82 (p, 2H, J=7.5 Hz), 2.86 (t, 2H, J=7.8 Hz), 2.95 (br, 1H), 3.71 (t, 2H, J=6.3 Hz), 7.15 (m, 2H), 7.65 (dt, 1H, J=9.2 Hz, 1.9 Hz) and 8.55 (d, 1H, J=4.9 Hz).

$^{13}$C NMR (CDCl$_3$): 25.1, 29.2, 32.1, 37.6, 61.4, 120.5, 122.4, 136.1, 148.3 and 161.6.

MS m/e (% abundance) 166 (M+, 18), 120 (17), 106 (22) and 93 (100).

2-(5-Bromopentyl)pyridine

A mixture of 5-(2-pyridyl)-1-pentanol (680 mg, 4.12 mmol) and 48% hydrobromic acid (10 ml) was warmed at ca. 90° for 22 h. On cooling, the mixture was neutralized with sodium bicarbonate. Extraction (ethyl acetate) and evaporation of the dried (magnesium sulphate) extracts gave an oil, which was flash chromatographed on silica using 40% ethyl acetate/hexane. Fractions with R$_f$ of about 0.24 on evaporation gave the title bromide as a yellow oil.

$^1$H NMR (CDCl$_3$): 1.54 (p, 2H, J=7.3 Hz), 1.80 (p, 2H, J=7.3 Hz), 1.94 (p, 2H, J=7.3 Hz), 2.83 (t, 2H, J=7.7 Hz), 3.44 (t, 2H, J=6.9 Hz), 7.15 (m, 2H), 7.63 (t, 1H, J=7.7 Hz) and 8.55 (d, 1H, J=4.4 Hz).

MS m/e (% abundance) 148 (M+-br, 9), 120 (16), 106 (10) and 93 (100).

4-[1-Acetoxy-6-(2-pyridyl)hexyl]-2-trimethylsilylfuran tert-Butyl lithium (a 1.7M solution in pentane; 2.4 ml, 4.14 mmol) was added dropwise to a solution of 2-(5-bromopentyl)pyridine (472.3 mg, 2.07 mmol) in tetrahydrofuran (7 ml) at −78° under argon. After 1 hour, a solution of 5-trimethylsilyl-3-furaldehyde (348 mg, 2.07 mmol) in tetrahydrofuran (1 ml) was added, followed by acetic anhydride (0.59 ml, 6.21 mmol) after 2 hours. The mixture was allowed to warm to room temperature and quenched with water (after 22 hours). Extraction (ethyl ether) and evaporation of the dried (magnesium sulphate) extracts gave an oil, which was flash chromatographed on silica using 40% ethyl acetate/hexane. Fractions with $R_f$ of about 0.25 on evaporation gave the title silyfuran as a light brown oil.

$^1$H NMR (mixtures of diasteriomers) (CDCl$_3$): 0.28 (s, 9H), 1.35 (brm, 4H), 1.75 (brm, 4H), 2.07 (s, 3H), 2.13 (s, 3H), 2.80 (brt, 2H), 5.79 (t, 1H, J=7.0 Hz), 6.61 (s, 1H), 7.15 (brm, 2H), 7.65 (s+m, 2H) and 8.57 (brd, 1H).

MX m/e (% abundance) 359(M+, 2), 344(7), 317(14), 316(38), 300(11), 299(15), 117(11), 107(17), 106(46), 93(100) and 73(48).

4-[1-Acetoxy-6-(2-pyridyl)hexyl]-5-hydroxy-2(5H)-furanone

A mixture of 4-[1-acetoxy-6-(2-pyridyl)hexyl]-2-trimethylsilylfuran (115 mg, 0.32 mmol) and Rose Bengal (5 mg) in tetrahydrofuran (6 ml) was exposed to singlet oxygen at −78° for 2 h. The residue, after solvent removal, was purified by preparative TLC (20×20 cm, 1000µ silica plate; developed with 80% ethyl acetate/hexane). The title furanone was obtained as a pale yellow oil.

$^1$H NMR (mixture of diasteriomers) (CDCl$_3$): 1.40 (brm, 4H), 1.70 (m, 2H), 1.85 (m, 2H), 2.07 (s, 3H), 2.12 (s, 3H), 2.81 (t, 2H, J=7.3 Hz), 5.60 (br, 1H), 5.98 (s, 1H), 6.21 (br, 1H), 7.20 (m, 2H), 7.69 (t, 1H, J=7.6 Hz) and 8.48 (d, 1H, J=4.8 Hz).

$^{13}$C NMR (CDCl$_3$): 20.8, 24.6, 28.7, 29.7, 32.7, 37.4, 69.5, 98.4, 118.4, 121.6, 123.4, 137.6, 148.1, 161.5, 167.1 and 170.3.

MS exact mass calculated for $C_{17}H_{20}NO_5$ (M−H)+318.1341, found 318.1339.

EXAMPLE 46

5-(2-Naphthyl)-pent-4-yn-1-ol

A mixture of 2-bromonaphthalene (5 g, 24.1 mmol), 4-pentyn-1-ol (2.67 ml, 28.9 mmol), bis(triphenylphosphine) palladium (II) chloride (30 mg) and copper (I) iodide (10 mg) in triethylamine (40 ml) was refluxed under argon for 15 hours. After cooling, the mixture was acidified with ice-cold dilute hydrochloric acid and extracted with ethyl ether. Evaporation of the dried (magnesium sulfate) extracts gave an oil, which was purified by flash chromatography on silica using 60% ethyl ether/hexane. Fractions with $R_f$ of about 0.32 on evaporation gave a solid, which was recrystallized from dichloromethane/hexane to give the title alkynol as an off-white solid, mp 37°-8°.

$^1$H NMR (CDCl$_3$): 1.60 (br, 1H), 1.94 (p, 2H, J=6.4 Hz), 2.63 (t, 2H, J=7.0 Hz), 3.89 (brm, 2H), 7.50-7.80 (m, 6H) and 7.94 (brs, 1H).

$^{13}$C NMR (CDCl$_3$): 15.8, 31.2, 61.2, 81.3, 89.8, 120.9, 126.1, 126.2, 127.4, 127.5, 127.7, 128.4, 130.9, 132.2 and 132.8.

MS m/e (% abundance) 210 (M+, 96), 191 (34), 178 (36), 165 (100), 154 (54), 141 (27), 128 (23) and 115 (9).

5-(2-Napthyl)pentan-1-ol

A mixture of 5-(2-napthyl)-4-pentyn-1-ol (520 mg, 247 mmol) and 10% palladium on activated carbon in ethyl ether (50 ml) was stirred at room temperature under a hydrogen atmosphere for 2 days. Solvent removal, after filtration through celite, gave the titled compound as a light yellow oil.

$^1$H NMR (CDCl$_3$): 7.78 (m, 3H), 7.6 (s, 1H), 7.4 (m, 3H), 3.64 (t, 2H, J=6.5 Hz), 2.79 (t, 2H, J=7.4 Hz), 1.7 (m, 2H), 1.6 (m, 2H) and 1.4 (m, 2H).

1-Bromo-5-(2-napthyl)-pentane

Bromine (a 2M solution in dichloromethane; 955 mg, 5.97 mmol) was added to a solution of 1,2-bis (diphenyl)phosphinoethane (1.16 g, 2.99 mmol) in dichloromethane (15 ml) at 0°. A solution of 5-(2-napthyl)pentan-1-ol (513 mg, 2.39 mmol) in dichloromethane (5 ml) was added to the 0° solution. The solution was warmed to room temperature and stirred for 1.5 hours. The solution was diluted with ethyl ether/pentane (1:3), filtered through a thin pad of celite and the solvent evaporated. The resulting oil was purified by flash chromatography (hexane) giving the title compound as a colorless oil.

$^1$H NMR (CDCl$_3$): 7.75 (m, 3H), 7.6 (s, 1H), 7.4 (m, 3H), 3.4 (t, 2H, J=6.8 Hz), 2.78 (t, 2H, J=7.7 Hz), 1.9 (m, 2H), 1.7 (m, 2H) and 1.5 (m, 2H).

3-[1-Hydroxy-6-(2-napthyl)-hexyl]-4-trimethylsilylfuran t-BuLi (a 1.7M solution in hexane; 2.35 ml, 4.00 mmol) was added to a −78° solution of 1-bromo-5-(2-napthyl)pentane (555 mg, 2.00 mmol) in terahydrofuran (4 ml). After stirring for 30 minutes at −78°, a solution of 5-trimethylsilyl-3-furaldehyde (336 mg. 2.0 mmol) in tetrahydrofuran (0.5 ml) was added, and the solution stirred overnight at room temperature. The reaction was quenched with water. Extraction (ethyl ether) and evaporation of the dried (magnesium sulfate) extracts gave an oil, which was flash chromatographed on silica gel (30% ethyl ether/hexane). The title compound was obtained as a light yellow oil.

$^1$H NMR (CDCl$_3$): 7.8 (m, 3H), 7.59 (s, 1H), 7.55 (s, 1H), 7.4 (m, 3H), 6.61 (s, 1H), 4.62 (t, 1H, J=4.0 Hz), 2.76 (t, 2H, J=7.6 Hz), 1.7 (m, 4H), 1.4(m,4H) and 0.26 (s, 9H).

$^{13}$C NMR (CDCl$_3$) 161.2, 143.0, 140.1, 133.5, 131.8, 129.0, 127.6, 127.5, 127.3, 126.2, 125.7, 124.9, 118.2, 66.7, 37.7, 35.9, 31.1, 28.9, 25.5, −1.7.

3-[1-Acetoxy-5-(2-napthyl)hexyl]-5-trimethylsilylfuran

A mixture of 3-[1-hydroxy-5-(2-napthyl)hexyl]-5-trimethylsilylfuran (120 mg, 0.3 mmol) and acetic anhydride (66 mg, 651 mmol) in pyridine (1.3 ml) was stirred at room temperature overnight. After removal of the solvent, the residue was purified by preparative TLC (20×20 cm, 500µ silica gel plate; developed with 30% ethyl ether/hexane) yielding the title compound as a yellow oil.

$^1$H NMR (CDCl$_3$): 7.8 (m, 3H), 7.59 (d, 2H, J=3.2 Hz), 7.43 (m, 2H), 7.3 (m, 1H), 6.57 (s, 1H), 5.76 (t, 1H, J=6.6 Hz), 2.75 (t, 2H, J=7.7 Hz), 2.05 (s, 3H), 1.8 (m, 4H), 1.45 (m, 4H) and 0.24 (s, 9H).

$^{13}$C NMR (CDCl$_3$): 170.4, 161.1, 144.4, 140.0, 133.5, 131.9, 127.7, 127.5, 127.3, 126.2, 125.8, 124.9, 124.8, 118.6, 68.4, 35.9, 34.6, 31.1, 28.8, 25.4, 21.2, −1.7.

MS exact mass calculated for C$_{25}$H$_{32}$O$_3$Si (M+) 408.2120, found 408.2121.

4-[1-Acetoxy-6-(2-naphthyl)hexyl]-5-hydroxy-2(5H)-furanone

Oxidizing the above prepared trimethylsilylfuran by the procedure of Example 41 gave the title compound.

$^1$HNMR (CDCl$_3$) (mixture of diastereomers) 7.78 (m,2H), 7.59(brs, 1H), 7.45(m, 2H), 7.3(m, 1H), 6.17(brs, 1H), 5.97(brs, 2H), 5.47(t, 1H), 5.4j0((t, 1H),5.05(brs, 1H), 4.65(brs, 1H), 2.a76(t, 2H, J=7.8 Hz), 2.1(s, 3H), 2.08(s,3H), 1.7(m, 4H) and 1.35(m,4H).

$^{13}$CNMR (CDCl$_3$) 170.9, 166.9, 139.8, 139.7, 133.5, 131.8, 127.7, 127.5, 127.3, 127.2, 126.2, 125.8, 125.1, 125.0, 118.9, 118.1, 98.1, 97.6, 76.6, 69.7, 69.1, 35.8, 32.7, 30.8, 28.6, 24.7 and 20.7.

MS exact mass calculated for C$_{22}$H$_{24}$O$_5$ (M+) 368.1623, found 368.1621.

EXAMPLE 47

2-(2-Naphthyl)ethanol is reacted with methanesulfonyl chloride in the presence of triethylamine to give the methanesulfonyloxyethyl compound. Reacting this intermediate with 3-propyn-1-ol, then brominating gives 2-(5-bromopent-3-ynyl)naphthalene. Reacting this intermediate with t-butyl lithium and 5-trimethylsilyl-3-furaldehyde and then oxidizing by the procedure of Example 90 gives 4-[1-acetoxy-6-(2-naphthyl)hex-3-ynyl]-5-hydroxy-2(5H)-furanone.

EXAMPLE 48

Using the procedure of Example 46, except that the hydrogenation step is omitted, the product is 4-[1-acetoxy-6-(2-naphthyl)hex-5-ynyl]-5-hydroxy-2(5H)-furanone.

EXAMPLE 49

4-[1-Acetoxy-6-(2-pyridyl)hexyl]-5-hydroxy-2(5H)-furanone is reacted with methyl iodide to give the N-methyl ammonium iodide salt.

EXAMPLE 50

Using 2-chloroquinoline in place of 2-bromopyridine in the procedure of Example 41, the product is 4-[1-acetoxy-6-(2-quinolyl)hexyl]-5-hydroxy-2(5H)-furanone.

EXAMPLE 51

Beginning with 2-bromopyridine and carrying out the procedure of Example 41 except omitting the second step (hydrogenating), the product is 4-[1-acetoxy-6-(2-pyridyl)hex-5-ynyl]-5-hydroxy-2(5H)-furanone.

EXAMPLE 52

4-Bromobenzaldehyde is converted to 4-(5-hydroxypent-1-ylyl)benzaldehyde by the procedure of Example 90. This intermediate is brominated, then oxidized (Jones oxidation) to give the 4-substituted benzoic acid. Treating with t-butyl lithium and 5-trimethylsilyl-3-furaldehyde and then with acetic anhydride, hydrogenating the triple bond, then oxidizing gives 4-[1-acetoxy-6-(4-carboxyphenyl)hexyl]-5-hydroxy-2(5H)-furanone.

EXAMPLE 53

1-(2-Bromophenyl)tridec-1-yne

A mixture of 1-bromo-2-iodobenzene (5 g, 17.7 mmol), 1-tridecyne (4.9 ml, 21.2 mmol), triphenylphosphine (5 mg), palladium (II) chloride (5 mg) in triethylamine (45 ml) was refluxed under argon for 15 h. After cooling, the mixture was poured into ice-cold dilute hydrochloric acid and extracted thoroughly with ethyl ether. Evaporation of the dried (magnesium sulfate) extracts gave an oil, which was purified by a silica column using hexane. Fractions with R$_f$ of about 0.36 on evaporation gave the title alkyne as a brown oil.

$^1$H NMR (CDCl$_3$): 0.89 (t, 3H, J-6.9 Hz), 1.28 (brs, 14H), 1.50 (m, 2H), 1.65 (m, 2H), 2.48 (t, 2H, J=7.0 Hz), 7.12 (dt, 1H, J=7.7 Hz, 1.7 Hz), 7.24 (dt, 1H, J=8.1 Hz, 1.2 Hz), 7.44 (dd, 1H, J=7.7 Hz, 1.8 Hz) and 7.56 (dd, 1H, J=8.1 Hz, 1.2 Hz).

MS m/e (% abundance) 335/337 [(M+H+), 21/19], 334/336 (M+, 26/29), 235/237 (39/42), 221/223 (45/48), 195/197 (63/67), 169/171 (49/51), 129 (100), 116 (78), 109 (32) and 95 (96).

3-[1-Acetoxy-1-(2-(1-tridecynyl)phenyl)methyl]-5-trimethylsilylfuran tert-Butyl lithium (a 1.7M solution in pentane; 2.44 ml, 4.1 mmol) was added dropwise to a solution of 1-(2-bromophenyl)tridec-1-yne (692 mg, 2.07 mmol) in tetrahydrofuran (5 ml) at −78° under argon. After 30 min, a solution of 5-trimethylsilyl-3-furaldehyde (348 mg, 2.07 mmol) in tetrahydrofuran (0.5 ml), followed by acetic anhydride (0.6 ml, 6.2 mmol) after 2 hours, was added. Stirring was continued at −78° for 4 hours and at room temperature for 2 hours. The mixture was poured into water and extracted with ethyl ether. Evaporation of the dried (magnesium sulfate) extracts gave an oil, which was purified by flash chromatography on silica using 10% ethyl ether/hexane. Fractions with R$_f$ of about 0.43 on evaporation gave the title acetate as a pale yellow oil.

$^1$H NMR (CDCl$_3$): 0.26 (s, 9H), 0.92 (t, 3H, J-6.7 Hz), 1.29 (brs, 14H), 1.45 (m, 2H), 1.60 (m, 2H), 2.16 (s, 3H), 2.45 (t, 2H, J=7.0 Hz), 6.59 (s, 1H), 7.29 (s, 1H), 7.25-7.40 (2 t, 2H), 7.42 (d, 1H, J=7.0 Hz), 7.48 (s, 1H) and 7.51 (d, 1H, J=7.5 Hz).

MS m/e (% abundance) 466 (M+, 5), 407 (100), 335 (9), 267 (7), 253 (14), 117 (26), 75 (12), 73 (57), 61 (13) and 57 (10).

4-[1-Acetoxy-1-(2-(1-tridecynyl)phenyl)methyl]-5-hydroxy-2(5H)-furanone

A mixture of 3-[1-acetoxy-1-(2-tridecynylphenyl)methyl]-5-trimethylsilylfuran (170 mg, 0.36 mmol) and Rose Bengal (5 mg) in tetrahydrofuran (7 ml) was exposed to singlet oxygen at −78° for 2.5 hours. The residue, after solvent removal, was purified by preparative TLC (20×20 cm, 1000 μ; developed with 60% ethyl ethyl/hexane). The title furanone was obtained as a deep yellow oil.

$^1$H NMR (mixture of diasteriomers) (CDCl$_3$): 0.89 (t, 3H, J=6.4 Hz), 1.25 (brs, 16H), 1.40 (brm, 4H), 1.60 (m, 2H), 2.17 (s, 3H), 2.44 (t, 2H, J=7.2 Hz), 5.30 (br, 1H), 5.90 (brs, 1H), 6.10 (brs, 1H), 6.20 (br, 1H), 7.0 (brs, 1H) and 7.25-7.50 (m, 4H).

$^{13}$C NMR (mixture of diasteriomers) (CDCl$_3$): 14.1, 19.5, 20.8, 22.6, 28.5, 28.8, 29.0, 29.1, 29.3, 29.5, 29.6, 30.0, 31.8, 69.7, 69.8, 76.6, 76.9, 97.6, 97.8, 98.0, 118.4, 123.5, 126.6, 127.3, 128.0, 128.1, 128.3, 128.5, 128.9, 129.0, 129.1, 132.7, 136.2, 166.3, 170.2 and 170.3.

MS: exact mass calculated for $C_{26}H_{38}O_5N$ $(M+NH_4)^+$ 444.2750, found 444.2731.

EXAMPLE 54

5-(2-Pyridyl)-4-pentyn-1-ol, prepared as in Example 41, is reduced by hydrogenating using rhodium on carbon as catalyst to give 5-(2-piperidyl)-pentan-1-ol. Treating that intermediate with methyl iodide and sodium hydride gives the N-methyl compound. Brominating, reacting the bromo compound with t-butyl lithium and 5-trimethylsilyl-3-furaldehyde, then oxidizing by the procedure of Example 41 gives 4-[1-acetoxy-6-(N-methylpiperidyl)hexyl]-5-hydroxy-2(5H)-furanone.

EXAMPLE 55

By hydrogenating 6,6-diphenyl-4-hexyn-1-ol (prepared from diphenylmethyl bromide and dilituium salt of 4-pentyn-1-ol) then brominating the reduced product, treating that with t-butyl lithium and 5-trimethylsilyl-3-furaldehyde gives a product which when treated with acetic anhydride and oxidized gives 4-(1-acetoxy-7,7-diphenylheptyl)-5-hydroxy-2(5H)-furanone.

EXAMPLE 56

Using 1,1,1-triphenyl-2-hexyn-1-ol (prepared from triphenylcarbenium tetrafluoroborate and di-lithium salt of 4-pentyn-1-ol) in the procedure of Example 55 gives 4-(1-acetoxy-7,7,7-triphenylheptyl)-5-hydroxy-2(5H)-furanone.

EXAMPLE 57

4-(1-Hydroxytridecyl)-2-trimethylsilylfuran, prepared as in Example 38, is reacted with t-butyl lithium and t-butyldimethylsilyl chloride to give the 1-t-butyldimethylsilyloxy compound which is oxidized, then-treated with acetic anhydride and pyridine, then with acetic acid to give 4-(1-hydroxytridecyl)-5-acetoxy-2(5H)-furanone.

EXAMPLE 58

5-Trimethylsilyl-3-furaldehyde is treated with t-butyl lithium and 1-bromododecanoic acid to give 13-hydroxy-13-(5-trimethylsilyl-3-furyl)tridecanoic acid. The hydroxy carboxylic acid group is converted to the lactone by treating with 1,3-dicyclohexylcarbodiimide and 4-dimethylaminopyridine and the resulting compound is oxidized to give the lactone of 13-hydroxy-13-(2-hydroxy-5-oxo-3-furyl)tridecanoic acid.

EXAMPLE 59

4-(1-Acetoxy-11-phenylundecyl)-5-hydroxy-2(5H)-furanone

Using the procedures of Example 45, 10-phenyldecan-1-ol was brominated, then reacted with t-butyl lithium and 5-trimethylsilyl-3-furaldehyde, then with acetic anhydride and oxidized to give the title compound.

$^1$HNMR (CDCl$_3$): 7.2(m, 5H), 6.02(brs, 1H), 5.96(s, 1H), 5.55(brs, 1H), 5.50(t, 1H, J=6.2 Hz), 2.59(t, 2H, J=7.5 Hz), 2.12(s, 3H), 1.80(m, 2H), 1.55(m, 2H) and 1.25(m, 16H).

$^{13}$CNMR (CDCl$_3$): 171.0, 170.2, 167.1, 142.8, 128.3, 128.1, 125.5, 118.2, 98.0, 69.7, 69.4, 35.9, 32.9, 31.4, 29.4, 24.9 and 20.8.

EXAMPLE 60

4-[1-Acetoxy-6-(4-phenyl)phenylhexyl]-5-hydroxy-2(5H)-furanone

Using the procedures of Example 45, 5-(4-phenyl)phenylpentan-1-ol was brominated, reacted with magnesium and 5-trimethylsily-3-furaldehyde, then with acetic anhydride and then oxidized to the obtain the title compound.

$^1$HNMR (CDCL$_3$): 7.4(m, 9H), 6.05 (brs, 1H), 5.97 (s, 1H), 5.45 (t, 1H, J~6.3 Hz), 2.64 (t, 2H, J~7.4 Hz), 2.18 (s, 3H), 2.17 (s, 3H), 1.8 (m, 2H), 1.65 (m, 2H) and 1.4 (m, 6H).

$^{13}$CNMR (CDCl$_3$): 171.2, 169.9, 167.0, 141.4, 140.9, 138.7, 128.8, 127.0, 126.9, 119.1, 118.4, 97.9, 69.7, 69.5, 35.3, 32.9, 31.6, 31.0, 28.7, 25.1 and 20.8.

EXAMPLE 61

4-(1-Acetoxy-6-(2,4,5-trifluorophenyl)hexyl)-5-hydroxy-2(5H)-furanone

Using the procedure of Example 45, 2,4,5-trifluorophenylpentan-1-ol is brominated, reacted with magnesium and 5-trimethylsilyl-3-furaldehyde, then with acetic anhydride, and oxidized to give the title compound.

EXAMPLE 62

By procedures described herein, the following compounds of this invention are prepared:

4-[1-acetoxy-10-(2-(N-methyl)pyrrolyl)decyl]-5-hydroxy-2(5H)-furanone.

4-[1-acetoxy-6-(2-pentylphenyl)hexyl]-5-hydroxy-2(5H)-furanone.

4-(1-acetoxy-11,11-dimethyldecyl)-5-hydroxy-2(5H)-furanone.

4-(1-acetoxy-10-methoxydecyl)-5-hydroxy-2(5H)-furanone.

4-(1-acetoxy-7-pentoxyheptyl)-5-hydroxy-2(5H)-furanone.

4-(1-acetoxy-8-carboxyoctyl)-5-hydroxy-2(5H)-furanone and the ethyl ester thereof.

EXAMPLE 63

3-[1-Acetoxy-1-(2-(1-tridecynyl)phenyl)methyl]-5-trimethylsilylfuran, prepared as in Example 53, is hydrogenated using palladium on charcoal to give the 2-tridecylphenyl compound. Oxidizing by the procedure of Example 53 gives 4-[1-acetoxy-1-(2-tridecylphenyl)-methyl]-5-hydroxy-2(5H)-furanone.

EXAMPLE 64

1-Bromo-8-t-butyldimethylsiloxyoctane

A solution of 8-bromooctan-1-ol (2.15 g, 10.3 mmol), t-butyldimethylsilyl chloride (1.7 g, 11.3 mmol) and imidazole (1.7 g, 25.0 mmol) in dimethylformamide (4 ml) was stirred at room temperature under argon for 48 hours. The reaction was quenched by the addition of water and extracted with hexane. The organic layer was washed with 5% hydrochloric acid, 5% sodium bicarbonate, water, saturated sodium chloride solution, dried over magnesium sulfate, filtered and concentrated to give a colorless oil. Purification by flash chromatography (silica, 0 to 2% ethyl ether/hexane) gave the desired protected alcohol.

$^1$H NMR (CDCl$_3$): 3.58 (t, 2H, J=6.5 Hz), 3.38 (t, 2H, J=6.9 Hz), 1.25 to 1.55 (m, 12H), 0.88 (s, 9H), 0.03 (s, 6H).

8-(Thiophen-2-yl)octan-1-ol

To a stirred solution of 2-bromothiophene (0.341 g, 2.09 mmol) in tetrahydrofuran (30 ml) under argon at −78° was added t-butyl lithium (2.53 ml of a 1.7M solution) followed by 1,3-dimethyl-3,4,5,6-tetrahydro-2(1H)-pyrimidinone (0.268 g, 2.09 mmol). To this mixture was added 1-bromo-8-t-butyldimethylsiloxyoctane (0.615 g, 1.90 mmol) in tetrahydrofuran (10 ml). After gradual warming followed by stirring at room temperature for 18 hours, the mixture was concentrated, taken up in ethyl ether and washed consecutively with cold 10% hydrochloric acid, saturated sodium bicarbonate, water, saturated sodium chloride solution, dried over magnesium sulfate, filtered and concentrated to give a yellow oil. To this residue in tetrahydrofuran (20 ml) at 0° was added tetrabutylammonium fluoride (8.4 ml of a 1.0M solution). After stirring for 16 hours at room temperature, the mixture was concentrated, taken up in ethyl ether and washed with 10% hydrochloric acid, saturated sodium bicarbonate, water, saturated sodium chloride solution, dried over magnesium sulfate, filtered and concentrated to give a yellow oil. Further purification by flash chromatography (silica, 30% ethyl acetate/hexane) gave the desired alcohol.

IR (neat): 3340 (broad), 2930, 1460, 1440, 690 cm$^{-1}$.

$^1$H NMR (CDCl$_3$): 7.10 (d, 1H, J=5.1 Hz), 6.91 (dd, 1H, J=5.0, 3.5 Hz), 6.77 (d, 1H, J=3.4 Hz), 3.62 (t, 2H, J=6.6 Hz), 2.81 (t, 2H, J=7.6 Hz), 1.60 to 1.72 (m, 2H), 1.45 to 1.60 (m, 3H) and 1.25 to 1.45 (m, 8H).

$^{13}$C NMR (CDCl$_3$): 145.7, 126.6, 123.9, 122.7, 62.9, 32.7, 31.7, 29.8, 29.3, 29.0, 25.6.

m/z calculated for C$_{12}$H$_{20}$OS (M+): 212.1235; obtained (EI+): 212.1238.

8-(Thiophen-2-yl)octan-1-ol

To a stirred solution of 2-bromothiophene (0.341 g, 2.09 mmol) in tetrahydrofuran (30 ml) under argon at −78° was added t-butyl lithium (2.53 ml of a 1.7M solution) followed by 1,3-dimethyl-3,4,5,6-tetrahydro-2(1H)-pyrimidinone (0.268 g, 2.09 mmol). To this mixture was added 1-bromo-8-t-butyldimethylsiloxyoctane (0.615 g, 1.90 mmol in tetrahydrofuran (10 ml). After gradual warming followed by stirring at room temperature for 18 hours, the mixture was concentrated, taken up in ethyl ether and washed consecutively with cold 10% hydrochloric acid, saturated sodium bicarbonate, water, saturated sodium chloride solution, dried over magnesium sulfate, filtered and concentrated to give a yellow oil. To this residue in tetrahydrofuran (20 ml) at 0° was added tetrabutylammonium fluoride (8.4 ml of a 1.0M solution). After stirring for 16 hours at room temperature the mixture was concentrated, taken up in ethyl ether and washed with 10% hydrochloric acid, saturated sodium bicarbonate, water, saturated sodium chloride solution, dried over magnesium sulfate, filtered and concentrated to give a yellow oil. Further purification by flash chromatography (silica, 30% ethyl acetate/hexane) give the desired alcohol.

IR (neat): 3340 (broad), 2930, 1460, 1440, and 690 cm$^{-1}$.

$^1$H NMR (CDCl$_3$): 7.10 (d, 1H, J∼5.1 Hz); 6.91 (dd, 1H, J∼5.0, 3.5 Hz), 6.77 (d, 1H, J∼3.4 Hz) 3.62 (t, 2H, J∼6.6 Hz); 2.81 (t, 2H, J∼7.6 Hz); 1.60 to 1.72 (m, 2H); 1.45 to 1.60 (m, 3H) and 1.25 to 1.45 (m, 8H).

$^{13}$C NMR (CDCl$_3$): 145.7, 126.6, 123.9, 122.7, 62.9, 32.7, 31.7, 29.8, 29.3, 29.0, 25.6.

m/z Calculated for C$_{12}$H$_{20}$OS (M+): 212.1235, obtained (EI+): 212.1238.

1-Bromo-8-(thiophen-2-yl)octane

To a stirring mixture of 8-(thiophen-2-yl)-octan-1-ol (0.132 g, 0.622 mmol) and triethylamine (0.126 g, 1.245 mmol) in methylene chloride (5 ml) at 0° under argon was added methanesulfonyl chloride (0.107 g, 0.933 mmol). After stirring for 2 hours at 0° the reaction was quenched with water and the organic layer was washed with 10% hydrochloric acid, saturated sodium bicarbonate, water, saturated sodium chloride solution, dried over magnesium sulfate, filtered and concentrated to give a pale oil. To this oil in acetone (2 ml) was added lithium bromide (0.216 g, 2.49 mmol) and the mixture was refluxed for 15 hours. The acetone was evaporated and the residue was taken up in ethyl ether, washed with 10% hydrochloric acid, saturated sodium bicarbonate, water, saturated sodium chloride, dried over magnesium sulfate, filtered through silica and concentrated to give the title compound which was carried on without further purification.

IR (CHCl$_3$): 2920, 1455, 1435, 685 cm$^{-1}$.

$^1$H NMR (CDCL$_3$): 7.10 (dd, 1H, J=5.2, 1.3 Hz), 6.91 (dd, 1H, J=5.1, 3.3 Hz), 6.77 (d, 1H, J=3.6 Hz), 3.4 (t, 2H, J=6.9 Hz), 2.81 (t, 2H, J=7.6 Hz), 1.80 to 1.95 (m, 2H), 1.60 to 1.75 (m, 2H) and 1.25 to 1.50 (m, 8H).

$^{13}$C NMR (CDCl$_3$): 145.7, 126.6, 123.9, 122.7, 34.0, 32.8, 31.7, 29.9, 29.1, 29.0, 28.6, 28.1.

m/z Calculated for C$_{12}$H$_{19}$BrS (M+): 274.0390; obtained (EI+): 274.0398.

4-(1-Hydroxy-9-thiophen-2-ylnonyl)-2-trimethylsilylfuran

To a stirred solution of 8-(thiophene-2-yl)octyl magnesium bromide [0.62 mmol, prepared from 1-bromo-8-(thiophen-2-yl)octane; 0.170 g, 0.620 mmol and 1.24 mmol magnesium with a catalytic amount of 1,2 dibromoethane as initiator] in tetrahydrofuran (2 ml) at 0° under argon was added dropwise 5-trimethylsilyl-3-furaldehyde (0.104 g, 0.620 mmol) in tetrahydrofuran (3 ml). The solution was warmed to room temperature, stirred for one hour, quenched with saturated ammonium chloride solution and extracted into ethyl ether. The organic portion was washed with saturated sodium bicarbonate solution, water, saturated sodium chloride solution, dried over magnesium sulfate, filtered and concentrated to a yellow oil. Purification by flash chromatography (silica, 5 to 10% ethyl acetate/hexane) gave the desired alcohol.

IR (CHCl$_3$): 3600, 3000, 2920, 1220 cm$^{-1}$.

$^1$H NMR (CDCl$_3$): 7.56 (s, 1H), 7.10 (d, 1H, J=2.7 Hz), 6.91 (dd, 1H, J=3.5, 2.4 Hz), 6.77 (d, 1H, J=3.3 Hz), 6.62 (s, 1H), 4.64 (t, 1H, J=6.6 Hz), 2.81 (t, 2H, J=7.6 Hz), 1.58 to 1.83 (m, 5H), 1.20 to 1.50 (m, 10H), and 0.25 (s, 9H).

$^{13}$C NMR (CDCl$_3$): 161.4, 145.8, 143.1, 129.2, 126.6, 123.9, 122.7, 118.3, 67.0, 37.9, 37.9, 31.8, 29.9, 29.4, 29.3, 29.1, 25.7, −1.7.

c/z Calculated for C$_{20}$H$_{32}$O$_2$SSi(M+): 364.1892; obtained (CI+): 364.1885.

4(1-Acetoxy-9-thiophen-2-ylnonyl)-2-trimethylsilylfuran

A solution of 4-(1-hydroxy-9-thiophen-2-ylnonyl)-2-trimethylsilylfuran (0.034 g, 0.093 mmol), acetic anhydride (1 ml) and pyridine (0.25 ml) was stirred at room temperature until no starting material was visible by TLC. The reaction mixture was concentrated and the residue taken up in ethyl ether, washed with 10% hydrochloric acid, saturated sodium chloride, aqueous 5% cupric sulfate solution, water, saturated sodium chloride solution, dried over magnesium sulfate, filtered and concentrated to give a pale oil. Purificatioon by flash chromatography (silica, 100% hexane to 5% ethyl ether/hexane) gave the title compound.

IR (CHCl$_3$): 2920, 2840, 1720, 1370, 1250 cm$^{-1}$.

$^1$H NMR (CDCl$_3$): 7.59 (s, 1H), 7.10 (dd, 1H, J=5.1, 1.2 Hz), 6.91 (dd, 1H, J=5.1, 3.6 Hz), 6.77 (d, 1H, J=2.4 Hz), 6.58 (s, 1H), 5.76 (t, 1H, J=7.0 Hz), 2.81 (t, 2H, J=7.6 Hz), 2.05 (s, 3H), 1.60 to 1.92 (m, 4H), 1.20 to 1.50 (m, 10H) and 0.25 (s, 9H).

$^{13}$C NMR (CDCl$_3$): 170.5, 161.2, 145.7, 144.4, 126.6, 124.9, 123.4, 122.7, 118.6, 68.5, 34.7, 31.7, 29.9, 29.3, 29.2, 29.0, 25.5, 21.3, −1.7.

m/z Calculated for C$_{22}$H$_{34}$O$_3$ SSi (M+): 406.1998; obtained 406.1979.

4-(1-Acetoxy-9-thiophen-2-ylnonyl)-5-hydroxy-2(5H)-furanone

A stirred solution of 4-(1-acetoxy-9-thiophen-2-ylnonyl)-2-trimethylsilylfuran (0.024 g, 0.059 mmol) and Rose Bengal (2 mg) in acetone (4 ml) was flushed with oxygen and cooled to −78°. The solution was subsequently irradiated with a 150 watt flood lamp while under constant positive pressure of oxygen until starting material was no longer visible by TLC. The solution was warmed to room temperature and concentrated to a pink oil. Purification by flash chromatography (silica, 40% ethyl acetate/hexane) gave the desired hydroxybutenolide.

IR (CHCl$_3$): 3400 (broad), 2930, 1750 (broad) cm$^{-1}$.

$^1$H NMR (mixture of diastereomers) (CDCl$_3$): 7.10 (dd, 1H, J=5.1, 1.2 Hz), 6.91 (dd, 1H, J=5.1, 3.3 Hz), 6.77 (d, 1H, J=1.2 Hz), 5.95 to 6.10 (m, 2H), 5.35 to 5.45 (brt, 1H), 5.1 to 5.3 (brd, 1H), 2.82 (t, 2H, J=7.6 Hz), 2.13 (s, 3H), 1.75 to 1.95 (m, 2H), 1.63 to 1.75 (m, 2H) and 1.20 to 1.55 (m, 10H).

$^{13}$C NMR (mixture of diastereomers) (CDCl$_3$): 171.1, 170.0, 167.2, 145.7, 126.6, 123.9, 122.7, 118.6, 118.4, 98.0, 69.7, 69.6, 33.0, 31.7, 29.8, 29.14, 29.06, 29.0, 24.9, and 20.8.

m/z Calculated for C$_{19}$H$_{27}$O$_5$S (MH+): 367.1579; obtained (CI+): 367.1594.

EXAMPLE 65

4-(1-Hydroxy-9-t-butyldimethylsiloxynonyl)-2-trimethylsilylfuran

To a stirred solution of 8-t-butyldimethylsiloxyoctyl-magnesium bromide (5.63 mmol prepared from 1-bromo-8-t-butyldimethylsiloxyoctane 1.82 g, 5.63 mmol and 6.19 mmol magnesium; with a catalytic amount of 1,2-dibromoethane as initiator) in tetrahydrofuran (2 ml) at 0° under argon was added dropwise 5-trimethylsilyl-3-furaldehyde (0.866 g, 5.15 mmol) in tetrahydrofuran (10 ml). The solution was warmed to room temperature, stirred for one hour, quenched with cold 10% hydrochloric acid and extracted into ethyl ether. The organic portion was washed with saturated sodium bicarbonate, water saturated sodium chloride solution, dried over magnesium sulfate, filtered and concentrated to give a pale oil. Purification by flash chromatography (silica, 5 to 10% ethyl acetate/hexane) gave the desired alcohol.

IR (neat): 3350, 1250 cm$^{-1}$.

$^1$H NMR (CDCl$_3$): 7.59 (s, 1H), 6.65 (s, 1H), 4.67 (t, 1H, J=6.3 Hz), 3.62 (t, 2H, J=6.6 Hz), 1.20 to 1.90 (m, 15H), 0.92 (s, 9H), 0.28 (s, 9H), and 0.07 (s, 6H).

$^{13}$C NMR (CDCl$_3$): 161.3, 143.1, 129.1, 118.2, 66.9, 63.3, 37.9, 32.8, 29.5, 29.4, 29.3, 26.0, 25.7, 18.4, −1.7.

m/z Calculated for C$_{22}$H$_{44}$O$_3$Si$_2$ (M+): 412.2829; obtained (CI+): 412.2834.

4-(1-Acetoxy-9-t-butyldimethylsiloxynonyl)-2-trimethylsilylfuran

A solution of 4-(1-hydroxy-9-t-butyldimethylsiloxynonyl)-2-trimethylsilylfuran (0.892 g, 2.17 mmol), acetic anhydride (5 ml) and pyridine (0.729 g, 8.66 mmol) was stirred at room temperature until no starting material was visible by TLC. The reaction mixture was concentrated and the residue was taken up in ethyl ether, washed with 10% hydrochloric acid, saturated sodium bicarbonate, aqueous 5% cupric sulfate solution, water, saturated sodium chloride, dried over magnesium sulfate, filtered and concentrated to give the title compound which was carried on without further purification.

IR (neat): 2940, 1740, 1250 cm$^{-1}$.

$^1$H NMR (CDCl$_3$): 7.64 (s, 1H), 6.63 (s, 1H), t, 1H, J=6.9 Hz), 3.64 (t, 2H, J=6.6 Hz), 2.09 (s, 3H), 1.73 to 2.00 (m, 2H), 1.50 to 1.60 (m, 2H), 1.25 to 1.45 (m, 10H), 0.94 (s, 9H), 0.29 (s, 9H), 0.09 (s, 6H).

$^{13}$C NMR (CDCl$_3$): 170.6, 161.2, 144.4, 124.9, 118.6, 68.6, 63.3, 34.8, 32.8, 29.4, 29.3, 29.2, 26.0, 25.8, 25.5, 21.4, −1.7.

m/z Calculated for C$_{23}$H$_{43}$O$_4$Si$_2$ (M+−CH$_3$): 439.2700; obtained (CI+): 439.2704.

4-(1-Acetoxy-9-hydroxynonyl)-2-trimethylsilylfuran 4-(1-Acetoxy-9-t-butyldimethylsiloxynonyl)-2-trimethylsilylfuran (1.00 g, 2.21 mmol) was stirred at 35° for 36 hours in a mixture of acetic acid-water-tetrahydrofuran (1:1:1). The reaction mixture was concentrated and the residue was taken up in ethyl ether, washed with 10% hydrochloric acid, saturated sodium bicarbonate, water, saturated sodium chloride solution, dried over magnesium sulfate, filtered and concentrated to a pale oil. Purification by flash chromatography (silica, 10% ethyl acetate/hexane) gave the desired alcohol.

IR (CHCl$_3$): 3615, 3430 (br), 2920, 1720, 1230 cm$^{-1}$.

$^1$H NMR (CDCl$_3$): 7.64 (s, 1H), 6.63 (s, 1H), 5.81 (t, 1H, J=6.9 Hz), 3.65 (t, 2H, J=6.6 Hz), 2.26 (s, 1H), 2.08 (s, 3H), 1.70 to 1.95 (m, 2H), 1.53 to 1.67 (m, 2H), 1.23 to 1.46 (m, 10H), and 0.29 (s, 9H).

$^{13}$C NMR (CDCl$_3$): 170.6, 161.1, 144.3, 124.8, 118.5, 68.5, 62.7, 34.6, 32.6, 29.3, 29.2, 29.0, 25.6, 25.4, 21.2, −1.8.

m/z Calculated for C$_{18}$H$_{32}$O$_4$Si (M+): 340.2070; obtained (CI+): 340.2072.

4-(1,9-Diacetoxynonyl)-2-trimethylsilylfuran

To 4-(1-acetoxy-9-hydroxynonyl)-2-trimethylsilylfuran (0.075 g, 0.221 mmol) and pyridine (0.056 g, 0.662 mmol) in tetrahydrofuran (2 ml) under argon at 0° was added dropwise acetyl chloride (0.052 g, 0.662 mmol). The mixture was warmed to room temperature, stirred for one hour, quenched with water and extracted into ethyl ether. The organic portion was washed with 10% hydrochloric acid, saturated sodium bicarbonate, aqueous 5% cupric sulfate solution, water, saturated sodium chloride solution, dried over magnesium sulfate, filtered and concentrated to an oil. Purification by flash chromatography (silica, 5 to 10% ethyl acetate/hexane) gave the desired product.

IR (CHCl$_3$): 3010, 2940, 1725, 1370, 1750 cm$^{-1}$.

$^1$H NMR (CDCl$_3$): 7.57 (s, 1H), 6.56 (s, 1H), 5.74 (t, 1H, J=6.9 Hz), 4.02 (t, 2H, J=6.7 Hz), 2.01 (s, 6H), 1.65 to 1.91 (m, 2H), 1.54 to 1.65 (m, 2H), 1.18 to 1.40 (m, 10H), and 0.22 (s, 9H).

$^{13}$C NMR (CDCl$_3$): 171.1, 170.4, 161.1, 144.4, 124.9, 118.5, 68.4, 64.5, 34.7, 29.2, 29.1, 28.5, 25.8, 25.4, 21.2, 20.9, and −1.8.

m/z Calculated for C$_{20}$H$_{34}$O$_5$Si (M+): 382.2175; obtained (CI+): 382.2196.

4-(1,9-Diacetoxynonyl)-5-hydroxy-2(5H)-furanone

A stirred solution of 4-(1,9-diacetoxynonyl)-2-trimethylsilylfuran (0.075 g, 0.196 mmol) and Rose Bengal (2 mg) in acetone (70 ml) was flushed with oxygen and cooled to −78° C. The solution was subsequently irradiated with a 150 Watt flood lamp while under constant positive pressure of oxygen until starting material was no longer visible by TLC. The solution was warmed to room temperature and concentrated to a pink oil. Purification by flash chromatography (silica, 5 to 50% ethyl acetate/hexane) gave the desired hydroxybutenolide.

IR (CHCl$_3$): 3500 (br), 3020, 2930, 2860, 1755, 1730, 1370 cm$^{-1}$.

$^1$H NMR (mixture of diastereomers) (CDCl$_3$): 6.00 to 6.25 (brs, 1H), 5.98 (s, 1H), 5.75 to 5.90 (brs, 1H), 5.53 (brt, 1H, J=5.7 Hz), 4.05 (t, 2H, J=6.7 Hz), 2.14 (s, 3H), 2.06 (s, 3H), 1.70 to 1.94 (m, 2H), 1.55 to 1.70 (m, 2H), 1.20 to 1.50 (m, 10H).

$^{13}$C NMR (mixture of diastereomers) (CDCl$_3$): 171.7, 170.8, 170.2, 166.9, 118.5, 118.4, 98.0, 69.5, 64.6, 32.8, 29.1, 28.9, 28.4, 25.7, 24.8, 21.0, and 20.8.

m/z Calculated for C$_{17}$H$_{27}$O$_7$ (MH+): 343.1757; obtained (CI+): 343.1775.

EXAMPLE 66

4-(1-Acetoxy-9-carboxynonyl)-2-trimethylsilylfuran

To a solution of 4-(1-acetoxy-9-hydroxynonyl)-2-trimethylsilylfuran (0.176 g, 0.518 mmol) in acetone (5 ml) at room temperature was added Jones reagent until the mixture remained orange. The mixture was then taken up in ethyl ether, filtered through celite, washed with saturated sodium bicarbonate, water, saturated sodium chloride solution, dried over magnesium sulfate, refiltered, and concentrated to give an oil which was carried on without further purification.

IR (CHCl$_3$): 3100 (very broad), 2930, 1710, 1250 cm$^{-1}$.

$^1$H NMR (CDCl$_3$): 8.0 to 8.5 (brs, 1H), 7.62 (s, 1H), 6.62 (s, 1H), 5.80 (t, 1H, J=6.9 Hz), 2.37 (2H, t, J=7.3 Hz), 2.08 (s, 3H), 1.80 to 1.97 (m, 2H), 1.58 to 1.74 (m, 2H), 1.25 to 1.50 (m, 8H), and 0.28 (s, 9H).

$^{13}$C NMR (CDCl$_3$): 179.4, 170.7, 161.1, 144.4, 124.8, 118.5, 68.5, 34.6, 33.9, 29.0, 28.9, 25.4, 24.6, 21.2, −1.8.

m/z Calculated for C$_{18}$H$_{30}$O$_5$Si (M+): 354.1863; obtained (CI+): 354.1868.

4-(1-Acetoxy-9-carboxynonyl)-5-hydroxy-2(5H)-furanone

A stirred solution of 4-(1-acetoxy-9-carboxynonyl)-2-trimethylsilylfuran (0.0262 g, 0.074 mmol) and Rose Bengal (1 mg) in acetone (7 ml) was flushed with oxygen and cooled to −78°. The solution was subsequently irradiated with a 150 Watt flood lamp while under constant positive pressure of oxygen until starting material was no longer visible by TLC. The solution was warmed to room temperature and concentrated to a pink oil. Purification by preparative plate chromatography (silica, 100% ethyl acetate) gave the desired hydroxybutenolide.

IR (CHCl$_3$): 3250 (very broad), 2920, 1740, 1705 cm$^{-1}$.

$^1$H NMR (mixture of diastereomers) (CDCl$_3$): 6.09 (brs, 1H); 5.99 (s, 1H), 5.48 (t, 1H, J=6.1 Hz), 5.3 (very broad s, 2H), 2.36 (t, 2H, 7.4 Hz), 2.14 (s, 3H), 1.73 to 1.90 (m, 2H), 1.55 to 1.70 (m, 2H) and 1.20 to 1.50 (m, 8H).

$^{13}$C NMR (mixture of diastereomers) (CDCl$_3$): 179.1, 171.1, 170.0, 166.9, 118.7, 98.0, 69.6, 33.8, 32.8, 28.6, 24.6, 24.4, and 20.9.

m/z Calculated for C$_{15}$H$_{23}$O$_7$(M+H)+: 315.1444, found 315.1445

EXAMPLE 67

4-(1-Acetoxy-9-hydroxynonyl)-5-hydroxy-2(5H)-furanone

A stirred solution of 4-(1-acetoxy-9-hydroxynonyl)-2-trimethylsilylfuran (0.080 g, 0.235 mmol) and Rose Bengal (2 mg) in acetone (15 ml) was flushed with oxygen and cooled to −78°. The solution was then irradiated with a 150 Watt flood lamp while under constant positive pressure of oxygen until starting material was no longer visible by TLC. The solution was warmed to room temperature and concentrated to a pink oil. Purification by flash chromatography (silica, 50% ethyl acetate/hexane) gave the desired hydroxybutenolide.

IR (CHCl$_3$): 3350 (br), 2930, 1750 cm$^{-1}$.

$^1$H NMR (mixture of diastereomers) (CDCl$_3$): 6.5 (brs, 1H), 6.07 (brs, 1H), 5.95 (m, 1H), 5.55 (brs, 1H), 3.62 (t, 2H, J=6.6 Hz), 2.60 (brs, 1H), 2.14 (s, 3H), 1.70 to 1.90 (m, 2H), 1.48 to 1.60 (m, 2H), 1.20 to 1.44 (m, 10H).

$^{13}$C NMR (mixture of diastereomers) (CDCl$_3$): 170.8, 170.7, 167.0, 118.2 and 118.0, 98.1, 69.7 and 69.6, 62.8, 32.6, 32.2, 29.0, 28.7, 25.4, 24.7, 20.8.

MS exact mass calculated for C$_{15}$H$_{23}$O$_7$ (M+H)+ 315.1444, found 315.1445.

EXAMPLE 68

1-Bromo-11-t-butyldimethylsiloxyundecane

To a stirred solution of 8-bromo-1-undecanol (2.02 g, 8.0 mmol) and imidazole (1.3 g, 19 mmol) at 0° under nitrogen in dimethylformamide (4 ml) was added t-butyldimethylsilylchloride (1.46 g, 9.6 mmol). After 1.5 hours the solution was warmed to room temperature, stirred an additional 1.5 hours, and poured into ethyl ether and water. The organic portion was washed successively twice with water, twice with 10% hydrochloric acid solution, once with water, once with saturated sodium bicarbonate solution, once with water, once with sodium chloride, dried over magnesium sulfate, filtered and concentrated to give the silyl ether as a yellow oil. This material was used without further purification.

IR (film): 1460 cm$^{-1}$.

$^1$H NMR (CDCl$_3$): 3.61 (t, 2H, J=6.6 Hz), 3.42 (t, 2H, J=6.8 Hz), 1.87 (p, 2H, J=7.3 Hz), 1.6-1.2 (m, 16H), 0.06 (s, 9H), and 0.02 (s, 6H).

$^{13}$C NMR (CDCl$_3$): 63.4, 34.1, 32.9, 29.6, 29.5, 28.8, 28.2, 26.0, 25.9, 25.7, 18.4, 0.06.

Calculated for $C_{17}H_{38}BrOSi$: 365.1875 $(M+H)^+$; obtained $(EI+)$: 365.1862.

4-(12-t-butyldimethylsiloxy-1-hydroxydodecyl)-2-trimethylsilylfuran

To a stirred suspension of magnesium turnings (0.142 g, 5.9 mmol) in tetrahydrofuran (1 ml) at room temperature under nitrogen was added a solution of 1-bromo-11-t-butyldimethylsiloxyundecane (1.06 g, 2.9 mmol) in tetrahydrofuran (1.5 ml). This mixture was heated to reflux and stirred for 1 hour, then cooled to 0° and diluted with tetrahydrofuran (3 ml). Trimethylsilyl-3-furanaldehyde (0.491 g, 2.9 mmol) was added dropwise in 2 ml of tetrahydrofuran. The solution was stirred for 1 hour at 0°, 4.5 hours at room temperature, quenched with saturated ammonium chloride solution and poured into ethyl ether. The organic portion was washed twice with water, once with saturated sodium chloride solution, dried over magnesium sulfate, filtered and concentrated to give a yellow liquid. The alcohol ($R_f$=0.33, 20% ethyl ether/hexane) was purified by flash chromatography (silica, 10-15% ethyl ether/petroleum ether) to give a pale oil.

IR (film): 3350 (br) cm$^{-1}$.

$^1$H NMR (CHCl$_3$): 7.57 (s, 1H), 6.64 (s, 1H), 4.65 (brt, 1H), 3.61 (t, 2H, J=6.6 Hz), 1.8-1.2 (m, 20H), 0.91 (s, 9H), 0.27 (s, 6H), and 0.06 (s, 3H).

$^{13}$C NMR (CDCl$_3$): 161.4, 143.1, 129.2, 118.3, 67.0, 63.4, 37.9, 32.9, 29.6, 29.5, 26.0, 25.8, 18.4, 15.3, 0.02 and −1.6.

m/z Calculated for $C_{25}H_{50}O_3Si_2$ $(M^+)$: 454.3299; obtained $(EI+)$: 454.3288.

4-(12-t-butyldimethylsiloxy-1-hydroxydodecyl)-5-hydroxy-2(5H)-furanone

A stirred solution of 4-(12-t-butyldimethylsilyoxy-1-hydroxydodecyl)-2-trimethylsilylfuran (0.101 g, 0.22 mmol) and Rose Bengal (trace) in tetrahydrofuran (15 ml) was flushed with oxygen and cooled to −78°. The solution was irradiated with a 200 Watt flood lamp while under a constant positive pressure of oxygen until starting material was no longer visible by TLC (about 1 hour). The solution was warmed to room temperature, concentrated to a pink oil, and purified by preparative thin layer chromatography (1000μ, silica plate, 60% hexane/ethyl acetate). The desired hydroxybutenolide was obtained as an oil.

IR (CHCl$_3$): 3400 (br), 1760, 1465 cm$^{-1}$.

$^1$H NMR (CDCl$_3$): 6.1 (brs, 1H), 6.03 (bs, 1H), 4.58 (brs, 1H), 3.60 (t, 2H, J=6.6 Hz) 3.4 (brs, 1H), 1.8-1.2 (m), 0.90 (s, 9H), and 0.05 (s).

$^{13}$C NMR (CDCl$_3$): 171.7, 117.3, 98.2, 68.0, 63.4, 35.3, 35.1, 32.8, 29.5, 29.3, 26.0, 25.7, 25.1, 18.4, and −0.03.

m/z Calculated for $C_{22}H_{43}O_5Si$ $(M+H)^+$: 415.2880; obtained $(CI+)$: 415.2874.

EXAMPLE 69

4-(1-Acetoxy-12-t-butyldimethylsilyloxydodecyl)-5-hydroxy-2(5H)-furanone

A stirred solution of 4-(1-acetoxy-12-t-butyldimethylsilyloxydodecyl)-2-trimethylsilylfuran (0.102 g, 0.2 mmol) and Rose Bengal (trace) in tetrahydrofuran (25 ml) was flushed with oxygen and cooled to −78°. The solution was irradiated with a 200 Watt flood lamp while under a constant positive pressure of oxygen until starting material was no longer visible by TLC (about 1 hour). The solution was warmed to room temperature, concentrated to a pale oil, and purified by preparative thin layer chromatography (30% ethyl acetate/hexane). The desired hydroxylutenolide was obtained as a clear oil.

IR (CHCl$_3$): 3350 (br), 1760, 1745 cm$^{-1}$.

$^1$H NMR (mixture of diastereomers) (CDCl$_3$): 6.21 (brs, 0.25H), 6.0 (m, 1.75H), 5.50 (brt, 1H), 5.35 (brs, 1H), 3.62 (t, 2H, J=6.7 Hz), 2.15 and 2.13 (2s, 3H), 1.9-1.2 (m), 0.90 (s, 9H), and 0.02 (s 3H).

$^{13}$C NMR (CDCl$_3$) (mixture of diastereomers): 171.2, 170.1, 167.2, 166.7, 119.1, 118.4, 98.0, 69.9 and 69.3, 63.5, 33.1, 32.9, 29.9, 29.6, 29.5, 29.3, 29.2, 26.0, 25.8, 25.1, 25.0, 20.9, 18.4, and 0.05.

m/z Calculated for $C_{24}H_{45}O_6Si$ $(M+H)^+$: 457.2985; obtained $(CI+)$: 457.2966.

EXAMPLE 70

5-(1-Naphthyl)-pent-4-yn-1-ol

A mixture of 1-iodonaphthalene (6 g, 23.6 mmol), 4-pentyn-1-ol (2.38 g, 28.3 mmol), palladium (II) acetate (5 mg), triphenylphosphine (5 mg), copper (I) iodide (5 mg) in triethylamine (50 ml) was refluxed under argon for 17 hours. After cooling, the mixture was acidified with ice-cold dilute hydrochloric acid and extracted with ethyl ether. Evaporation of the dried (magnesium sulfate) extracts gave an oil, which was purified by flash chromatography on silica using 30% ethyl acetate/hexane. Fractions with $R_f$ of about 0.20 on evaporation gave the title alkynol as a deep yellow oil.

$^1$H NMR (CDCl$_3$): 1.74 (br, 1H), 1.99 (p, 2H, J=6.6 Hz), 2.74 (t, 2H, J=7.0 Hz), 3.93 (t, 2H, J=6.0 Hz), 7.40-7.90 (m, 7H), and 8.35 (d, 1H, J=8.0 Hz).

$^{13}$C NMR (CDCl$_3$): 16.1, 31.4, 61.3, 78.9, 94.4, 121.3, 125.0, 126.0, 126.1, 126.4, 127.9, 128.1, 129.9, 133.0 and 133.2.

MS m/e (% abundance): 210 $(M^+, 100)$, 191 (19), 165 (71) and 141 (15).

1-Bromo-5-(1-naphthyl)-pent-4-yne

Bromine (a 2M solution in dichloromethane: 950 mg, 5.95 mmol) was added to a 0° solution of 1,2-bis(diphenyl)phosphinoethane (1.2 g, 2.97 mmol) in dichloromethane (15 ml). A solution of 5-(1-naphthyl)-4-pentyne-1-ol (500 mg, 2.38 mmol) in dichloromethane (2 ml) was added to the solution. The solution was warmed to room temperature and stirring continued for 1.5 hours. The solution was diluted with ethyl ether, then pentane, filtered through a thin pad of silica and the solvent removed. The resulting oil was purified by flash chromatography (hexane) to give the title bromide.

$^1$H NMR (CDCl$_3$): 8.3 (d, 1H, J=7.8 Hz), 7.7 (m, 2H), 7.5 (m, 4H), 3.67 (t, 2H, J=4.1 Hz), 2.78 (t, 2H, 6.6 Hz), and 2.26 (m, 2H).

MS m/e (% abundance): 274/272 $(M^+, 36/36)$, 193 (22), 179 (11), 178 (28), 166 (16), 165 (100), 164 (20) and 163 (26).

3-[1-Acetoxy-6-(1-naphthynl)-5-hexyl]-5-trimethylsilyl-furan

Tert-Butyl lithium (a 1.7M solution in hexane, 13 ml, 2.2 mmol) was added to a solution of 5-(1-naphthyl)-1-bromopent-4-yne (300 mg, 1.1 mmol) in tetrahydrofuran (2 ml) at −78° under nitrogen. After 30 minutes, a solution of 5-trimethylsilyl-3-furaldehyde (168 mg, 0.99 mmole) in tetrahydrofuran (0.5 ml) was added. Stirring was continued for 2 hours, then acetic anhydride (224 mg, 2.2 mmol) was added and the solution stirred at room temperature overnight. The mixture was quenched with water. Extraction (ethyl ether) and evaporation of the dried (magnesium sulfate) extracts gave an oil, which was flash chromatographed on silica gel using 15% ethyl ether/hexane. The title compound was obtained as a yellow oil.

$^1$H NMR (CDCl$_3$): 8.31 (d, 1H, J=7 Hz), 7.82 (m, 2H), 7.63 (m, 2H), 7.5 (m, 2H), 7.39 (t, 1H, J=7.8 Hz), 6.62 (s, 1H), 5.88 (t, 1H, J=6.95 Hz), 2.61 (t, 2H, J=6.9 Hz), 2.1 (m, 2H), 1.75 (m, 2H), and 0.25 (s, 9H).

$^{13}$C NMR (CDCl$_3$): 170.5, 145.7, 144.5, 133.4, 133.1, 130.0, 128.2, 128.0, 126.5, 126.2, 125.3, 125.2, 124.6, 120.3, 120.1, 94.4, 79.1, 76.6, 68.1, 57.7, 34.0, 24.9, 21.3, 21.0, 19.4, −1.7.

4-[1-Acetoxy-6-(1-naphthyl)-5-hexynyl]-5-hydroxy-2(5H)-furanone

A mixture of 3-[1-acetoxy-6-(1-napthyl)-5-hexynyl]-5-trimethylsilylfuran (63.3 mg, 0.16 mmol) and Rose Bengal (5 mg) in acetone (10 ml) was exposed to singlet oxygen at −78° for two hours. The residue, after solvent removal, was purified by preparative TLC (80% ethyl ether/hexane). The title compound was obtained as a yellow oil.

$^1$H NMR (CDCl$_3$): 8.3 (d, 1H, J=8 Hz), 7.8 (m, 2H), 7.2 (m, 4H), 6.2 (brs, 1H), 6.0 (brs, 1H), 5.6 (t, 1H, J=6.8 Hz), 2.6 (t, 2H, J~6.8 Hz), 2.1 (m, 5H), and 1.8 (m, 2H).

$^{13}$C NMR (CDCl$_3$): 170.9, 169.8, 166.6, 133.3, 130.1, 128.3, 126.6, 126.3, 126.0, 125.2, 121.1, 119.3, 118.7, 97.8, 93.5, 97.7, 69.3, 68.8, 65.9, 32.1, 24.2, 20.9, 20.8, 19.2, 15.2.

MS exact mass calculated for C$_{22}$H$_{20}$O$_5$ 364.13107 (M+), found 364.1295.

EXAMPLE 71

5-(1-Naphthyl)-pent-4-yn-1-ol

A mixture of 1-iodonaphthalene (6 g, 23.6 mmol), 4-pentyn-1-ol (2.38 g, 28.3 mmol), palladium (II) acetate (5 mg), triphenylphosphine (5 mg), copper (I) iodide (5 mg) in triethylamine (50 ml) was refluxed under argon for 17 hours. After cooling, the mixture was acidified with ice-cold dilute hydrochloric acid and extracted with ethyl ether. Evaporation of the dried (magnesium sulfate) extracts gave an oil, which was purified by flash chromatography on silica using 30% ethyl acetate/hexane). Fractions with R$_f$ of about 0.20 on evaporation gave the title alkynol as a deep yellow oil.

$^1$H NMR (CDCl$_3$): 1.74 (br, 1H), 1.99 (p, 2H, J=6.6 Hz), 2.74 (t, 2H, J=7.0 Hz), 3.93 (t, 2H, J=6.0 Hz), 7.40–7.90 (m, 7H) and 8.35 (d, 1H, J=8.0 Hz).

$^{13}$C NMR (CDCl$_3$): 16.1, 31.4, 61.3, 78.9, 94.4, 121.3, 125.0, 126.0, 126.1, 126.4, 127.9, 128.1, 129.9, 133.0 and 133.2.

MS m/e (% abundance): 210 (M+, 100), 191 (19), 165 (71) and 141 (15).

5-(1-Naphthyl)-pentan-1-ol

A mixture of 5-(1-naphthyl)-4-pentyn-1-ol (500 ng, 2.37 mmol) and 5% palladium on barium sulfate (5 mg) in ethyl ether (30 ml) was stirred at room temperature under a hydrogen atmosphere for two days. Solvent removal, after filtration through celite, gave the title compound as a yellow oil.

$^1$H NMR (CDCl$_3$): 8.0 (d, 1H, J=7.8 Hz), 7.85 (d, 1H, J=7.11 Hz), 7.69 (d, 1H, J=7.9 Hz), 7.48 (m, 2H), 7.36 (m, 2H), 3.6 (t, 2H, J=6.7 Hz), 3.08 (t, 2H, J=7.6 Hz), 1.7 (m, 2H), 1.6 (m, 2H), and 1.26 (m, 2H).

1-Bromo-5-(1-naphthyl)-pentane

Bromine (a 2M solution in dichloromethane; (912.7 mg, 5.71 mmol) was added to a 0° solution of 1,2-bis(diphenyl)phosphinoethane (1.1 g, 2.85 mmol) in dichloromethane (15 ml). A solution of 5-(1-naphthyl)-pentan-1-ol (489 mg, 2.28 mmol) in dichloromethane (5 ml) was added to the solution at 0°. The solution was warmed to room temperature and stirred 2 hours. Ethyl ether then pentane was added, the solution was filtered through a thin pad of silica gel and the solvent evaporated. The resulting oil was flash chromatographed to give the title bromide as a colorless oil.

$^1$H NMR (CDCl$_3$): 8.0 (d, 1H, J=7.8 Hz), 7.8 (d, 1H, J=7.4 Hz), 7.7 (d, 1H, J=8.3 Hz), 7.4 (m, 4H), 3.4 (t, 2H, J=6.8 Hz), 3.1 (t, 2H, J=7.5 Hz), 1.9 (m, 2H), 1.8 (m, 2H), and 1.58 (m, 2H).

3-[1-Acetoxy-6-(1-naphthyl)hexyl]-5-trimethylsilylfuran

Tert-butyl lithium (a 1.7M solution in hexane (1.27 ml, 2.16 mmol) was added to a −78° solution of 1-bromo-5-(1-naphthyl)-pentane (300 mg, 1.08 mmol) in tetrahydrofuran (2 ml) under nitrogen. After stirring for 30 minutes at −78°, a solution of 5-trimethylsilyl-3-furaldehyde (182 mg, 1.08 mmol) in tetrahydrofuran (0.5 ml) was added and the solution was stirred 2 hours at room temperature. Acetic anhydride (20 mg, 0.2 mmol) was added and the solution stirred at room temperature overnight. The reaction was quenched with water. Extraction (ethyl ether) and evaporation of the dried (magnesium sulfate) extracts gave an oil. Purification of the crude material by preparative TLC (developed with 10% ethyl ether/hexane) gave the title compound as a yellow oil.

$^1$H NMR (CDCl$_3$): 8.01 (d, 1H, J=7.7 Hz), 7.85 (d, 1H, J=7.5 Hz), 7.7 (d, 1H, J=8.2 Hz), 7.58 (s, 1H), 7.4 (m, 4H), 6.57 (s, 1H), 5.76 (t, 1H, J=6.6 Hz), 3.04 (t, 2H, 7.8 Hz), 2.01 (s, 3H), 1.85 (m, 2H), 1.74 (m, 2H), 1.4 (m, 4H), and 0.25 (s, 9H).

$^{13}$C NMR (CDCl$_3$): 170.5, 161.2, 144.4, 138.6, 133.8, 131.8, 128.7, 126.4, 125.8, 125.6, 125.5, 125.3, 124.8, 123.8, 118.5, 68.5, 34.7, 32.9, 30.6, 29.3, 25.4, 21.3, and −1.7.

MS exact mass calculated for C$_{25}$H$_{32}$O$_3$Si (M+) 408.212, found 408.2113.

3-[1-Acetoxy-6-(1-naphthyl)hexyl]-5-hydroxy-2(5H)-furanone

A mixture of 3-[1-acetoxy-6-(1-naphthyl)hexyl]-5-trimethylsilylfuran (23 mg, 0.056 mmol) and Rose Bengal (5 mg) in acetone (20 ml) at −78° was exposed to singlet oxygen for 1.5 hours. The residue, after solvent removal, was purified by preparative TLC (developed with 60% ethyl ether/hexane). The title compound was obtained as a yellow oil.

$^1$H NMR (CDCl$_3$): 8.01 (d, 1H, J=7.7 Hz), 7.8 (d, 1H, J=7.4 Hz), 7.7 (d, 1H, J=8.2 Hz), 7.4 (m, 4H), 6.15 (br, 1H), 5.95 (br, 1H), 5.41 (br, 1H), 3.06 (t, 2H, J=7.6 Hz), 2.1 (s, 3H), 1.8 (m, 6H), and 1.35 (m, 2H).

$^{13}$C NMR (CDCl$_3$): 171.2, 169.7, 166.9, 138.3, 133.8, 131.7, 128.8, 126.6, 126.3, 125.9, 125.7, 125.5, 125.4, 123.7, 119.1, 118.5, 97.9, 76.6, 76.3, 76.2, 69.7, 69.1, 33.0, 32.9, 30.6, 30.4, 29.1, 24.9, 20.8, and −0.025.

EXAMPLE 72

3-(1-Acetoxy-6-phenylhexyn-2-yl)-5-trimethylsilylfuran n-Butyl lithium (a 1.6M solution in hexane; 0.9 ml, 1.44 mmol) was added dropwise to a solution of 5-phenyl-1-pentyne (198.1 mg, 1.38 mmol) in tetrahydrofuran (4 ml) at 0° under argon. After 30 minutes, a solution of 5-trimethylsilyl-3-furaldehyde (231 mg, 1.38 mmol) in tetrahydrofuran (1 ml) was added. Stirring was continued for 1 hour and acetic anhydride (0.4 ml) was added. After 2 hours, the mixture was poured into water and extracted thoroughly with ethyl ether. Evaporation of the dried (magnesium sulfate) extracts gave an oil, which was flash chromatographed on silica using 5% ethyl ether/hexane. Fractions with $R_f$ of about 0.33 on evaporation gave the title ester as an oil.

$^1$H NMR (CDCl$_3$): 0.28 (s, 9H), 1.88 (p, 2H, J=7.3 Hz), 2.12 (s, 3H), 2.29 (t, 2H, J=7.0 Hz), 2.75 (t, 2H, J=7.4 Hz), 6.43 (brs, 1H), 6.72 (s, 1H), 7.15–7.35 (m, 5H) and 7.77 (s, 1H).

MS m/e (% abundance): 354 (M+, 14), 312 (6), 294 (9), 266 (5), 221 (5), 208 (8), 155 (7), 117 (16) and 91 (16).

4-(1-Acetoxy-6-phenylhexyn-2-yl)-5-hydroxy-2(5H)-furanone

A mixture of 3-(1-acetoxy-6-phenylhexyn-2-yl)-5-trimethylsilylfuran (285 mg, 0.8 mmol) and Rose Bengal (5 mg) in tetrahydrofuran (7 ml) was exposed to singlet oxygen at −78° for 2.5 hours. The residue, after solvent removal, was purified by preparative TLC (developed with 60% ethyl ether/hexane). The title furanone was obtained as a yellow oil.

$^1$H NMR (CDCl$_3$): 1.87 (p, 2H, J=7.3 Hz), 2.18 (brs, 3H), 2.28 (brt, 2H), 2.71 (t, 2H, J=7.4 Hz), 5.85 (br, 1H), 6.15 (br, 1H), 6.23 (1H), 6.28 (s, 1H) and 7.15–7.35 (m, 5H).

$^{13}$C NMR (CDCl$_3$): 17.9, 20.6, 29.5, 34.6, 58.7, 59.4, 59.6, 72.5, 72.7, 89.1, 89.2, 97.3, 97.6, 118.4, 121.6, 125.9, 126.2, 128.3, 128.7, 140.9, 162.9, 163.0, 169.6 and 170.2.

MS m/e (% abundance): 332 [(M+NH$_4$)+, 10], 315 [(M+H)+, 1], 297 (4), 274 (20), 273 (53), 256 (20), 255 (100) and 229 (17).

EXAMPLE 73

4-(1-Acetoxy-12-t-butyldimethylsilyloxydodecyl)-2-trimethylsilylfuran

A solution of 4-(12-t-butyldimethylsiloxydodecyl)-2-trimethylsilylfuran (0.46 g, 1.0 mmol) and pyridine (0.3 ml) in acetic anhydride (4 ml) was stirred at 0° under nitrogen for ¼ hour, then 3.5 hours at room temperature. Approximately 1 ml saturated sodium bicarbonate solution was added to the reaction mixture, which was subsequently poured into ethyl ether and water. The organic portion was washed successively three times with water, once with saturated sodium bicarbonate solution, once with water, once with 10% copper sulfate solution, twice with water, once with saturated sodium chloride solution, dried over magnesium sulfate, filtered and concentrated to give a pale oil. The acetate (20% ethyl ether/hexane) was purified by flash chromatography (silica, 7% ethyl ether/petroleum ether) to give a colorless oil.

IR (film): 1740 cm$^{-1}$.

$^1$H NMR (CDCl$_3$): 7.61 (s, 1H), 6.60 (s, 1), 5.78 (t, 1H), 3.62 (t, 2H, J=6.6 Hz), 2.07 (s, 3H), 1.9–1.5 (m, 4H), 1.27 (m, 16H), 0.92 (s, 9H), 0.27 (s, 6H), 0.07 (s, 3H).

$^{13}$C NMR (CDCl$_3$): 170.6, 161.2, 144.5, 125.0, 118.6, 68.6, 63.4, 34.8, 32.9, 29.6, 29.5, 29.3, 26.0, 25.8, 25.6, 21.4, 0.02, and −1.6.

m/z Calculated for C$_{26}$H$_{49}$O$_4$Si$_2$ (M+-CH$_3$): 481.3169; obtained (CH$_4$CI+): 481.3170.

4-(1-Acetoxy-12-hydroxydodecyl)-2-trimethylsilylfuran

A solution of 4-(1-acetoxy-12-t-butyldimethylsilyloxydodecyl)-2-trimethylsilylfuran (0.297 g, 0.6 mmol) and aqueous acetic acid (2 ml, 1:1) in tetrahydrofuran (4 ml) was stirred at room temperature for 60 hours and poured into ethyl ether/saturated sodium bicarbonate solution. The organic portion was washed twice with saturated sodium bicarbonate, once with water, once with saturated sodium chloride solution, dried over magnesium sulfate, filtered and concentrated to give a pale oil. This material was purified by flash chromatography (silica, 30% ethyl acetate/hexane) to give recovered starting material and the desired alcohol.

IR (CHCl$_3$): 3610, 3450 (br), and 1720 cm$^{-1}$.

$^1$H NMR (CDCl$_3$): 7.62 (s, 1H), 6.62 (s, 1H), 5.79 (t, 1H, J=7.0 Hz), 3.65 (t, 2H, J=6.6 Hz), 2.07 (s, 3H), 1.9–1.2 (m, 20H), and 0.28 (s, 9H).

$^{13}$C NMR (CDCl$_3$): 170.6, 161.1, 144.4, 124.9, 118.6, 68.6, 62.9, 34.7, 32.7, 29.5, 29.4, 29.2, 25.7, 25.5, 21.3, and −1.7.

m/z Calculated for C$_{21}$H$_{38}$O$_4$Si(M+): 382.2539; obtained (CI+): 382.2547.

4-(1,12-diacetoxydodecyl)-2-trimethylsilylfuran

To a solution of 4-(1-acetoxy-12-hydroxydodecyl)-2-trimethylsilylfuran and pyridine in tetrahydrofuran at 0° under nitrogen is added acetyl chloride. The mixture is warmed to room temperature, stirred for one hour, quenched with water, and extracted into ethyl ether. The organic portion is washed with 10% hydrochloric acid, saturated sodium bicarbonate, 10% copper sulfate solution, water, saturated sodium chloride solution, dried over magnesium sulfate, filtered and concentrated to give the diacetate.

4-(1,12-diactoxydodecyl)-5-hydroxy-2(5H)-furanone

A stirred solution of 4-(1,11-diacetoxydodecyl)-2-trimethylsilylfuran and Rose Bengal in tetrahydrofuran is flushed with oxygen and cooled to −78°. The solution is irradiated with a 200 Watt flood lamp while under constant positive pressure of oxygen until starting material is no longer visible by TLC. The solution is warmed to room temperature, concentrated and purified by silica chromatography to give the title compound.

EXAMPLE 74

4-(1-Acetoxy-12-hydroxydodecyl)-5-hydroxy-2(5H)-furanone

A stirred solution of 4-(1-acetoxy-12-hydroxydodecyl)-2-trimethylsilylfuran (0.045 g, 0.12 mmol) and Rose Bengal (trace) in tetrahydrofuran (10 ml) was flushed with oxygen and cooled to −78°. The solution was irradiated with a 200 Watt flood lamp while under constant positive pressure of oxygen until starting material was no longer visible by TLC (about 1 hour). The solution was warmed to room temperature, concentrated to a pink gum, and purified by preparative thin layer chromatography (1:1 hexane/ethyl acetate). The hydroxybutenolide was isolated as a gum (1:1 hexane/ethyl acetate).

IR (CHCl$_3$): 3350 (br), 1760, 1745 cm$^{-1}$.

$^1$H NMR (Mixture of diasteriomers) (CDCl$_3$): 6.2 (brs, 0.5H), 6.0 (brm, 1.5H), 5.50 (t, 1H), 3.65 (t, 2H, J=6.6 Hz), 2.16 and 2.12 (2s, 3H), and 2.0–1.3 (m, 20H).

m/z Calculated for C$_{18}$H$_{31}$O$_6$ (MH+): 343.2120; obtained (CI+): 343.2133.

EXAMPLE 75

4-(1-Acetoxy-11-carboxyundecyl)-2-trimethylsilylfuran

To a solution of 4-(1-acetoxy-12-hydroxydodecyl)-2-trimethylsilylfuran (0.083 g, 0.22 mmol) in acetone (5 ml) at room temperature was added Jones reagent until the orange color persisted in the reaction mixture. Ethyl ether was added, and the resulting suspension filtered through celite. The filtrate was then washed twice with water, once with sodium chloride solution, dried over magnesium sulfate, filtered and concentrated to give a colorless gum. The carboxylic acid was purified by preparative thin layer chromatography (40% ethyl acetate/hexane).

IR (CHCl$_3$): 2400–3300 (br), 1725, and 1710 cm$^{-1}$.

$^1$H NMR (CDCl$_3$): 7.60 (s, 1H), 6.60 (s, 1H), 5.77 (t, 1H, J=7 Hz), 2.06 (s, 3H), 2.4–1.2 (m, 20H), 0.26 (s, 3H).

$^{13}$C NMR (CDCl$_3$): 170.6, 161.1, 144.4, 124.9, 118.6, 68.6, 34.7, 29.4, 29.2, 29.1, 25.5, 24.8, 21.3, −1.7.

m/z Calculated for C$_{21}$H$_{36}$O$_5$Si (M+): 396.2332; obtained (CH$_4$CI+): 396.2332.

4-(1-Acetoxy-11-carboxydodecyl)-5-hydroxy-2(5H)-furanone

A stirred solution of 4-(1-acetoxy-11-carboxydodecyl)-2-trimethylsilylfuran and Rose Bengal in tetrahydrofuran is flushed with oxygen and cooled to −78°. The solution is irradiated with 200 Watt flood lamp while under a constant positive pressure of oxygen until starting material is no longer visible by TLC. The solution is warmed to room temperature, concentrated, and the residue purified to give the title compound.

EXAMPLE 76

2-Methoxyethoxymethyl tributylstannylmethyl ether

Tributyltin hydride (2.69 ml, 0.01 mol) was added dropwise to a solution of lithium diisopropylamide (a 1.5M solution in cyclohexane; 6.7 ml, 0.01 mol) in tetrahydrofuran (20 ml) at 0° under argon. After 15 minutes, paraformaldehyde (300 mg, 0.01 mol) was added, followed by 2-methoxyethoxymethyl chloride (1.15 ml, 0.01 mol) after 3 hours. Stirring was continued at room temperature for 12 hours and the mixture was quenched with water. Extraction (ethyl ether) and evaporation of the dried (magnesium sulphate) extracts gave an oil, which was flash chromatographed on silica using 5% ethyl ether/petroleum ether. Fractions with R$_f$ of about 0.24 on evaporation afforded the desired ether as a colorless oil.

$^1$H NMR: (CDCl$_3$) 0.92 (m, 15H), 1.35 (m, 6H), 1.55 (m, 6H), 3.44 (s, 3H), 3.60 (m, 2H), 3.70 (m, 2H), 3.80 (dd, 2H), and 4.65 (s, 2H).

$^{13}$C NMR: (CDCl$_3$) 8.7, 13.5, 27.1, 28.8, 57.7, 66.3, 71.7 and 98.4.

MS m/e (% abundance): 398 ((M+NH$_4$)+, 9), 323(100), 321(74), 319(42), 294(55), 292(38), and 291(16).

4-[1-Dodecanoyloxy-2-(2-methoxyethoxy)methoxyethyl]-2-trimethylsilylfuran n-Butyl lithium (a 1.6M solution in hexane; 0.74 ml, 1.18 mmol) was added to a solution of 2-methoxyethoxymethyl tributylstannylmethyl ether (481.6 mg, 1.18 mmol) in tetrahydrofuran (5 ml) at −78° under argon. After 10 minutes, a solution of 5-trimethylsilyl-3-furaldehyde (198 mg, 1.18 mmol) was added, followed by lauroyl chloride (0.26 ml), 1.18 mmol) after 20 minutes. Stirring was continued at room temperature for 48 hours and the mixture was quenched with water. Extraction (ether) and evaporation of the dried (magnesium sulphate) extracts gave an oil, which was flash chromatographed on silica using 20% ethyl ether/petroleum ether. Fractions with R$_f$ of about 0.27 (30% ethyl ether/petroleum ether) on evaporation afforded the title ester as a pale yellow oil.

$^1$H NMR (CDCl$_3$): 0.26 (s, 9H), 0.89 (t, 3H, J=6.9 Hz), 1.27 (brs, 16H), 1.65 (m, 2H), 2.34 (t, 2H, J=7.7 Hz), 3.41 (s, 3H), 3.58 (m, 2H), 3.67 (m, 2H), 3.84 (m, 2H), 4.77 (s, 2H), 6.05 (dd, 1H, J=7.5 Hz, 3.8 Hz), 6.62 (s, 1H) and 7.66 (s, 1H).

MS m/e (% abundance): 488 ((M+NH$_4$)+, 26), 271 (100), 195 (42), 123 (25) and 90 (18).

4-[1-Dodecanoyloxy-2-(2-methoxyethoxy)methoxyethyl]-5-hydroxy-2(5H)-furanone

A mixture of 4-[1-dodecanoyloxy-2-(2-methoxyethoxy)methoxyethyl]-2-trimethylsilylfuran (229 mg, 0.49 mmol) and Rose Bengal (5 mg) in tetrahydrofuran (7 ml) was exposed to singlet oxygen for 2 hours at −78°. The residue, after solvent removal, was purified by preparative TLC (silica plate; developed with 80% ethyl ether/petroleum ether). The title ester was obtained as a colorless oil.

$^1$H NMR (CDCl$_3$): 0.89 (t, 3H, J=6.9 Hz), 1.27 (brs, 16H), 1.65 (brt, 2H), 2.43 (t, 2H, J=7.8 Hz), 3.40 (s, 3H), 3.05 (m, 2H), 3.30 (m, 2H), 3.95 (m, 2H), 4.74 (s, 2H), 5.70 (brm, 1H), 6.11 (s, 1H), and 6.14 (s, 1H).

$^{13}$C NMR (CDCl$_3$): 14.1, 22.7, 24.8, 29.1, 29.2, 29.3, 29.4, 29.6, 31.9, 34.0, 58.9, 67.2, 67.4, 68.5, 71.7, 95.6, 97.9, 98.1, 120.2, 169.6 and 172.9.

MS m/e exact mass calculated for C$_{22}$H$_{42}$NO$_8$(M+NH$_4$)+ 448.2910, found 448.2890.

EXAMPLE 77

2-Trimethylsilyl-4-vinylfuran n-Butyl lithium (a 1.6M solution in hexane; 2.23 ml, 3.57 mmol) was added dropwise to a suspension of methyltriphenylphosphonium bromide (262 mg, 0.73 mmol) in tetrahydrofuran (8 ml) at 0° under argon. After 20 minutes, a solution of 5-trimethylsilyl-3-furaldehyde (102 mg, 0.61 mmol) in tetrahydrofuran (½ ml) was added. Stirring was continued for 18 hours while the cooling bath attained room temperature. The mixture was quenched with methanol/water (1:1, 20 ml) and extracted with pentane. Evaporation of the dried (magnesium sulphate) extracts gave an oil, which was flash chromatographed on silica using pentane. The title vinylfuran was obtained as a colorless oil.

$^1$H NMR (CDCl$_3$): 0.31 (s, 9H), 5.15 (d, 1H, J=10.2 Hz), 5.50 (d, 1H, J=17.6 Hz), 6.64 (dd, 1H, J=17.6 Hz, 10.2 Hz), 6.82 (s, 1H), and 7.65 (s, 1H).

MS m/e (% abundance): 184 ((M+NH$_4$+), 22), 158 (14), 108 (26), 90 (23), 74 (68) and 60 (100).

4-(1,2-Dihydroxyethyl)-2-trimethylsilylfuran

2-Trimethylsilyl-4-vinylfuran (272 mg, 1.64 mmol) was added to a mixture of 4-methylmorpholine N-oxide (203 mg, 1.74 mmol), osmium tetroxide (a 2.5% by weight solution in tert-butanol; 0.1 ml), water (3.5 ml) and acetone (1.5 ml) at room temperature under argon. Stirring was continued for 19 hours and most of the acetone was evaporated under vacuum. Sodium bisulphite was added to the residue and the pH of the solution was adjusted to 1 with dilute sulphuric acid. After being saturated with sodium chloride, the solution was extracted thoroughly with ethyl acetate. Evaporation of the dried (magnesium sulphate) extracts afforded an oil, which was purified by preparative TLC (silica plate; developed with 60% ethyl ether/petroleum ether). The title diol was obtained as a pale yellow oil.

$^1$H NMR (mixture of diasteriomers) (CDCl$_3$): 0.29 (s, 9H), 0.35 (s, 9H), 2.2 (br, 2H), 3.70–3.85 (m, 2H), 4.85 (dd, 1H, J=3.9 Hz, 7.3 Hz), 4.95 (m, 2H), 6.50 (d, 1H), 6.65 (s, 1H), 7.60 (d, 1H) and 7.66 (s, 1H).

$^{13}$C NMR (CDCl$_3$): −1.8, −1.0, 66.9, 67.3, 67.7, 108.4, 118.3, 124.3, 134.2, 143.7, 146.5, 156.2 and 161.5.

MS m/e (% abundance): 200 (M+, 18), 169 (100), 153 (22), 139 (9) and 73 (73).

4-(1,2-Didodecanoyloxyethyl)-2-trimethylsilylfuran tert-Butyl lithium (a 1.7M solution in pentane; 0.34 ml, 0.57 mmol) was added dropwise to a solution of 4-(1,2-dihydroxyethyl)-2-trimethylsilylfuran (52 mg, 0.26 mmol) in tetrahydrofuran (1 ml) at 0° under argon. After 5 minutes, lauroyl chloride (0.13 ml, 0.57 mmol) was added and stirring was continued at room temperature for 15 hours. The mixture was quenched with water and extracted with ether. Evaporation of the dried (magnesium sulphate) extracts gave an oil, which was purified by preparative TLC (silica plate; developed with 5% ethyl ether/petroleum ether). The title diester was obtained as a pale yellow oil.

$^1$H NMR (CDCl$_3$): 0.28 (s, 9H), 0.91 (t, 6H, J=6.9 Hz), 1.29 (brs, 32H), 1.60 (m, 4H), 2.35 (m, 4H), 4.35 (m, 2H), 6.12 (m, 1H), 6.69 (s, 1H) and 7.67 (s, 1H).

4-(1,2-Didodecanoyloxyethyl)-5-hydroxy-2(5H)-furanone

A mixture of 4-(1,2-didodecanoyloxyethyl)-2-trimethylsilylfuran (97.1 mg, 0.17 mmol) and Rose Bengal (5 mg) in tetrahydrofuran (8 ml) was exposed to singlet oxygen for 2½ hours at −78°. The residue, after solvent removal, was purified by preparative TLC (20×20 cm, 500μ silica plate; developed with 60% ethyl ether/petroleum ether). The title diester was obtained as a colorless waxy solid.

$^1$H NMR (CDCl$_3$) 0.89 (t, 6H, J=6.9 Hz), 1.27 (brs, 16H), 1.65 (m, 4H), 2.34 (t, 2H, J=7.6 Hz), 2.41 (t, 2H, J=8.0 Hz), 4.35–4.55 (m, 2H), 5.75 (t, 1H), 6.09 (s, 1H) and 6.15 (s, 1H).

$^{13}$C NMR (CDCl$_3$): 14.1, 22.7, 24.8, 28.1, 28.3, 28.5, 28.6, 28.7, 29.1, 29.4, 29.5, 29.6, 31.9, 34.0, 62.7, 67.6, 97.7, 121.0, 161.5, 168.9 and 172.5.

MS m/e exact mass calculated for C$_{30}$H$_{56}$NO$_7$ (M+NH$_4$)+ 542.4057, found 542.4054.

EXAMPLE 78

Methyl 3-(2-naphthyl)propen-2-oate

A mixture of 2-naphthaldehyde (4.86 g, 31.1 mmol) and methyl (triphenylphosphoranylidene)acetate (11.45 g, 34.2 mmol) in tetrahydrofuran (50 ml) was stirred at room temperature for 2 days. The residue, after solvent removal, was dissolved in methanol/water (100 ml, 1:1) and extracted with ethyl ether/petroleum ether (7:3). Evaporation of the dried (magnesium sulphate) extracts gave an oil, which was flash chromatographed on silica using 10% ethyl ether/petroleum ether. Fractions with R$_f$ of about 0.18 on evaporation afforded the title ester as colorless shiny plates: mp 93°-4°.

$^1$H NMR (CDCl$_3$): 3.85 (s, 3H), 6.56 (d, 1H, J=16 Hz) and 7.50–8.00 (m, 8H).

MS m/e (% abundance): 212 (M+, 100), 197 (3), 181 (76), 152 (57), 127 (10) and 76 (20).

3-(2-Naphthyl)propan-1-ol

A solution of methyl 3-(2-naphthyl)propen-2-oate (3.22 g, 15.2 mmol) in tetrahydrofuran (15 ml) was added dropwise to a suspension of lithium aluminium hydride (1.73 g, 45.5 mmol) in refluxing tetrahydrofuran (100 ml). After 15 hours reflux, the mixture was cooled and quenched with excess ethyl acetate. Extraction (ethyl ether) and evaporation of the dried (magnesium sulphate) extracts gave an oil, which was flash chromatographed on silica using 40% ethyl ether/petroleum ether. Fraction with R$_f$ of about 0.08 (30% ethyl ether/petroleum ether) on evaporation afforded the title alcohol as a pale yellow viscous oil.

$^1$H NMR (CDCl$_3$): 2.03 (p, 2H, J=7.9 Hz), 2.93 (t, 2H, J=7.3 Hz), 3.76 (t, 2H, J=6.5 Hz) and 7.35–7.90 (m, 7H).

MS m/e (% abundance): 186 (M+, 49), 167 (11), 142 (100), 141 (58), 128 (12) and 115 (21).

(2-Naphthyl)propyl tributylstannylmethyl ether

Potassium hydride (315 mg, 7.87 mmol) was added to a solution of 3-(2-naphthyl)propan-1-ol (1.33 g, 7.16 mmol) in tetrahydrofuran (10 ml) at room temperature under argon. After ½ hour, a solution of tributylstannylmethyliodide (3.09 g, 7.16 mmol) in tetrahydrofuran (2 ml) was added. After stirring at room temperature for 10 days, the mixture was diluted with hexane and washed thoroughly with water. Evaporation of the dried (magnesium sulphate) organic layer gave an oil, which was flash chromatographed on silica using 5% ethyl ether/petroleum ether. The title ether was obtained as a colorless oil.

$^1$H NMR (CDCl$_3$): 0.90 (m, 15H), 1.35 (m, 6H), 1.55 (m, 6H), 1.96 (p, 2H, J=7.9 Hz), 2.85 (t, 2H, J=8.1 Hz), 3.37 (t, 2H, J=5.8 Hz), 3.75 (dd, 2H) and 7.30–7.90 (m, 7H).

$^{13}$C NMR (CDCl$_3$): 9.0, 13.8, 27.3, 29.0, 29.2, 29.3, 31.3, 32.5, 61.8, 74.4, 77.4, 125.0, 125.8, 126.4, 127.4, 127.5, 127.8, 132.0, 133.6 and 139.7.

MS m/e exact mass calculated for C$_{26}$H$_{42}$OSn (M+) 490.2258, found 490.2250

4-[1-Acetoxy-2-[3-(2-naphthyl)propoxy]ethyl]-2-trimethylsilylfuran n-Butyl lithium (a 1.6M solution in hexane; 0.69 ml, 1.1 mmol) was added dropwise to a solution of (2-naphthyl)propyl tributylstannylmethyl ether (511.9 mg, 1.05 mmol) in tetrahydrofuran (5 ml) at −78° under argon. After 5 minutes, a solution of 5-trimethylsilyl-3-furaldehyde (176 mg, 1.05 mmol) in tetrahydrofuran (½ ml) was added, followed by acetic anhydride (0.1 ml, 1.58 mmol) after 25 minutes. Stirring was continued at −78° for 1 hour and the mixture was quenched with water. Extraction (ethyl ether) and evaporation of the dried (magnesium sulphate) extracts gave an oil, which was flash chromatographed using 10% ethyl ether/petroleum ether. The title ester was obtained as a pale yellow oil.

$^1$H NMR (CDCl$_3$): 0.25 (s, 9H), 2.00 (m, 2H), 2.08 (s, 3H), 2.09 (s, 3H), 2.84 (m, 2H), 3.40–3.80 (m, 4H), 5.29 (s, 1H), 6.00 (m, 1H), 6.63 (s, 1H) and 7.30–7.85 (m, 8H).

MS m/e (% abundance): 410 (M$^+$, 5), 350 (21), 170 (14), 169 (100), 141 (53) and 73 (100).

4-[1-Acetoxy-2-[3-(2-naphthyl)propoxy]ethyl]-5-hydroxy-2(5H)-furanone

A mixture of 4-[1-acetoxy-2-[3-(2-naphthyl) propoxy]ethyl]-2-trimethylsilylfuran (230 mg, 0.56 mmol) and Rose Bengal (5 mg) in tetrahydrofuran (7 ml) was exposed to singlet oxygen at −78° C. for 2 hours. The residue, after solvent removal, was purified by preparative TLC (silica plate developed with 60% ethyl ether/petroleum ether). The title furanone was obtained as a pale yellow oil.

$^1$H NMR (CDCl$_3$): 2.02 (p, 2H, J=7.9 Hz), 2.17 (s, 3H), 2.85 (t, 2H, J=7.5 Hz), 3.55 (m, 2H), 3.73 (dd, 1H, J=10.9 Hz, 4.9 Hz), 3.80 (m, 1H), 4.90 (br, 1H), 5.68 (br, 1H), 6.12 (br, 2H) and 7.30–7.90 (m, 7H).

$^{13}$C NMR (mixture of diasteromers) (CDCl$_3$): 18.0, 20.7, 20.8, 30.6, 30.8, 32.1, 58.4, 67.9, 68.7, 69.8, 70.5, 70.7, 70.9, 97.3, 98.1, 119.7, 125.1, 125.9, 126.0, 126.2, 126.4, 126.5, 126.8, 127.1, 127.3, 127.5, 127.8, 127.9, 132.0, 133.5, 138.8, 139.1, 146.9, 170.0 and 170.3.

MS m/e exact mass calculated for C$_{21}$H$_{22}$O$_6$ (M$^+$) 370.1416, found 370.1426.

EXAMPLE 79

4-[1-Hydroxy-2-[3-(2-naphthyl)propoxy]ethyl]-2-trimethylsilylfuran n-Butyl lithium (a 1.6M solution in hexane; 0.56 ml, 0.94 mmol) was added dropwise to a solution of (2-naphthyl)propyl tributylstannylmethyl ether (437 mg, 0.89 mmol), prepared as in Example 3, in tetrahydrofuran (5 ml) at −78° under argon. After 5 minutes, a solution of 5-trimethylsilyl-3-furaldehyde (150 mg, 0.89 mmol) in tetrahydrofuran (1 ml) was added. Stirring was continued at −78° for 2 hours and at room temperature for 1 hour. The mixture was quenched with water and extracted with ethyl ether. Evaporation of the dried (magnesium sulphate) extracts gave an oil, which was flash chromatographed on silica using 30% ethyl ether/hexane. The title alcohol was obtained as a colorless oil.

$^1$H NMR (CDCl$_3$): 0.26 (s, 9H), 2.05 (p, 2H, J=7.5 Hz), 2.89 (t, 2H, J=7.5 Hz), 3.55 (m, 4H), 4.85 (m, 1H), 6.65 (s, 1H), 7.30–7.50 (m, 4H), 7.64 (s, 1H) and 7.75–7.90 (m, 2H).

MS m/e (% abundance): 368 (M$^+$, 23), 350 (9), 169 (100), 141 (55), 115 (15) and 73 (52).

4-[1-Hydroxy-2-[3-(2-naphthyl)propoxy]ethyl]-5-hydroxy-2(5H)-furanone

A mixture of 4-[1-hydroxy-2-[3-(2-naphthyl) propoxy]ethyl]-2-trimethylsilylfuran (160 mg, 0.44 mmol) and Rose Bengal (5 mg) in tetrahydrofuran (6 ml) was exposed to singlet oxygen at −78° for 1½ hours. The residue, after solvent removal, was purified by preparative TLC (silica plate developed with 80% ethyl ether/hexane). The title furanone was obtained as a low-melting off-white solid.

$^1$H NMR (CDCl$_3$): 1.97 (p, 2H, J=7.2 Hz), 2.82 (t, 2H, J=7.4 Hz), 3.50 (m, 4H), 4.73 (br, 1H), 6.09 (s, 1H), 6.14 (s, 1H) and 7.30–7.90 (m, 7H).

$^{13}$C NMR (CDCl$_3$): 30.7, 32.3, 67.4, 71.0, 72.7, 98.0, 119.1, 125.3, 126.0, 126.4, 127.1, 127.4, 127.5, 127.6, 128.0, 132.0, 133.5, 138.9 and 170.8.

MS m/e exact mass calculated for C$_{19}$H$_{20}$O$_5$ (M$^+$) 328.1310, found 328.1291.

EXAMPLE 80

3-(2-Pyridyl)-2-propyn-1-ol

A mixture of 2-bromopyridine (5 g, 31.6 mmol), palladium (II) acetate (5 mg), copper (I) iodide (5 mg), triphenylphosphine (5 mg) in triethylamine (50 ml) was deaerated with argon for 5 minutes. After propagyl alcohol (2.2 ml, 38.0 mmol) was added, the solution was rapidly heated to reflux under argon and conditions maintained for 17 h. On cooling, the mixture was poured into 2M sodium hydroxide (ca. 30 ml) and extracted thoroughly with ethyl acetate. Evaporation of the dried (magnesium sulphate) extracts gave an oil, which was flash chromatographed on silica using 80% ethyl acetate/chloroform. Fractions with R$_f$ of about 0.23 on evaporation gave the title alcohol as a light tan solid: mp 78°–80°.

$^1$H NMR (CDCl$_3$): 3.42 (br, 1H), 4.59 (s, 2H), 7.30 (m, 1H), 7.48 (d, 1H, J=7.9 Hz), 7.71 (dt, 1H, J=7.6 Hz, 1.9 Hz) and 8.60 (d, 1H, J=4.8 Hz).

$^{13}$C NMR (CDCl$_3$): 50.5, 83.4, 89.2, 122.9, 127.1, 136.5, 142.5 and 149.3.

MS m/e (% abundance): 133 (M$^+$, 25), 104 (100) and 78 (29).

3-(2-Pyridyl)-1-propanol

A solution of 3-(2-pyridyl)-2-propyn-1-ol (540 mg, 4.06 mmol) in ethyl acetate (15 ml) and ethanol (3 ml) was hydrogenated over 10% palladium on carbon at room temperature for 13 h. The mixture was filtered through celite and the filtrate on evaporation gave an oil, which was flash chromatographed on silica using 3% methanol/dichloromethane. Fractions with R$_f$ of about 0.09 on evaporation gave the title alcohol as a yellow oil.

$^1$H NMR (CDCl$_3$): 2.02 (p, 2H, J=7.2 Hz), 3.01 (t, 2H, J=7.0 Hz), 3.75 (t, 2H, J=6.8 Hz), 4.3 (br, 1H), 7.15 (m, 2H), 7.65 (dt, 1H, J=7.6 Hz, 1.9 Hz) and 8.52 (d, 1H, J=4.8 Hz).

MS m/e (% abundance): 138 (M$^+$+1, 100), 120 (21) and 93 (18).

3-(2-Pyridyl)propyl tributylstannylmethyl ether

Potassium hydride (52 mg, 1.30 mmol) was added to a solution of 3-(2-pyridyl)propan-1-ol (161.8 mg, 1.18 mmol) in tetrahydrofuran (3 ml) at room temperature under argon. After 30 minutes, a solution of tributylstannylmethyl iodide (510 mg, 1.18 mmol) in tetrahydrofuran (0.5 ml) was added. After stirring was continued at room temperature for 9 days, the mixture was diluted with ether and washed thoroughly with water. Evaporation of the dried (magnesium sulphate) organic layer gave an oil, which was flash chromatographed on silica using 60% ethyl ether/hexane. Fractions with R$_f$ of about 0.53 on evaporation gave the title ether as a bright yellow oil.

$^1$H NMR (CDCl$_3$): 0.95 (m, 15H), 1.35 (m, 6H), 1.55 (m, 6H), 2.0 (p, 2H, J=6.3 Hz), 2.86 (t, 2H, J=7.8 Hz), 3.38 (t, 2H, J=6.3 Hz), 3.74 (t, 2H), 7.15 (m, 2H), 7.60 (dt, 1H, J=7.5 Hz, 1.8 Hz) and 7.55 (bd, 1H).

$^{13}$C NMR (CDCl$_3$): 8.7, 13.5, 27.1, 28.9, 29.4, 34.7, 61.6, 74.4, 120.6, 122.6, 135.8, 148.9 and 161.7.

MS m/e (% abundance): 441 (M+, 1), 384 (47), 383 (18), 382 (35), 381 (14), 380 (20), 354 (18), 338 (30), 235 (19), 211 (10), 179 (29), 177 (27), 175 (17), 150 (11), 121 (22), 120 (100) and 91 (57).

4-[1-Acetoxy-2-[3-(2-pyridyl)propoxy]ethyl]-2-trimethylsilylfuran n-Butyl lithium (a 1.6M solution in hexane; 0.46 ml, 0.74 mmol) was added dropwise to a solution of (2-pyridyl)propyl tributylstannyl ether (309.2 mg, 0.70 mmol) in tetrahydrofuran (5 ml) at −78° under argon. After 5 minutes, a solution of 5-trimethylsilyl-3-furaldehyde (118 mg, 0.70 mmol) in tetrahydrofuran (1.5 ml) was added, followed by acetic anhydride (0.1 ml, 1.05 mmol) after 1 hour. Stirring was continued at −78° for 4 hours and the mixture was quenched with water. Extraction (ethyl ether) and evaporation of the dried (magnesium sulphate) extracts gave an oil, which was flash chromatographed on silica using 40% ethyl acetate/hexane. Fractions with R$_f$ of about 0.12 on evaporation afforded the title ester as a yellow oil.

$^1$H NMR (CDCl$_3$): 0.28 (s, 9H), 2.08 (p, 2H, J=8.1 Hz), 2.12 (s, 3H), 2.89 (t, 2H, J=7.8 Hz), 3.55 (m, 2H), 3.65 (dd, 1H, J=6.6 Hz, 0.9 Hz), 3.77 (dd, 1H, J=10.8 Hz, 3.4 Hz), 6.02 (m, 1H), 6.65 (s, 1H), 7.15 (m, 2H), 7.63 (dt, 1H, J=7.7 Hz, 1.8 Hz), 7.69 (s, 1H) and 8.56 (m, 1H).

MS m/e (% abundance): 362 (M++1, 1), 346 (5), 318 (1), 224 (26), 182 (32), 169 (26), 150 (11), 120 (100), 93 (70) and 92 (11).

4-[1-Acetoxy-2-[3-(2-pyridyl)propoxy]ethyl]-5-hydroxy-2(5H)-furanone

A mixture of 4-[1-acetoxy-2-[3-(2-pyridyl)propoxy]ethyl]-2-trimethylsilylfuran (120 mg, 0.33 mmol) and Rose Bengal (5 mg) in tetrahydrofuran (6 ml) was exposed to singlet oxygen at −78° for 2 h. The residue, after solvent removal, was purified by preparative TLC (silica plate developed with 80% ethyl acetate/hexane). The title furanone was obtained as a colorless oil.

$^1$H NMR (mixture of diasteriomers) (CDCl$_3$): 2.0 (brm, 2H), 2.20 (s, 3H), 2.92 (m, 2H), 3.85 (brm, 2H), 5.85 (br, 1H), 6.11 (brs, 1H), 6.37 (brs, 1H), 7.25 (m, 2H), 7.72 (t, 1H, J=7.6 Hz) and 8.48 (d, 1H, J=4.5 Hz).

$^{13}$C NMR (CDCl$_3$): 20.8, 29.9, 33.7, 68.0–69.0 (br), 98.3 (br), 119.1 (br), 121.7, 123.5, 137.6, 141.8, 160.9, 165.2, 169.7 and 170.1.

MS: Exact mass calculated for C$_{17}$H$_{20}$NO$_5$(M−H)+: 318.1341, found 318.1399.

EXAMPLE 81

3-[1-Hydroxy-2-(2-methoxyethoxy)methoxyethyl]-5-trimethylsilylfuran

A solution of 2-methoxyethoxymethyl tributylstannylmethyl ether (620 mg, 1.5 mmole) in tetrahydrofuran (THF) (5 ml) at −78° C. was treated with n-butyl lithium (92.5M solution in hexane: 0.67 ml, 1.67 mmole). After 10 min., a solution of 5-trimethylsilyl-3-furaldehyde (254 mg, 1.5 mmole) in THF (2 ml) was added. The solution was stirred for 3 hours while the cooling bath warmed to room temperature. The mixture was quenched with water and the aqueous phase extracted with ethyl ether. The combined organic portions were dried over MgSO$_4$, filtered and concentrated. Purification by flash chromatography (silica, 50% ethyl ether/hexane) gave 216.5 mg of the title compound as a light yellow oil.

'H NMR (CDCl$_3$): 7.62 (s, 1H), 6.62 (s, 1H), 4.87 (m, 1H), 4.80 (s, 2H), 3.75 (m, 4H), 3.55 (m, 2H), 3.4 (s, 3H), 0.24 (s, 9H).

$^{13}$C NMR (CDCl$_3$): 160.9, 143.5, 124.9, 118.3, 95.8, 73.4, 71.5, 70.0, 65.8, 58.7, 1.8.

MS m/e exact mass calculated for C$_{13}$H$_{24}$O$_5$Si 288.1393 (M+), found 288.1392.

4-[1-Hydroxy-2-(2-methoxyethoxy)methoxyethyl]-5-hydroxy-2(5H)-furanone

A mixture of 3-[1-hydroxy-2-(2-methoxyethoxy)methoxyethyl]-5-trimethylsilylfuran (135 mg, 0.59 mmole) and Rose Bengal (5 mg) in acetone (30 ml) was exposed to singlet oxygen at −78° C. for 2 hours. The residue, after solvent removal, was purified by preparative TLC (silica plate: developed with 7% methanol/chloroform). The title furanone was obtained as a clear oil.

'H NMR (CDCl$_3$): 6.21 (s, 1H), 6.18 (s, 1H), 4.76 (s+t, 3H), 3.9 (d, J=4.3 Hz, 2H), 3.76 (m, 2H), 3.61 (t, J=4.5 Hz, 2H), 3.43 (s, 3H).

$^{13}$C NMR (CDCl$_3$): 171, 119.1, 98.2, 96.0, 71.5, 70.9, 67.5, 67.3, 58.8.

MS exact mass calculated for C$_{10}$H$_{20}$O$_7$N 266.1239 (M+NH$_4$)+ found 266.1241.

EXAMPLE 82

3-[1-Acetoxy-2-(2-methoxyethoxy)methoxyethyl]-5-trimethylsilylfuran

A solution of 2-methoxyethoxymethyl tributylstannylmethyl ether (620 mg, 1.5 mmole) in tetrahydrofuran (THF) (5 ml) at −78° C. was treated with n-butyl lithium (a 2.5M solution in hexane: 0.67 ml, 1.67 mmole). After 10 min., a solution of 5-trimethylsilyl-3-furaldehyde (254 mg, 1.5 mmole) in THF (2 ml) was added. The solution was stirred for 3 hours while the cooling bath warmed to room temperature. Acetic anhydride (309 mg, 3.03 mmole) was added and the solution stirred at room temperature overnight. The mixture was quenched with water and the aqueous phase extracted with ethyl ether. The combined organic portions were dried over MgSO$_4$, filtered and concentrated. Purification by flash chromatography (silica, 50% ethyl ether/hexane) gave the title compound as a light yellow oil.

'H NMR (CDCl$_3$): 7.70 (s, 1H), 6.65 (s, 1H), 6.04 (m, 1H), 4.80 (s, 2H), 3.9 (m, 2H), 3.72 (m, 2H), 3.59 (m, 2H), 3.44 (s, 3H), 0.29 (s, 9H).

$^{13}$C NMR (CDCl$_3$): 170.3, 161.3, 144.9, 121.7, 118.7, 95.4, 71.6, 70.0, 67.3, 66.9, 58.9, 21.2, −1.8.

MS m/e exact mass calculated for C$_{15}$H$_{26}$O$_6$Si 330.1498 (M+), found 330.1486.

4-[1-Acetoxy-2-(2-methoxyethoxy)methoxyethyl]-5-hydroxy-2(5H)-furanone

A mixture of 3-[1-acetoxy-2-(2-methoxyethoxy)methoxyethyl]-5-trimethylsilylfuran (92.6 mg, 0.28 mmole) and Rose Bengal (5 mg) in acetone (20 ml) was exposed to singlet oxygen at −78° C. for 2 hours. The residue, after solvent removal, was purified by preparative TLC (silica plate: developed with ethyl acetate). The title furanone was obtained as a light yellow oil.

'H NMR (CDCl$_3$): 6.15 (s, 1H), 6.12 (s, 1H), 5.7 (br, 1H), 4.73 (s, 2H), 3.92 (m, 2H), 3.65 (m, 2H), 3.05 (m, 2H), 3.39 (s, 3H), 2.16 (s, 3H).

$^{13}$C NMR (CDCl$_3$): 170.0, 163.8, 120.3, 98.0, 97.7, 71.5, 68.7, 67.3, 67.0, 66.8, 66.7, 65.8, 58.9, 20.7.

MS exact mass calculated for C$_{12}$H$_{22}$O$_8$N 308.1345 (M+NH$_4$)$^+$, found 308.1360.

EXAMPLE 83

(E), (Z)-3-(1-Tridecenyl)-5-trimethylsilylfuran n-Butyl lithium (a 1.6M solution in hexane: 5.58 ml, 8.9 mmol) was added dropwise to a solution of dodecyltriphenylphosphonium bromide (4.57 g, 8.9 mmol) in tetrahydrofuran (35 ml) at 0° under argon. After 25 min., a solution of 5-trimethylsilyl-3-furaldehyde (1 g, 5.9 mmol) in tetrahydrofuran (3 ml) was added. Stirring was continued for 1 hour at 0° and the mixture was quenched with methanol/water (1:1, 60 ml). Extraction (hexane/ether, 1:1), washing (brine) and evaporation of the dried (magnesium sulphate) extracts gave an oil, which was purified by flash chromatography (silica) using 5% ethyl ether/hexane. Fractions with R$_f$ of about 0.8 on evaporation afforded the title olefin as a pale yellow oil.

'H NMR (CDCl$_3$) (E)-isomer: 0.31 (s, 9H), 0.92 (t, 3H, J=7.1 Hz), 1.30 (brs, 18H), 2.29 (q, 2H, J=7.3 Hz), 5.95, 6.00 (dt, 1H, J=15.0 Hz, 7.5 Hz), 6.25 (d, 1H, J=15 Hz), 6.68 (s, 1H) and 7.66 (s, 1H).

(Z)-isomer: 0.30 (s, 9H), 0.92 (t, 3H, J=1 Hz), 1.30 (brs, 18H), 2.15 (q, 2H, J=7.3 Hz), 5.55, 5.60 (dt, 1H, J=11.5 Hz, 5.5 Hz), 6.15 (d, 1H, J=11.5 Hz), 6.77 (s, 1H) and 7.58 (s, 1H). ((E):(Z)=1:2)

MS m/e (% abundance): 320 (M$^+$, 38), 180 (25), 154 (50), 75 (15) and 73 (100).

3-(1,2-Dihydroxytridecyl)-5-trimethylsilylfuran

Pyridine (31 μ, 0.38 mmol), followed by osmium tetroxide (a 2.5% by weight solution in tert-butanol; 5 drops) was added to a solution of (E), (Z)-3-(tridec-1-enyl)-5-trimethylsilyl]furan (111 mg, 0.35 mmol) and N-methylmorpholine N-oxide (45 mg, 0.38 mmol) and acetone (2 ml) at room temperature. After stirring for 4 days, the mixture was acidifed (dilute hydrochloric acid) and extracted thoroughly with ethyl acetate. The extracts were combined, dried (magnesium sulphate) and evaporated down to give an oil, which was flash chromatographed on silica using 60% ethyl ether/hexane. Fractionds with R$_f$ of about 0.26 and 0.21 (mixture of diasteriomers) onj evaporation gave the title diol as an off-white solid.

'H NMR (CDCl$_3$) (mixture of diasteriomers): 0.26 (s, 3H), 0.88 (t, 3H, J=6.5 Hz), 1.26–1.60 (m, 2H), 3.55–3.85 (m, 1H), 4.45 (d, 1H), 4.65 (d, 1H), 6.60 (s, 1H), 6.66 (s, 1H) and 7.63 (s, 1H).

MS m/e (% abundance): 354 (M$^+$, 4), 339 (2), 321 (1), 171 (17), 170 (100), 169 (87), 153 (13), 98 (16), 75 (13), 73 (59), 57 (11) and 55 (12).

3-(1,2-Diacetoxytridecyl)-5-trimethylsilylfuran

A mixture of 4-(1,2-dihydroxytridecyl-5-trimethylsilylfuran (110 mg, 0.31 mmol), acetic anhydride (1.5 ml) and pyridine (1.5 ml) was stirred at room temperature for 13 hours. After most of the solvent was removed under high vacuum, the residue was dissolved in dichloromethane and washaed thoroughly with aqueous copper sulphate. Evaporation of the dried (magnesium sulphate) organic phase gave an oil, which was purified by flash chromatography using 10% ethyl ether/hexane. Fractions with R$_f$ of about 0.52 and 0.46 (mixture of diasteriomers) on evaporation gave the title diacetate.

'H NMR (CDCl$_3$) (mixture of diasteriomers): 0.29, 0.30 (2S, 9H), 0.92 (t, 3H, J=7.0 Hz), 1.30 (br, 18H), 1.50 (m, 2H), 2.09, 2.10, 2.11, 2.12 (4S), 5.25 (m, 1H), 5.88 (d, 1H, J=7.5 Hz), 5.95 (d, 1H, J=3.5 Hz), 6.63 (s, 1H), 6.65 (s, 1H), 7.66 (s, 1H) and 7.67 (s, 1H).

MS m/e (% abundance): 438(M$^+$ +2), 423(2), 407(2), 396(1), 379(100), 337(16), 336(23), 169(23), 117(13), 73(16) and 61(14).

4-(1,2-Diacetoxytridecyl)-5-hydroxy-2(5H)-furanone

A mixture of 3-(1,2-diacetoxytridecyl)-5-trimethylsilylfuran (82 mg, 0.19 mmol) and Rose Bengal (5 mg) in tetrahydrofuran (7 ml) was exposed to singlet oxygen at −78° for 3 hours. The residue, after solvent removal, was purified by preparative TLC (silica plate developed with 60% ethyl ether/hexane). The title furanone was obtained as a pale yellow oil.

'H NMR (CDCl$_3$) (mixture of diasteriomers): 0.9 (t, 3H, J =6.4 Hz), 1.27 (brs, 18H), 1.65 (br, 2H), 2.10, 2.11, 2.17, 2.21 (4S, 12H), 5.21 (brt, 1H), 5.50–5.80 (2 brm, 2H), 6.03 (brs, 1H), 6.13 (brs, 1H) and 6.16 (brs, 1H).

$^{13}$C NMR (CDCl$_3$): 14.1, 20.6, 20.7, 20.9, 22.6, 25.2, 25.3, 29.1, 29.2, 29.3, 29.4, 29.5, 31.8, 70.0, 72.7, 98.2, 120.5, 121.2, 161.2, 164.0, 170.1 and 171.2.

MS exact mass calculated for C$_{21}$H$_{38}$O$_7$N (M+NH$_4$)$^+$416.2648, found 416.2652.

EXAMPLE 84

4-(1,2-Dihydroxyethyl)-2-triethylsilylfuran (prepared by the procedure of Example 1 using 5-triethylsilyl-3-furaldehyde in place of the corresponding trimethylsilyl furaldehyde and preparing the 5-triethylsilyl-3-furaldehyde by the alternative procedure using triethylsilyl Chloride) is reacted with dodecanoyl chloride in the presence of triethylamine to give 4-(1-hydroxy-2-tridecanoyloxyethyl)-2-triethylsilylfuran. Treating this 1-hydroxy compound with acetic anhydride and pyridine gives 4-(1-acetoxy-2-tridecanoyl-oxyethyl)-2-triethylsilylfuran.

A mixture of the above prepared furan and Rose Bengal in tetrahydrofuran is exposed to singlet oxygen to give (4-(1-acetoxy-2-tridecanoyloxyethyl)-5-hydroxy-2(5H)-furanone.

EXAMPLE 85

Reacting 4-(1,2-dihydroxyethyl)-2-triethyl-silylfuran with acetyl chloride and triethylamine gives 4-(1-hydroxy-2-acetoxyethyl)-2-triethylsilylfuran. Reacting this intermediate with dodecanoyl chloride and triethylamine and oxidizing the resulting 4-(1-dodecanoyloxy-2-acetoxyethyl)-2-triethylsilylfuran gives 4-(1-dodecanoyloxy-2-acetoyethyl)-5-hydroxy-2(5H)-furanone.

EXAMPLE 86

Using dodecyl isocyanate in place of dodecanoyl chloride in the procedure of Example 82 gives, as the product, 4-[1-acetoxy-2-(N-dodecylcarbamoyloxy) ethyl]-5-hydroxy-2(5H)-furanone.

EXAMPLE 87

In the procedure of Example 74, using methyl methylphosphonochloridate in place of dodecanoyl chloride, the product is 4-[1-acetoxy-2-OP(O)(OCH$_3$) (CH$_3$) ethyl]-5-hydroxy-2(5H)-furanone.

EXAMPLE 88

Reacting 4-[1-hydroxy-2-[3-(2-naphthyl)propoxy]ethyl]-2-trimethylsilfuran with tert-butyl lithium and phenylisocyanate gives 4-[1-phenylcarbamoyl-2-[3-(2-naphthyl)propoxy]ethyl]-2-trimethylsilylfuran. Oxidizing this intermediate with singlet oxygen gives 4-[1-phenylcarbamoyl-2-[3-(2-naphthyl)propoxy]ethyl]-5-hydroxy-2(5H)-furanone.

EXAMPLE 89

As in Example 88, but substituting phenylisocyanate with ethyl chloroformate and carry through the reaction sequence gives 4-[1-ethoxycarbomyloxy-2-[3-(2-naphthyl)propoxy]ethyl]-5-hydroxy-2(5H)-furanone.

EXAMPLE 90

As in Example 88, but substituting phenylisocyanate with chlorosulfonyl isocyanate and carry through the reaction sequence to give 4-[1-carbamoyl-2-[3-(2-naphthyl)propoxy]ethyl]-5-hydroxy-2(5H) furanone.

EXAMPLE 91

As in Example 88, but substituting phenyl isocyanate with diethylchlorophosphate and carry through the reaction sequence to give 4-[1-diethylphosphonyl-2-[3-(2-naphthyl)propoxy]ethyl]-5-hydroxy-2(5H)-furanone.

EXAMPLE 92

Reacting 4-[1-diethylphosphonyl-2-[3-(2-naphthyl)propoxy]ethyl]-2-trimethylsilylfuran, obtained from Example 91, with bromotrimethylsilane and oxidizing this intermediate with singlet oxygen gives 4-[1-phosphonyl-2-[3-(2-naphthyl)propoxy]ethyl]-5-hydroxy-2(5H)-furanone.

BIOLOGICAL TESTING

The following test procedures may be used to demonstrate activity of the compounds of this invention:

Inhibition of Phospholipase $A_2$

The effect of compounds of this invention on bee venom phospholipase $A_2$ is determined by the following procedure:

a. Bee venom phospholipase $A_2$ in 10 μM HEPES (pH 7.4) with 1 mM $CaCl_2$ is incubated with vehicle or test agent for 1.0 hour at 41°.
b. 1.36 mM phosphotidylcholine, 2.76 mM Triton X-100 are dispersed in buffer by sonication and then mixed with L-3 phosphatidylcholine, 1-palmitoyl-2-(1-$^{14}$C) palmitoyl for 10 min.
c. Start the reaction by the addition of enzyme (0.495 units/ml).
d. Incubation for 15 sec. at 41°.
e. Reaction is terminated by addition of 2.5 ml of isopropanol: n-heptane: 0.5M $H_2SO_4$ (40:10:1; v:v:v).
f. 2.0 ml n-heptane and 1.0 ml $H_2O$ added; mixture centrifuged.
g. 2.0 ml n-heptane removed and treated with 200-300 mg of silica gel HR60.
h. Samples centrifuged; 1 ml of n-heptane SN removed and added to 10 ml scintillation fluid.
i. Samples counted on a scintillation counter.

Mouse Ear Anti-Inflammatory Assay

Test compound and phorbol myristate acetate (PMA) are topically applied simultaneously to the pinnae of the left ears of mice. PMA alone is applied to the right ear. Three hours and 20 minutes after application, the mice are sacrificed, left and right ears removed, and standard sized bores taken. Edema (inflammation) is measured as the difference in weight between left and right ears [Van Arman, C.G., Clin Pharmacol Ther (1974) 16:900–904].

Inhibition of Ornithine Decarboxylase (ODC)

Tape-stripping mouse epidermis and TPA are quick and convenient methods of inducing ODC activity. M. Connor and N. Lowe (Cancer Res. 43, 5174, 1983; Brit. J. Dermatol. 275, 98, 1984) have studied the ability of retinoids to inhibit ODC. Trans-retinoic acid, 13-cis retinoic acid, and etretinate were all active at inhibiting ODC and therapeutically active in humans. Therefore, inhibition of ODC is an in vivo method to demonstrate the potential efficacy of drugs for epidermal hyperproliferation such as psoriasis. Lowe et al. (J. Amer. Acad. Dermatol. 6:697, 1982) have shown that polyamines and ODC are elevated in psoriasis.

In vitro methods have also been useful in determining the anti-hyperproliferative activity of drugs. C. Marcelo and J. Tomich (J. Invest. Dermatol. 81, 64s, 1983) have shown that neonatal mouse keratinocyte cultures can be used to identify drugs that inhibit DNA synthesis. More recently, R. Weiss, Eichner, R. and Sunn, T. T, J. Cell Biol., 98:1397–1406, (1984) have shown that epidermal cultures are in fact, a model of epidermal hyperproliferation and therefore a good model for testing drugs that inhibit hyperproliferation.

Calcium Channel (mobilization) inhibition assay

Polymorphonuclear leukocytes (PMNa), gastric glands, $GH_3$ cells, A431 cells, spleen cells, human keratinocytes corneal cells, etc. were loaded with the $Ca^{2+}$ sensitive fluorescent dye, Fura-2. The appropriate cell type was chosen and the potency and efficacy of the anti-inflammatory furanones on calcium mobilization, calcium channel inhibition quantitated. The methods used for A431 cells listed below are representative of those used for other cells.

A431 cells were detached using a 5-10 min trypsin-EDTA treatment whereas $GH_3$ cells were treated 2 to 5 min with a 1% pancreatin solution. Cells were immediately washed twice in a 20 mM HEPES buffer (pH 7.4) containing 120 mM NaCl, 6 mM KCl, 1 mM $MgSO_4$, 1 mg/ml glucose and 1 mg/ml pyruvate and 1.4 mM calcium (medium A). Approximately $5 \times 10^6$ cells were suspended in medium A and incubated with 4 μM fura-2-AM for 15 min at 37° C. After washing the fura-2 loaded cells, the uptake of dye was checked using fluorescence microscopy and found to be evenly distributed in the cytosol of all cells. Fluorescence was continuously recorded with a Perkin-Elmer LS-5 spectrofluorometer. The excitation wavelength was set at 340 nm and emission wavelength set at 500 nm. The cell suspension was continually stirred, maintained at 37° C. and equilibrated for approximately 5 min before addition of various agents. $[Ca^{2+}]_i$ was calculated using the following formula:

$$[Ca^{2+}]_i = 200 \frac{F - F_{min}}{F_{max} - F}$$

All fluorescence values were measured relative to a EGTA-quenched signal determined as follows: F was the relative fluorescence measurement of the sample.

$F_{max}$ was determined by lysing the cells with digitonin (100 μg/ml) in DMSO. After $F_{max}$ was determined the pH was adjusted to 8, with NaOH and $Ca^{2+}$ chelated with 3 mM EGTA to totally quench the fura-2 signal and obtain $F_{min}$.

When quin-2 was used, cells were incubated with 10 μM quin-2 at 37° C. for 1 hr, washed and then used.

Inhibition of Phosphoinositide-specific Phospholipase C

The effect of compounds of this invention on phosphoinositide-specific phospholipase C may be determined by procedures described by Bennet et al, *Molecular Pharmacology* 32:587-593 (1987).

What is claimed is:

1. A compound of the formula:

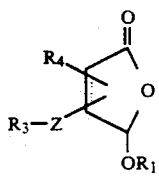

in which:
the dotted line represents absence of a bond or a single bond;
$R_1$ is hydrogen, $C_1-C_4$ alkyl, benzyl, $C_1-C_{20}$ alkanoyl, cyclohexanoyl, benzoyl, phenyl ($C_{1-4}$ alkanoyl) or naphthoyl;
Z is —C($OR_2$)H—;
$R_2$ is $C_1-C_4$ alkyl, $C_1-C_{20}$ alkanoyl, trihaloacetyl, cyclohexanoyl, benzoyl, phenyl ($C_{1-4}$ alkanoyl), phenyl ($C_2-C_{14}$ alkenoyl), naphthoyl, or carbamoyl optionally N-substituted by one or two $C_{1-4}$ alkyl groups or by one alpha-($C_1-C_4$ alkyl)benzyl group;
$R_3$ is hydrogen, $C_1-C_{20}$ straight chain alkyl, phenyl($C_1-C_{20}$ straight chain alkyl or alkenyl of 1-6 uncojugated double bonds), cyclohexyl($C_1-C_{20}$ straight chain alkyl or alkenyl having 1-6 unconjugated double bonds), phenyl, cyclohexyl or benzothienyl($C_1-C_{20}$ alkyl or alkenyl having 1-6 unconjugated double bonds), 4-methyl-3-pentenyl, 4-methyl-6-(2,6,6-trimethyl-cyclohex-1-enyl)hex-3-enyl, 1-(2-ethenyl)-1,5,9-trimethyl-deca-4,8-dienyl, Y-$(CH_2)_n$ or B-(straight chain $C_3-C_{14}$ alkynyl);
$R_4$ is hydrogen, bromo or chloro but is not bromo or chloro when $R_3$ contains a double bond;
n is 6-12;
Y is $OR_5$, $CO_2R_6$, t-butyl, t-butyldimethylsilyl, diphenylmethyl, triphenylmethyl, pyridyl, thienyl, quinolyl, N-$C_1-C_4$ alkylpyrroyl, N-$C_1-C_4$ alkylpiperidyl, N-$C_1-C_4$ alkylpyridinium halide or naphthyl;
$R_5$ is hydrogen, $C_1-C_4$ alkyl or $C_1-C_4$ alkanoyl;
$R_6$ is hydrogen or $C_1-C_4$ alkyl;
B is hydrogen, phenyl, pyridyl or naphthyl; and a lactone formed when $R_2$ is hydrogen and $R_3$ is $(CH_2)_{11-15}$ COOH; said phenyl in the definition of $R_3$ being optionally substituted by $C_1-C_{14}$ alkyl, alkenyl, alkynyl or aryl, $CO_2R_6$, $C_1-C_4$ alkoxy or halo.

2. A compound of claim 1 in which the dotted line represents a single bond; and $R_3$ is hydrogen, $C_1-C_{20}$ straight chain alkyl, phenyl($C_1-C_{20}$ straight chain alkyl), cyclohexyl($C_1-C_{20}$ straight chain alkyl), phenyl, cyclohexyl or benzothienyl($C_1-C_{20}$ alkyl), 4-methyl-3-pentenyl, 4-methyl-6-(2,6,6-trimethylcyclohex-1-enyl)-hex-3-enyl, 1-(2-ethenyl)-1,5,9-trimethyldeca-4,8-dienyl, Y-$(CH_2)_n$ or B-(straight chain $C_3-C_{14}$ alkynyl).

3. A compound of claim 1 where $R_3$-Z is in the 4 position on the 2-furanone ring.

4. A compound of claim 3 where $R_1$ is hydrogen or $C_1-C_{20}$ alkanoyl; $R_2$ is $C_1-C_{20}$ alkanoyl; $R_3$ is $C_5-C_{20}$ straight chain alkyl, benzothienyl($C_1-C_{20}$ alkyl), or carbamoyl optionally N-substituted by one or two $C_1-C_4$ alkyl groups or by one alpha($C_1-C_4$ alkyl)benzyl group, 4-methyl-3-pentenyl, 4-methyl-6-(2,6,6-trimethylcyclohex-1-enyl)hex-3-enyl, 1-(2-ethenyl)-1,5,9-trimethyldeca-4,8-dienyl, and $R_4$ is hydrogen.

5. 4-[1-acetoxy-7-benzo(b)thien-2-yl-heptyl]-5-hydroxy-2(5H)-furanone.

6. 4-(1-acetoxy-tridecyl)-5-hydroxy-2(5H)-furanone.

7. 4-(1-acetoxy-6-phenylhexyl)-5-hydroxy-2(5H)-furanone.

8. 4-(1-acetoxy-6-(2-naphtyl)hexyl)-5-hydroxy-2(5H)-furanone.

9. 4-(1-(alpha-methylbenzylcarbamoyl)tridecyl)-5-hydroxy-2(5H)-furanone.

10. 4-[1-acetoxy-5-methyl-7-(2,6,6-trimethylcyclohex-1-enyl)-hept-4-enyl]-5-hydroxy-2-(5H)-furanone.

11. A pharmaceutical composition which comprises a pharmaceutical carrier and a therapeutically effective amount of a compound of claim 1.

12. A method of treating inflammation or an allergic response in a mammal which comprises administering to a mammal a therapeutically effective amount of a compound of claim 1 alone or in conjunction with a pharmaceutically acceptable excipient.

13. A method of treating psoriasis which comprises administering to a mammal a therapeutically effective amount of a compound of claim 1 alone or in conjunction with a pharmaceutically acceptable excipient.

14. A compound of the formula:

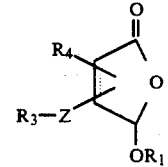

in which
the dotted line represents absence of a bond or a single bond;
$R_1$ is hydrogen, $C_1-C_4$ alkyl, benzyl $C_1-C_{20}$ alkanoyl, cyclohexanoyl, benzoyl, phenyl ($C_{1-4}$ alkanoyl) or naphthoyl;
Z is —C($OR_2$)H—;
$R_2$ is $C_1-C_{20}$ alkanoyl, trihaloacetyl, cyclohexanoyl, benzoyl, phenyl($C_{1-4}$ alkanoyl), phenyl($C_2-C_{14}$ alkenoyl), naphthoyl, or carbamoyl optionally N-substituted by one or two $C_{1-4}$ alkyl groups or by one alpha-($C_1-C_4$ alkyl)benzyl group;
$R_3$ is hydrogen, $C_1-C_{20}$ straight chain alkyl, phenyl($C_1-C_{20}$ straight chain alkyl or alkenyl of 1-6 unconjugated double bonds), cyclohexyl($C_1-C_{20}$ straight chain alkyl or alkenyl having 1-6 unconjugated double bonds), phenyl, cyclohexyl or benzothienyl($C_1-C_{20}$ alkyl or alkenyl having 1-6 unconjugated double bonds), 4-methyl-3-pentenyl, 4-methyl-6-(2,6,6-trimethyl-cyclohex-1-enyl)hex-3-enyl, 1-(2-ethenyl)-1,5,9-trimethyl-deca-4,8-dienyl, Y—$(CH_2)_n$ or B-(straight chain $C_3-C_{14}$ alkynyl);

$R_4$ is hydrogen, bromo or chloro but is not bromo or chloro when $R_3$ contains a double bond;

n is 6–12;

Y is $OR_5$, $CO_2R_6$, t-butyl, t-butyldimethylsilyl, diphenylmethyl, triphenylmethyl, pyridyl, thienyl, quinolyl, N—$C_1$-$C_4$ alkylpyrrolyl, N—$C_1$-$C_4$ alkylpiperidyl, N—$C_1$-$C_4$ alkylpyridinium halide or naphthyl;

$R_5$ is hydrogen, $C_1$-$C_4$ alkyl or $C_1$-$C_4$ alkanoyl;

$R_6$ is hydrogen or $C_1$-$C_4$ alkyl;

B is hydrogen, phenyl, pyridyl or naphthyl; and a lactone formed when $R_2$ is hydrogen and $R_3$ is $(CH_2)_{11-15}$ COOH; said phenyl in the definition of $R_3$ being optionally substituted by $C_1$-$C_{14}$ alkyl, alkenyl, alkynyl or aryl, $CO_2R_6$, $C_1$-$C_4$ alkoxy or halo.

15. A compound of the formula

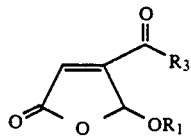

where $R_1$ is hydrogen or $C_1$-$C_{20}$ alkanoyl, and $R_3$ is $C_5$-$C_{20}$ straight chain alkyl, benzothienyl($C_1$-$C_{20}$ alkyl), 4-methyl-3-pentenyl, 4-methyl-6-(2,6,6-trimethylcyclohex-1-enyl)hex-3-enyl or 1-(2-ethenyl)-1,5,9-trimethyldeca-4,8-dienyl.

16. A compound of the formula

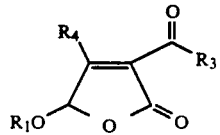

where $R_1$ is hydrogen, $C_1$-$C_4$ alkyl, benzyl, $C_1$-$C_{20}$ alkanoyl, cyclohexanoyl, benzoyl, pheny($C_{1-4}$ alkanoyl) or naphthoyl;

$R_3$ is H, $C_1$-$C_{20}$ straight chain alkyl, phenyl($C_1$-$C_{20}$ straight chain alkyl), cyclohexyl($C_1$-$C_{20}$ straight chain alkyl), phenyl, cyclohexyl or benzothienyl($C_1$-$C_{20}$ alkyl), 4-methyl-3-pentenyl, 4-methyl-6-(2,6,6-trimethylcyclohex-1-enyl)hex-3-enyl, 1-(2-ethenyl)-1,5,9-trimethyldeca-4,8-dienyl, Y—$(CH_2)_n$ or B-(straight chain $C_3$-$C_{14}$ alkynyl);

$R_4$ is hydrogen, bromo, or chloro but is not bromo or chloro when $R_3$ contains a double bond;

n is 6–12;

Y is $OR_5$, $CO_2R_6$, t-butyl, t-butyldimethylsilyl, diphenylmethyl, triphenylmethyl, pyridyl, thienyl, quinolyl, N—$C_1$-$C_4$ alkylpyrrolyl, N—$C_1$-$C_4$ alkylpiperidyl, N—$C_1$-$C_4$ alkylpyridinium halide or naphthyl;

$R_5$ is hydrogen, $C_1$-$C_4$ alkyl or $C_1$-$C_4$ alkanoyl;

$R_6$ is hydrogen or $C_1$-$C_4$ alkyl;

B is hydrogen, phenyl, pyridyl or naphthyl.

17. A compound of the formula

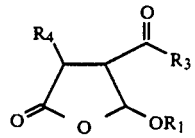

where $R_1$ is hydrogen, $C_1$-$C_4$ alkyl, benzyl, $C_1$-$C_{20}$ alkanoyl, cyclohexanoyl, benzoyl, phenyl($C_1$-$C_4$ alkanoyl) or naphthoyl;

$R_3$ is H, $C_1$-$C_{20}$ straight chain alkyl, phenyl($C_1$-$C_{20}$ straight chain alkyl or alkenyl of 1-6 unconjugated double bonds), cyclohexyl($C_1$-$C_{20}$ straight chain alkyl or alkenyl of 1-6 unconjugated double bonds), phenyl, cyclohexyl or benzothienyl($C_1$-$C_{20}$ alkyl or alkenyl of 1-6 unconjugated double bonds), 4-methyl-3-pentenyl, 4-methyl-6-(2,6,6-trimethylcyclohex-1-enyl)hex-3-enyl, 1-(2-ethenyl)-1,5,9-trimethyldeca-4,8-dienyl, Y—$(CH_2)_n$ or B-(straight chain $C_3$-$C_{14}$ alkynyl);

$R_4$ is hydrogen, bromo, or chloro but is not bromo or chloro when $R_3$ contains a double bond;

n is 6–12;

Y is $OR_5$, $CO_2R_6$, t-butyl, t-butyldimethylsilyl, diphenylmethyl, triphenylmethyl, pyridyl, thienyl, quinolyl, N—$C_1$-$C_4$ alkylpyrrolyl, N—$C_1$-$C_4$ alkylpiperidyl, N—$C_1$-$C_4$ alkylpyridinium halide or naphthyl;

$R_5$ is hydrogen, $C_1$-$C_4$ alkyl or $C_1$-$C_4$ alkanoyl;

$R_6$ is hydrogen or $C_1$-$C_4$ alkyl;

B is hydrogen, phenyl, pyridyl or naphthyl.

18. A compound of the formula

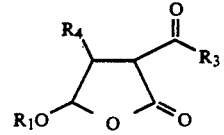

where $R_1$ is hydrogen, $C_1$-$C_4$ alkyl, benzyl, $C_1$-$C_{20}$ alkanoyl, cyclohexanoyl, benzoyl, pheny($C_{1-4}$ alkanoyl) or naphthoyl;

$R_3$ is H, $C_1$-$C_{20}$ straight chain alkyl, phenyl($C_1$-$C_{20}$ straight chain alkyl or alkenyl of 1-6 unconjugated double bonds), cyclohexyl($C_1$-$C_{20}$ straight chain alkyl or alkenyl of 1-6 unconjugated double bonds), phenyl, cyclohexyl or benzothienyl($C_1$-$C_{20}$ alkyl or alkenyl of 1-6 unconjugated double bonds), 4-methyl-3-pentenyl, 4-methyl-6-(2,6,6-trimethylcyclohex-1-enyl)hex-3-enyl, 1-(2-ethenyl)-1,5,9-trimethyldeca-4,8-dienyl, Y—$(CH_2)_n$ or B-(straight chain $C_3$-$C_{14}$ alkynyl);

$R_4$ is hydrogen, bromo, or chloro but is not bromo or chloro when $R_3$ contains a double bond;

n is 6–12;

Y is $OR_5$, $CO_2R_6$, t-butyl, t-butyldimethylsilyl, diphenylmethyl, triphenylmethyl, pyridyl, thienyl, quinolyl, N—$C_1$-$C_4$ alkylpyrrolyl, N—$C_1$-$C_4$ alkylpiperidyl, N—$C_1$-$C_4$ alkylpyridinium halide or naphthyl;

$R_5$ is hydrogen, $C_1$-$C_4$ alkyl or $C_1$-$C_4$ alkanoyl;

$R_6$ is hydrogen or $C_1$-$C_4$ alkyl;

B is hydrogen, phenyl, pyridyl or naphthyl.

19. A compound of the formula

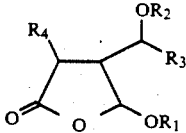

where
- $R_1$ is hydrogen, $C_1$-$C_4$ alkyl, benzyl, $C_1$-$C_{20}$ alkanoyl, cyclohexanoyl, benzoyl, phenyl($C_{1-4}$ alkanoyl) or naphthoyl;
- $R_2$ is hydrogen, $C_1$-$C_4$ alkyl, $C_1$-$C_{20}$ alkanoyl, trihaloacetyl, cyclohexanoyl, benzoyl, phenyl($C_{1-4}$ alkanoyl), phenyl($C_2$-$C_{14}$ alkenoyl), naphthoyl, or carbamoyl optionally N-substituted by one or two $C_{1-4}$ alkyl groups or by one alpha-($C_1$-$C_4$ alkyl)-benzyl group;
- $R_3$ is H, $C_1$-$C_{20}$ straight chain alkyl, phenyl($C_1$-$C_{20}$ straight chain alkyl or alkenyl of 1-6 unconjugated double bonds), cyclohexyl($C_1$-$C_{20}$ straight chain alkyl or alkenyl of 1-6 unconjugated double bonds), phenyl, cyclohexyl or benzothienyl($C_1$-$C_{20}$ alkyl or alkenyl of 1-6 unconjugated double bonds), 4-methyl-3-pentenyl, 4-methyl-6-(2,6,6-trimethylcyclohex-1-enyl)hex-3-enyl, 1-(2-ethenyl)-1,5,9-trimethyldeca-4,8-dienyl, Y—(CH$_2$)$_n$ or B-(straight chain $C_3$-$C_{14}$ alkynyl);
- $R_4$ is hydrogen, bromo, or chloro but is not bromo or chloro when $R_3$ contains a double bond;
- n is 6-12;
- Y is OR$_5$, CO$_2$R$_6$, t-butyl, t-butyldimethylsilyl, diphenylmethyl, triphenylmethyl, pyridyl, thienyl, quinolyl, N—$C_1$-$C_4$ alkylpyrrolyl, N—$C_1$-$C_4$ alkylpiperidyl, N—$C_1$-$C_4$ alkylpyridinium halide or naphthyl;
- $R_5$ is hydrogen, $C_1$-$C_4$ alkyl or $C_1$-$C_4$ alkanoyl;
- $R_6$ is hydrogen or $C_1$-$C_4$ alkyl;
- B is hydrogen, phenyl, pyridyl or naphthyl; and a lactone formed when $R_2$ is hydrogen and $R_3$ is (CH$_2$)$_{11-15}$ COOH; said phenyl in the definition of $R_3$ being optionally substituted by $C_{1-14}$ alkyl, alkenyl, alkynyl or aryl, CO$_2$R$_6$, $C_1$-$C_{14}$ alkoxy or halo.

20. A compound of the formula

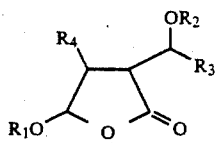

where
- $R_1$ is hydrogen, $C_1$-$C_4$ alkyl, benzyl, $C_1$-$C_{20}$ alkanoyl, cyclohexanoyl, benzoyl, phenyl($C_{1-4}$ alkanoyl) or naphthoyl;
- $R_2$ is hydrogen, $C_1$-$C_4$ alkyl, $C_1$-$C_{20}$ alkanoyl, trihaloacetyl, cyclohexanoyl, benzoyl, phenyl($C_{1-4}$ alkanoyl), phenyl($C_2$-$C_{14}$ alkenoyl), naphthoyl, or carbamoyl optionally N-substituted by one or two $C_{1-4}$ alkyl groups or by one alpha-($C_1$-$C_4$ alkyl)-benzyl group;
- $R_3$ is H, $C_1$-$C_{20}$ straight chain alkyl, phenyl($C_1$-$C_{20}$ straight chain alkyl or alkenyl of 1-6 unconjugated double bonds), cyclohexyl($C_1$-$C_{20}$ straight chain alkyl or alkenyl of 1-6 unconjugated double bonds), phenyl, cyclohexyl or benzothienyl($C_1$-$C_{20}$ alkyl or alkenyl of 1-6 unconjugated double bonds), 4-methyl-3-pentenyl, 4-methyl-6-(2,6,6-trimethylcyclohex-1-enyl)hex-3-enyl, 1-(2-ethenyl)-1,5,9-trimethyldeca-4,8-dienyl, Y—(CH$_2$)$_n$ or B-(straight chain $C_3$-$C_{14}$ alkynyl);
- $R_4$ is hydrogen, bromo, or chloro but is not bromo or chloro when $R_3$ contains a double bond;
- n is 6-12;
- Y is OR$_5$, CO$_2$R$_6$, t-butyl, t-butyldimethylsilyl, diphenylmethyl, triphenylmethyl, pyridyl, thienyl, quinolyl, N—$C_1$-$C_4$ alkylpyrrolyl, N—$C_1$-$C_4$ alkylpiperidyl, N—$C_1$-$C_4$ alkylpyridinium halide or naphthyl;
- $R_5$ is hydrogen, $C_1$-$C_4$ alkyl or $C_1$-$C_4$ alkanoyl;
- $R_6$ is hydrogen or $C_1$-$C_4$ alkyl;
- B is hydrogen, phenyl, pyridyl or naphthyl; and a lactone formed when $R_2$ is hydrogen and $R_3$ is (CH$_2$)$_{11-15}$ COOH; said phenyl in the definition of $R_3$ being optionally substituted by $C_{1-14}$ alkyl, alkenyl, alkynyl or aryl, CO$_2$R$_6$, $C_1$-$C_{14}$ alkoxy or halo.

21. A compound of the formula:

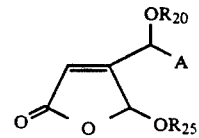

in which:
- $R_{20}$ is hydrogen, $C_1$-$C_{14}$ alkanoyl, COHNR$_{23}$ or CO$_2$R$_{24}$;
- $R_{23}$ is phenyl or $C_1$-$C_4$ alkyl;
- $R_{24}$ is $C_1$-$C_6$ alkyl;
- A is CH$_2$O—R$_{21}$ or $$\underset{\underset{OCOR_{22}}{|}}{CH(C_7\text{-}C_{14}\text{ alkyl});} \text{ or}$$

when $R_{20}$ is $C_1$-$C_{14}$ alkanoyl, A may be CH$_2$O-COR$_{22}$ or CH$_2$OP(O) (OR$_{22}$)R$_{22}$;
- $R_{21}$ is $C_7$-$C_{14}$ alkanoyl, N—($C_6$-$C_{14}$ alkyl) carbamoyl, naphthyl-($C_1$-$C_6$ alkyl), pyridyl-($C_1$-$C_6$ alkyl) or methoxyethoxymethoxymethyl;
- $R_{22}$ is $C_1$-$C_4$ alkyl; and
- $R_{25}$ is H, $C_{1-6}$ alkanoyl or $C_{1-6}$ alkyl.

22. A compound of claim 21 in which $R_{20}$ is $C_1$-$C_{14}$ alkanoyl and A is CH$_2$—O—R$_{21}$.

23. A compound of claim 22 in which $R_{21}$ is $C_8$-$C_{14}$ alkanoyl, naphthylpropyl, pyridylpropyl or methoxyethoxymethoxymethyl.

24. A compound which is 4-[1-dodecanoyloxy-2-(2-methoxyethoxy)methoxyethyl]-5-hydroxy-2(5H)-furanone.

25. A compound which is 4-(1,2-didodecanoyloxyethyl)-5-hydroxy-2(5H)-furanone.

26. A compound which is 4-[1-acetoxy-2-[3-(2-naphthyl)propoxy]ethyl]-5-hydroxy-2(5H)-furanone.

27. A compound which is 4-[1-hydroxy-2-[3-(2-naphthyl)propoxy]ethyl]-5-hydroxy-2(5H)-furanone.

28. A pharmaceutical composition which comprises a pharmaceutical carrier and a therapeutically effective amount of a compound of claim 21.

29. A method of treating inflammation or an allergic response in a mammal which comprises administering to a mammal a therapeutically effective amount of a compound of claim 21 alone or in conjunction with a pharmaceutically acceptable excipient.

30. A method of treating psoriasis which comprises administering to a mammal a therapeutically effective amount of a compound of claim 21 either alone or in conjunction with a pharmaceutically acceptable excipient.

* * * * *

UNITED STATES PATENT AND TRADEMARK OFFICE
CERTIFICATE OF CORRECTION

PATENT NO. : 5,134,128
DATED : July 28, 1992
INVENTOR(S) : Gary C. M. Lee et al.

It is certified that error appears in the above-identified patent and that said Letters Patent is hereby corrected as shown below:

Column 12, line 64, "($CDCl_3$);" should be —($CDCl_3$):—;
Column 21, line 59, "3H)," should be —3H,—;
Column 21, line 65, before "(3)" add — 265 —;
Column 22, line 60, "$R_f$0.22" should be —$R_f$ 0.22—;
Column 23, line 17, "$R_f$0.38" should be —$R_f$ 0.38—;
Column 23, line 48, "$R_f$0.22" should be —$R_f$ 0.22—;
Column 24, line 26, "$C_{17}H_{28}O_5$312.2015" should be —$C_{17}H_{28}O_5$ 12.2015—;
Column 25, line 38, "$R_f$of" should be —$R_f$ of—;
Column 40, line 37, "20x20" should be —AE 20x20—;
Column 54, line 45, "2t" should be —2 t—;
Column 60, line 60, "1.9" should be —1,9—;
Column 67, line 65, "(s, 1)" should be —(s, 1H)—;
Column 69, line 64, "57.7" should be —57.5—;
Column 75, line 46, before "3.85" insert — 3.55 (brm, 2H), —;
Column 77, line 38, "trimethysilyllfuran" should be
    —trimethysilylfuran—;
Column 77, line 47, "Fractionds" should be —Franctions—;
Column 77, line 48, "onj" should be —on—;
Column 78, line 37, "Chloride" should be —chloride—;
Column 78, line 45, "(4-" should be —4—;
Column 78, line 55, "acetoyethyl" should be —acetoxyethyl—;

UNITED STATES PATENT AND TRADEMARK OFFICE
CERTIFICATE OF CORRECTION

PATENT NO. : 5,134,128
DATED : July 28, 1992
INVENTOR(S) : Gary C. M. Lee et al.

It is certified that error appears in the above-identified patent and that said Letters Patent is hereby corrected as shown below:

Column 81, line 13, "Bennet" should be —Bennett—;

Column 81, line 40, "uncojugated" should be —unconjugated—;

Column 81, line 53, "alkylpyrroyl" should be —alkylpyrrolyl—.

Signed and Sealed this

Twenty-sixth Day of April, 1994

Attest:

BRUCE LEHMAN

Attesting Officer  Commissioner of Patents and Trademarks

UNITED STATES PATENT AND TRADEMARK OFFICE
CERTIFICATE OF CORRECTION

PATENT NO. : 5,134,128

DATED : July 28, 1992

INVENTOR(S) : Gary C. M. Lee

It is certified that error appears in the above-identified patent and that said Letters Patent is hereby corrected as shown below:

Column 3, line 13, "alkyl);OCOR$_{22}^-$" should be —alkyl), OCOR$_{22}$;—;

Column 22, line 45, "cald" should be —cald.—;

Column 23, line 1, "cald" should be —cald.—;

Column 23, line 27, "cald" should be —càld.—;

Column 26, line 22, "cald" should be —cald.—;

Column 40, line 36, "a©oi Å" should be —an oil—;

Column 40, line 37, "20x20 cm Å" should be —20x20 cm—;

Column 44, line 29, "phenydecyl" should be —phenyldecyl—;

Column 53, line 13, "5.4jo ((t, 1H), 5.05(brs" should be
 —5.40 (t, 1H), 5.05(brs,—;

Column 55, line 38-39 , "then-treated" should be —then treated—;

Column 56, line 8, "trmethylsily" should be —trimethylsilyl—;

Column 56, line 9, after "to" delete "the";

Column 57, line 62 "give" should be —gave—;

Column 64, line 8, "(s 3H)" should be —(s, 3H)—.

UNITED STATES PATENT AND TRADEMARK OFFICE
CERTIFICATE OF CORRECTION

PATENT NO. : 5,134,128
DATED : July 28, 1992
INVENTOR(S) : Gary C. M. Lee

It is certified that error appears in the above-indentified patent and that said Letters Patent is hereby corrected as shown below:

Column 53, line 14, "2.a76(t," should be --2.76 (t,--.

Signed and Sealed this

Seventeenth Day of May, 1994

Attest:

BRUCE LEHMAN

Attesting Officer     Commissioner of Patents and Trademarks